United States Patent
Cheng

(10) Patent No.: US 9,164,084 B2
(45) Date of Patent: Oct. 20, 2015

(54) METHODS FOR DETERMINING AGGRESSIVENESS OF A CANCER AND TREATMENT THEREOF

(71) Applicant: Purdue Research Foundation, West Lafayette, IN (US)

(72) Inventor: Ji-Xin Cheng, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/371,598

(22) PCT Filed: Jan. 25, 2013

(86) PCT No.: PCT/US2013/023095
§ 371 (c)(1),
(2) Date: Jul. 10, 2014

(87) PCT Pub. No.: WO2013/116096
PCT Pub. Date: Aug. 8, 2013

(65) Prior Publication Data
US 2014/0336261 A1 Nov. 13, 2014

Related U.S. Application Data

(60) Provisional application No. 61/753,007, filed on Jan. 16, 2013, provisional application No. 61/592,819, filed on Jan. 31, 2012.

(51) Int. Cl.
*A61K 31/18* (2006.01)
*G01N 33/50* (2006.01)
*A61B 5/00* (2006.01)

(52) U.S. Cl.
CPC .......... *G01N 33/5091* (2013.01); *A61B 5/0073* (2013.01); *A61B 5/4842* (2013.01); *A61K 31/18* (2013.01)

(58) Field of Classification Search
CPC ........................... A61K 31/18; G01N 33/4091
USPC ............................................ 435/29; 514/604
See application file for complete search history.

(56) References Cited

U.S. PATENT DOCUMENTS

| | | | |
|---|---|---|---|
| 4,794,931 A | 1/1989 | Yock | |
| 4,841,977 A | 6/1989 | Griffith et al. | |
| 4,951,677 A | 8/1990 | Crowley et al. | |
| 5,000,185 A | 3/1991 | Yock | |
| 5,095,911 A | 3/1992 | Pomeranz | |
| 5,135,486 A | 8/1992 | Eberle et al. | |
| 5,167,233 A | 12/1992 | Eberle et al. | |
| 5,176,141 A | 1/1993 | Bom et al. | |
| 5,183,048 A | 2/1993 | Eberle | |
| 5,240,003 A | 8/1993 | Lancee et al. | |
| 5,243,988 A | 9/1993 | Sieben et al. | |
| 5,313,949 A | 5/1994 | Yock | |
| 5,353,798 A | 10/1994 | Sieben | |
| 5,368,037 A | 11/1994 | Eberle et al. | |
| 5,373,845 A | 12/1994 | Gardineer et al. | |
| 5,373,849 A | 12/1994 | Maroney et al. | |
| 5,375,602 A | 12/1994 | Lancee et al. | |
| 5,432,054 A | 7/1995 | Saunders et al. | |
| 6,506,572 B2 | 1/2003 | Biedermann et al. | |
| 6,569,845 B1 | 5/2003 | Futamura et al. | |
| 6,879,604 B2 | 4/2005 | Cook | |
| 2009/0192220 A1 | 7/2009 | White et al. | |
| 2011/0261349 A1 | 10/2011 | Cheng et al. | |
| 2012/0215091 A1 | 8/2012 | Suzuki et al. | |

FOREIGN PATENT DOCUMENTS

| | | |
|---|---|---|
| WO | 02/09246 A1 | 1/2002 |
| WO | 2008/058383 A1 | 5/2008 |
| WO | 2009/067397 A2 | 5/2009 |
| WO | 2012/024687 A2 | 2/2012 |
| WO | 2012/038525 A1 | 3/2012 |

OTHER PUBLICATIONS

Hanahan, D. & Weinberg, R. A. The hallmarks of cancer. Cell 100, 57-70 (2000).
Hanahan, D. & Weinberg, R. A. Hallmarks of Cancer: The Next Generation. Cell 144, 646-674, doi:10.1016/j.cell.2011.02.013 (2011).
Ramos, C. V. & Taylor, H. B. Lipid-rich Carcinoma of Breast—A Clinicopathologic Analysis of 13 Examples. Cancer 33, 812-819 (1974).
Preul, M. C. et al. Accurate, noninvasive diagnosis of human brain tumors by using proton magnetic resonance spectroscopy. Nat Med 2, 323-325 (1996).
Tate, A. R. et al. Towards a method for automated classification of 1H MRS spectra from brain tumours. NMR Biomed 11, 177-191 (1998).
Metser, U. et al. "F-18-FDG PET/CT in the evaluation of adrenal masses." J Nucl Med 47, 32-37 (2006).
Murphy, D. J. "The biogenesis and functions of lipid bodies in animals, plants and microorganisms." Prog Lipid Res 40, 325-438 (2001).
Robert V. Farese, J. & Walther, T. C. "Lipid droplets finally get a little R-E-S-P-E-C-T." Cell 139, 855-860 (2009).
Le, T. T., Huff, T. B. & Cheng, J.-X. "Coherent anti-Stokes Raman scattering imaging of lipids in cancer metastasis." BMC Cancer 9 (2009).
Slipchenko, M. N., Le, T. T., Chen, H. T. & Cheng, J. X. "High-Speed Vibrational Imaging and Spectral Analysis of Lipid Bodies by Compound Raman Microscopy." J Phys Chem B 113, 7681-7686, doi:10.1021/jp902231y (2009). 11.
Slipchenko, M. N. & Cheng, J.-X. "Coherent Raman Spectroscopy" (eds Ji-Xin Cheng & X.Sunney Xie) (Taylor & Francs Group, 2012).
Yue, S. H., Slipchenko, M. N. & Cheng, J. X. Multimodal nonlinear optical microscopy. Laser & Photonics Reviews 5, 496-512, doi:10.1002/lpor.201000027 (2011).

(Continued)

*Primary Examiner* — Raymond Henley, III
(74) *Attorney, Agent, or Firm* — Brown Rudnick LLP; Adam M. Schoen

(57) ABSTRACT

The invention generally relates to methods for determining aggressiveness of a cancer and treatment thereof. Certain aspects of the invention provide methods that involve conducting an assay on a lipid droplet in order to detect an amount of a biomarker within the lipid droplet, and determining aggressiveness of a cancer based upon the amount of the biomarker within the lipid droplet. Other aspects of the invention provide methods for treating a cancer that involve administering an agent that blocks storage of cholesteryl ester in a lipid droplet.

20 Claims, 38 Drawing Sheets

(56) References Cited

OTHER PUBLICATIONS

Wang, H. W. et al. Label-free bond-selective imaging by listening to vibrationally excited molecules. Phys. Rev. Lett. 106, 238106 (2011).
Chen, H. et al. Release of hydrophobic molecules from polymer micelles into cell membranes revealed by Forster resonance energy transfer imaging. Proc Natl Acad Sci U S A 105, 6596-6601 (2008).
Shi, Y. et al. Effective repair of traumatically injured spinal cord by nanoscale block copolymer micelles. Nat. Nanotechnol. 5, 80-87 (2010).
Ablin, R. J., Guinan, P. & Bush, I. M. Lipofuscin Granules in Normal, Benign and Malignant Human Prostatic Tissue. Urol Res 1, 149-151 (1973).
Brunk, U. T. & Terman, A. Lipofuscin: Mechanisms of age-related accumulation and influence on cell function. Free Radic Biol Med 33, 611-619 (2002).
Uchida, K. Lipofuscin-like fluorophores originated from malondialdehyde. Free Radic Res 40, 1335-1338, doi:10.1080/10715760600902302 (2006).
Igawa, T. et al. Establishment and characterization of androgen-independent human prostate cancer LNCaP cell model. Prostate 50, 222-235, doi:10.1002/pros.10054 (2002).
Chen, H., Yang, J., Low, P. S. & Cheng, J. X. Cholesterol level regulates endosome mobility via Rab proteins. Biophys. J. 94, 1508-1520 (2008).
Simons, K. & Ikonen, E. Cell biology—How cells handle cholesterol. Science 290, 1721-1726, doi:10.1126/science.290.5497.1721 (2000).
Tosi, M. R. & Tugnoli, V. Cholesteryl esters in malignancy. Clinica Chimica Acta 359, 27-45, doi:10.1016/j.cccn.2005.04.003 (2005).
Platz, E. A. et al. Statin drugs and risk of advanced prostate cancer. J Nat Cancer Inst 98, 1819-1825, doi:10.1093/jnci/djj499 (2006).
Murtola, T. J. et al. Comparative effects of high and low-dose simvastatin on prostate epithelial cells: The role of LDL. Euro J Pharm 673, 96-100 (2011).
Leon, C. G. et al. Alterations in cholesterol regulation contribute to the production of intratumoral androgens during progression to castration-resistant prostate cancer in a mouse xenograft model. The Prostate 70, 390-400 (2010).
Chen, H. et al. Fast release of lipophilic agents from circulating PEG-PDLLA micelles revealed by in vivo Förster resonance energy transfer imaging. Langmuir 24, 5213-5217 (2008).
Tong, L., He, W. & Cheng, J. X. Visualizing systemic clearance and cellular level biodistribution of gold nanostructures by intrinsic multiphoton luminescence. Langmuir 25, 12454-12459 (2009).
Wang, H., Liu, J., Cooks, R. G. & Ouyang, Z. Paper Spray for Direct Analysis of Complex Mixtures Using Mass Spectrometry. Angew. Chem. Int. Ed. 49, 877-880 (2010).
Cairns RA, Harris IS, Mak TW: Regulation of cancer cell metabolism. Nat Rev Cancer 2012, 11(2):85-95.
Tomita M, Kami K: Systems Biology, Metabolomics, and Cancer Metabolism. Science 2012, 336(6084):990-991.
Koppenol WH, Bounds PL, Dang CV: Otto Warburg's contributions to current concepts of cancer metabolism. Nat Rev Cancer 2012, 11(5):325-337.
Heiden MGV, Cantley LC, Thompson CB: Understanding the Warburg Effect: The Metabolic Requirements of Cell Proliferation. Science 2009, 324(5930):1029-1033.
Jain M, Nilsson R, Sharma S, Madhusudhan N, Kitami T, Souza AL, Kafri R, Kirschner MW, Clish CB, Mootha VK: Metabolite Profiling Identifies a Key Role for Glycine in Rapid Cancer Cell Proliferation. Science 2012, 336 (6084):1040-1044.
Wymann MP, Schneiter R: Lipid signalling in disease. Nat Rev Mol Cell Biol 2008, 9(2):162-176.
Menendez JA, Lupu R: Fatty acid synthase and the lipogenic phenotype in cancer pathogenesis. Nat Rev Cancer 2007, 7:763-777.
Robert V. Farese J, Walther TC: Lipid droplets finally get a little R-E-S-P-E-C-T. Cell 2009, 139:855-860.
Martin S, Parton RG: Lipid droplets: a unified view of a dynamic organelle. Nat Rev Mol Cell Biol 2006, 7(5):373-378.
De Schrijver E, Brusselmans K, Heyns W, Verhoeven G, Swinnen JV: RNA interference-mediated silencing of the fatty acid synthase gene attenuates growth and induces morphological changes and apoptosis of LNCaP prostate cancer cells. Cancer Res 2003, 63(13):3799-3804.
Swinnen JV, Esquenet M, Goossens K, Heyns W, Verhoeven G: Androgens stimulate fatty acid synthase in the human prostate cancer cell line LNCaP. Cancer Res 1997, 57(6):1086-1090.
Swinnen JV, VanVeldhoven PP, Esquenet M, Heyns W, Verhoeven G: Androgens markedly stimulate the accumulation of neutral lipids in the human prostatic adenocarcinoma cell line LNCaP. Endocrinology 1996, 137 (10):4468-4474.
Migita T, Ruiz S, Fornari A, Fiorentino M, Priolo C, Zadra G, Inazuka F, Grisanzio C, Palescandolo E, Shin E et al: Fatty Acid Synthase: A Metabolic Enzyme and Candidate Oncogene in Prostate Cancer. J Natl Cancer Inst 2009, 101 (7):519-532.
Sarker D, Reid AH, Yap TA, de Bono JS: Targeting the PI3K/AKT pathway for the treatment of prostate cancer. Clin Cancer Res 2009, 15(15):4799-4805.
Shulkla S, MacLennan GT, Hartman DJ, Fu P, Resnick MI, Gupta S: Activation of PI3K-Akt signaling pathway promotes prostate cancer cell invasion. Int J Cancer 2007, 121(7):1424-1432.
Gao N, Zhang Z, Jiang BH, Shi XL: Role of PI3K/AKT/mTOR signaling in the cell cycle progression of human prostate cancer. Biochem Biophys Res Commun 2003, 310(4):1124-1132.
Peterson TR, Sengupta SS, Harris TE, Carmack AE, Kang SA, Balderas E, Guertin DA, Madden KL, Carpenter AE, Finck BN et al: mTOR complex 1 regulates lipin 1 localization to control the SREBP pathway. Cell 2011, 146(3):408-420.
Porstmann T, Santos CR, Griffiths B, Cully M, Wu M, Leevers S, Griffiths JR, Chung YL, Schulze A: SREBP activity is regulated by mTORC1 and contributes to Akt-dependent cell growth. Cell Metab 2008, 8(3):224-236.
Shao W, Espenshade PJ: Expanding Roles for SREBP in Metabolism. Cell Metab 2012.
Horton JD, Goldstein JL, Brown MS: SREBPs: activators of the complete program of cholesterol and fatty acid synthesis in the liver. J Clin Invest 2002, 109(9):1125-1131.
Eberle D, Hegarty B, Bossard P, Ferre P, Foufelle F: SREBP transcription factors: master regulators of lipid homeostasis. Biochimie 2004, 86(11):839-848.
Chang TY, Chang CCY, Ohgami N, Yamauchi Y: Cholesterol sensing, trafficking, and esterification. Annu Rev Cell Dev Biol 2006, 22:129-157.
Ikonen E: Cellular cholesterol trafficking and compartmentalization. Nat Rev Mol Cell Biol 2008, 9(2):125-138.
Wang DZ, Dubois RN: Eicosanoids and cancer. Nat Rev Cancer 2010, 10(3):181-193.
Hughes-Fulford M, Chen YF, Tjandrawinata RR: Fatty acid regulates gene expression and growth of human prostate cancer PC-3 cells. Carcinogenesis 2001, 22(5):701-707.
Ghosh J, Myers CE: Arachidonic acid stimulates prostate cancer cell growth: Critical role of 5-lipoxygenase. Biochem Biophys Res Commun 1997, 235(2):418-423.
Darnell, J., Molecular Cell Biology, Third Ed., W.H.Freeman, NY, 1990.
Guo et al. Lipid droplets at a glance ( J Cell Sci, 122:749-752, 2009).
Boström et al., "Isotope fractionation and 13C enrichment in soil profiles during the decomposition of soil organic matter" Oecologia (2007) 153:89-98.
Olofsson et al., "A short review on SSF—an interesting process option for ethanol production from lignocellulosic feedstocks" Biotechnology for Biofuels 2008, p. 1-14.
Herzenberg et al. "Fetal cells in the blood of pregnant women: Detection and enrichment by fluorescence-activated cell sorting" PNAS 76:1453-1455, 1979.
Bianchi et al., "Isolation of fetal DNA from nucleated erythrocytes in maternal blood,"PNAS 87:3279-3283, 1990.
Bruch et al., Trophoblast-Like Cells Sorted From Peripheral Maternal Blood Using Flow Cytometry: A Multiparametric Study Involving Transmission Electron Microscopy and Fetal DNA (Date not provided).
Le et al. BMC Cancer, 9(42): 1-14, 2009.
Seward et al., Mayo Clinic Proceedings 71(7):629-635 (1996).

(56) References Cited

OTHER PUBLICATIONS

Packer et al., Cardiostim Conference 833 (1994), "Ultrasound Cardioscopy," Eur. J.C.P.E. 4(2):193 (Jun. 1994).
Wrenn et al., "ACAT inhibitors CL 283,546 and CL 283,796 reduce LDL cholesterol without affecting cholesterol absorption in African green monkeys." Journal of Lipid Research, 36:1199-1210, 1995.
Brunk et al., Lipofuscin: Mechanisms of Age-Related Accumulation and Influence on Cell Function, Free Radic Biol Med 33, 611-619 (2002).
Igawa, Establishment and Characterization of Androgen-Independent Human Prostate Cancer LNCaP Cell Model, Prostate 50:222-235, (2002).
Wang et al., "Label-Free Bond-Selective Imaging by Listening to Vibrationally Excited Molecules," Phys. Rev. Lett. 106:238106 (2011).
Cheng et al., Essentials of Anatomic Pathology Ch. 9, Humana Press, 2002).
B, M. R. et al., "Maintenance of Intratumoral Androgens in Metastatic Prostate Cancer: A Mechanism for Castration-Resistant Tumor Growth,"Cancer Research 68, 4447-4454 5 (2008).
Simons, "How Cells Handle Cholesterol," Science 290:1721-1726, (2000).
Tosi et al., Clinica Chimica Acta 359:27-45, (2005).
Leon et al., "Alterations inCholesterol RegulationContribute to the Production of IntratumoralAndrogensDuring ProgressiontoCastration-Resistant Prostate Cancer in aMouseXenograftModel," The Prostate 70:390-400 (2010).
Wang et al.,"Paper spray for direct analysis of complex mixtures using mass spectrometry." Angew. Chem. Int. Ed. 49:877-880 (2010).
Shi,et al. "Effective repair of traumatically injured spinal cord by nanoscale block copolymer micelles." Nat. Nanotechnol. 5:80-87, (2010).
Zhou X, Mao J, Ai J, Deng Y, Roth MR, et al. (2012) Identification of Plasma Lipid Biomarkers for Prostate Cancer by Lipidomics and Bioinformatics. PLoS One 7(11): e48889. doi:10.1371/journal.pone. 0048889.
Antails, et al. "Acyl-CoA:cholesterol acyk transferase (ACAT1) is highly expressed in humna breast cancer cell lines and ACAT inhibition reduces proliferation, " http://www.fasebj.org/cgi/content/meeting_abstract/22/2_MeetingAbstracts/709.
Antalis et al., "Lipoproteins and Cancer", http://dx.doi.org/10.5772/50989.
Chen et al. "High-efficiency 1598.5-nm third Stokes Raman laser based on barium nitrate crystal," Chin. Opt. Lett., 2006, 04(07): pp. 404-406-3.
Chyba et al. "Development of a Portable, Ground-based Ozone Lidar Instrument for Tropospheric Ozone . . . ," Final Report, NASA Research Grant NAG-Jan. 1949, Jul. 1, 1997-Jun. 30, 1999.
Lee, H. et al., "Birefringence compensation in a barium nitrate Raman laser," CLEO Pacfic Rim 99,ThG4, pp. 638-639.
Lux, et al. "Barium Nitrate Raman Laser for Co2 Detection," CLEO Technical Digest, OSA 2012.
Simons, et al. "Small-scale, all-solid-state, frequency-doubled intracavity . . . ," Optics Communications 229 (2004) 305-310.
Hou, et al, "Thin Polymer etalon arrays for high-resolution photoacoustic imaging," J Biomed Opt. 2008 ; 13(6): 064033. doi:10. 1117/1.3042260.
Wang, Han-Wei, "Label-free Bond-Selective Imaging by Listening to Vibrationally Excited Molecules," PRL 106, (2011) pp. 238106-1-238106-4.
International Search Report and Written Opinion, issued in PCT/US13/23095, mailed on Jun. 12, 2013.
International Preliminary Report on Patentability issued in PCT/US2013/023095 on Aug. 14, 2014.
Hartsuiker, L., "Microspectric Characterisation of Gold Nanorods for Cancer Cell Detection," 2011. Ph.D. Dissertation, pp. 1-172.
Yakolev VW et al., "Montioring Stimulated Ramam Scattering with Photoacoustic Detection," OPt. Lett. Apr. 1, 2011, vol. 36, No. 7, pp. 1233-1235.
Koljenovic, S. et al. "Towards Clinico-Pathological application of Ramam Spectroscopy: Detection of Meningioma in Dura Mater by Raman Spectroscopy," OPtima Grafische Communicatie, Rotterdam, The Netherlands 2008, pp. 45-62.
Hawi, SR. et al. "Raman Microspectroscopyof Intracellular Cholesterol Crystals in Cultured Bovine Coronary Artery Endothelial Cells." Journal of Lipid Reseach, 1997, vol. 38, pp. 1591-1597.
American Cancer Society, Testing Biopsy and Cytology Specimans for Cancer. Mar. 24, 2010.
Remy, C. et al. "Evidence that Mobile Lipids Detected in Rat Brain Glioma by 1H Nuclear Magnetic Resonance Correspond to Lipid Droplets." Cancer Research. Feb. 1, 1997, vol. 57. pp. 407-414.

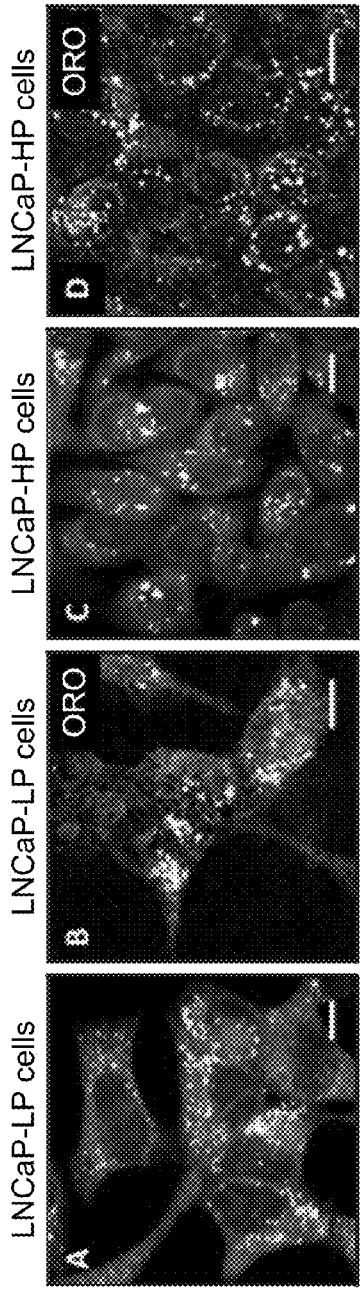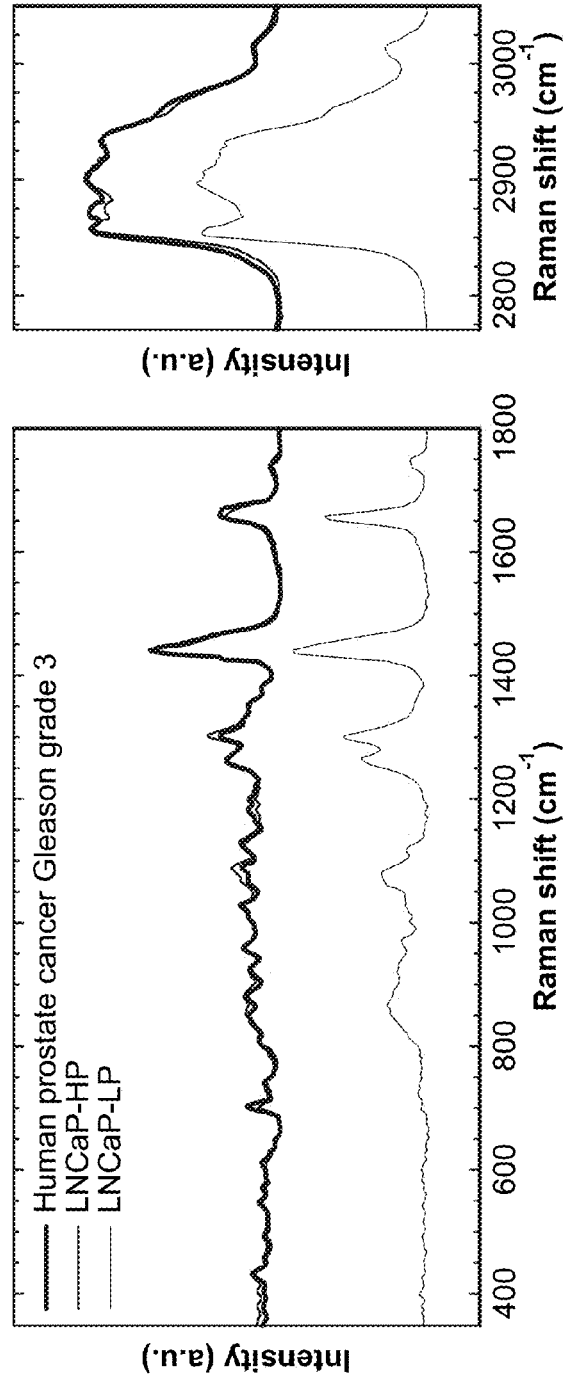

Avasimibe
(ACAT inhibitor)

LDL uptake

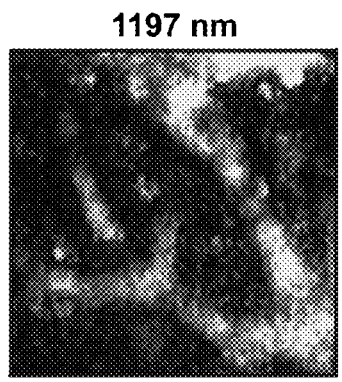
FIG. 54A
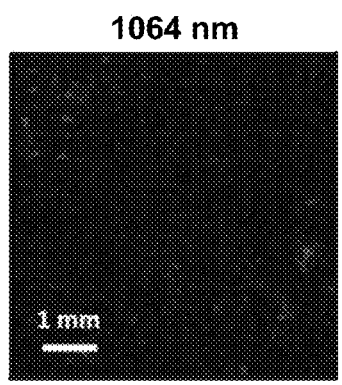
FIG. 54B
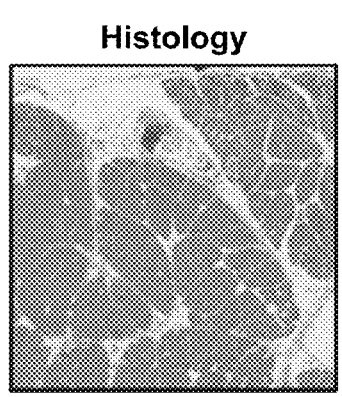
FIG. 54C
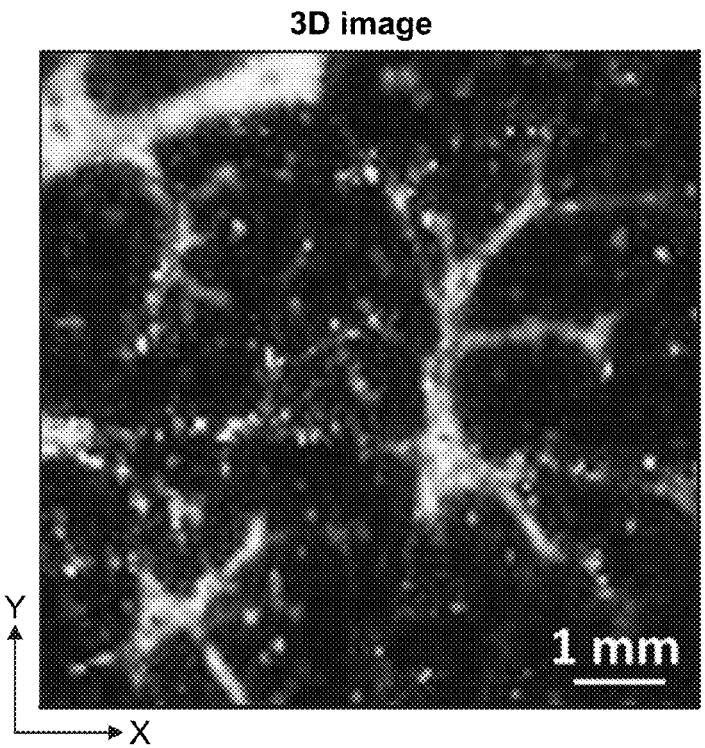
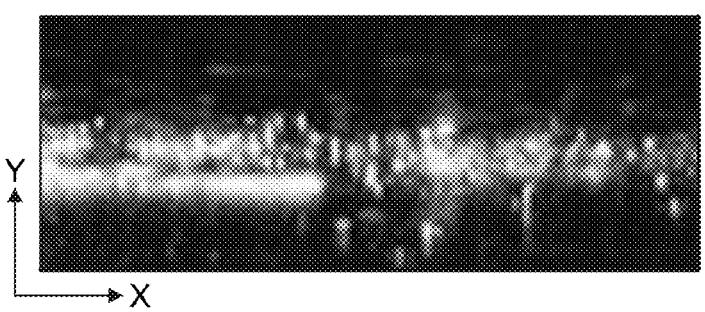
FIG. 54D

METHODS FOR DETERMINING AGGRESSIVENESS OF A CANCER AND TREATMENT THEREOF

GOVERNMENT SUPPORT

This invention was made with government support under EB015901 awarded by National Institutes of Health. The government has certain rights in the invention.

RELATED APPLICATION

The present application is a 35 U.S.C. §371 national phase patent application of PCT/US 13/23095, filed Jan. 25, 2013, which claims the benefit of and priority to U.S. provisional application Ser. No. 61/592,819, filed Jan. 31, 2012, and U.S. provisional application Ser. No. 61/753,007, filed Jan. 16, 2013, the content of each of which is incorporated by reference herein in its entirety.

FIELD OF THE INVENTION

The invention generally relates to methods for determining aggressiveness of a cancer and treatment thereof.

BACKGROUND

Cancer (neoplasia) is characterized by deregulated cell growth and cell division. Cancers include carcinomas that are tumors arising in a tissue originating from endoderm or exoderm, and sarcomas that originate from mesoderm (Darnell, J., Molecular Cell Biology, Third Ed., W.H. Freeman, NY, 1990). Solid tumors are found in nervous system, breast, retina, lung, skin, kidney, liver, pancreas, genito-urinary tract, gastrointestinal tract, cancers of bone, and cancers of hematopoietic origin including various types of leukemia and lymphoma.

A primary effort in cancer research is directed toward early detection of malignancy, and a reliable assessment of the severity of that malignancy. That has included an emphasis on determining the presence of precancerous or cancerous cells. Those cells are typically analyzed, for example, for protein markers, for nucleic acid markers, or for chromosomal abnormalities.

A problem with those methods is that they focus solely on genetic aspects of cancer by looking for some form of genomic instability. Those methods overlook non-genetic factors that may play a role in cancer development and aggressiveness. Accordingly, such methods have limited diagnostic value for a large percentage of the population due to the fact that a diagnosis is based upon using only known genomic instabilities and does not account for cancer causing genomic instabilities that have not previously been associated with a particular type of cancer.

SUMMARY

The invention provides methods that focus on non-genetic factors that are involved in cancer development and aggressiveness. Methods of the invention look at the role of lipids, particularly intracellular storage of lipid droplets, in cancer development and aggressiveness. The invention recognizes that the chemical make-up within a lipid droplet is determinative of aggressiveness of a cancer. Aspects of the invention are accomplished by conducting an assay on a lipid droplet in order to detect an amount of a biomarker within the lipid droplet. A determination of aggressiveness of a cancer is then made based upon the amount of the biomarker within the lipid droplet. Methods of the invention allow for early detection of malignancy, and a reliable assessment of the severity of that malignancy.

Methods of the invention may use any biomarker within a lipid droplet. Typically, a lipid droplet includes triacylglycerols and sterol esters, and methods of the invention may analyze amounts of any one or more of those biomarkers in order to determine aggressiveness of a cancer. In certain embodiments, the biomarker is cholesteryl ester, and an increased amount of cholesteryl ester within the lipid droplet is determinative of aggressiveness of a cancer. Methods of the invention may be used to determine the aggressiveness of any cancer. Exemplary cancers include prostate cancer, pancreatic cancer, breast cancer, colon cancer, and brain cancer.

Any assay that is able to analyze contents of a lipid droplet may be used with methods of the invention. The assays may be an in vivo assay or an in vitro assay. In embodiments in which the assay is an in vivo assay, then the assay is preferably carried out using a vibration-based spectroscopic imaging apparatus. In this manner, the assay may be conducted without the use of optical labels or dyes, i.e., a label-free assay. In a particular embodiment, the assay performs a vibration-based spectroscopic imaging of cholesteryl ester within the lipid droplet. In this embodiment, the assay detects characteristic bands for a cholesterol ring at 428 $cm^{-1}$, 538 $cm^{-1}$, 614 $cm^{-1}$, and 702 $cm^{-1}$, an ester bond at 1742 $cm^{-1}$, a $CH_2$ deformation at 1448 $cm^{-1}$, a cholesterol-specific C—H stretch vibration at 2860 $cm^{-1}$, and the second overtone of C—H vibration around 1200 nm.

In certain embodiments, the vibration-based spectroscopic imaging apparatus includes a light source, a hollow body coupled to the light source such that light is transmitted through the hollow body, and a detector. The apparatus is generally configured so that light from the light source is directed onto a tissue and the detector is coupled to the apparatus such that it can detect a spectroscopic signal generated from tissue that has been excited by the light source. In certain embodiments, the detector is an ultrasound transducer. The apparatus may further include an optical diffuser coupled to the body and positioned to diffuse the light from the light source prior to the light impinging on the tissue.

Generally, the light source is configured to output a signal that can non-invasively and selectively cause overtone excitation of molecules based on a predetermined chemical bond. Any light source known in the art may be used. Exemplary light sources include a narrow line width tunable laser source or a superluminescent diode source. Examples of narrow line width tunable laser sources include, but are not limited to, lasers having a Bragg diffraction grating or a deformable membrane, lasers having a spectral dispersion component (e.g., a prism), or Fabry-Pérot based tuning laser. In certain embodiments, the light source is a laser having a barium nitrate amplifier and is configured to output a signal at 1197 nm.

Generally, the in vitro assay is conducted on one or more intact cells. In some embodiments, the in vitro assay is carried out using a multimodal nonlinear optical microscopy device. While not required, it may be desirable to enrich the lipid droplets prior to conducting the assay. Accordingly, certain embodiments involve obtaining a sample from a patient suspected to have a cancer, and enriching for lipid droplets from the sample prior to conducting the assay.

Methods of the invention may also involve providing a course of treatment to the patient based on results of the determining step. The treatment plan will be based on the aggressiveness of the cancer. For example, the course of treatment may involve continued monitoring or administration of an agent that blocks storage of the biomarker within the lipid droplet. Exemplary agents include fatty acid synthase inhibitors, cholesterol acyltransferase (ACAT) inhibitors, low-density lipoprotein (LDL) reducing compounds, and HMG-CoA reductase inhibitors. In certain embodiments, the agent blocks storage of cholesteryl ester in a lipid droplet. Generally, the agent is formulated with a pharmaceutically acceptable carrier. The agent may also be provided as a unitary dose.

BRIEF DESCRIPTION OF THE DRAWINGS

FIG. 11 shows an accumulation of cholesterol ester in lipid droplets during the progression of human prostate cancer cell LNCaP from androgen responsive to hormone refractory state. LP=low passage; HP=high passage; and Scale bars=20 µm. Panels A and C show cells under an SRL microscope. Panels B and D show cells labeled by oil red O. Panels E and F show the Raman spectra of the lipid droplets.

FIG. 54, Panels A-D show photoacoustic imaging of intramuscular fat performed with the Raman laser. Panel A shows en face maximum intensity projection photoacoustic image of intramuscular fat sample with 1197 nm excitation. Panel B shows en face maximum intensity projection photoacoustic image of intramuscular fat sample with 1064 nm excitation. Panel C shows histological evaluation of the same intramuscular fat sample. Panel D shows three-dimensional photoacoustic image of a separate intramuscular fat sample. Pulse energy: 60 μJ. Image size: 120×120 pixels.

DETAILED DESCRIPTION

Figure 1:
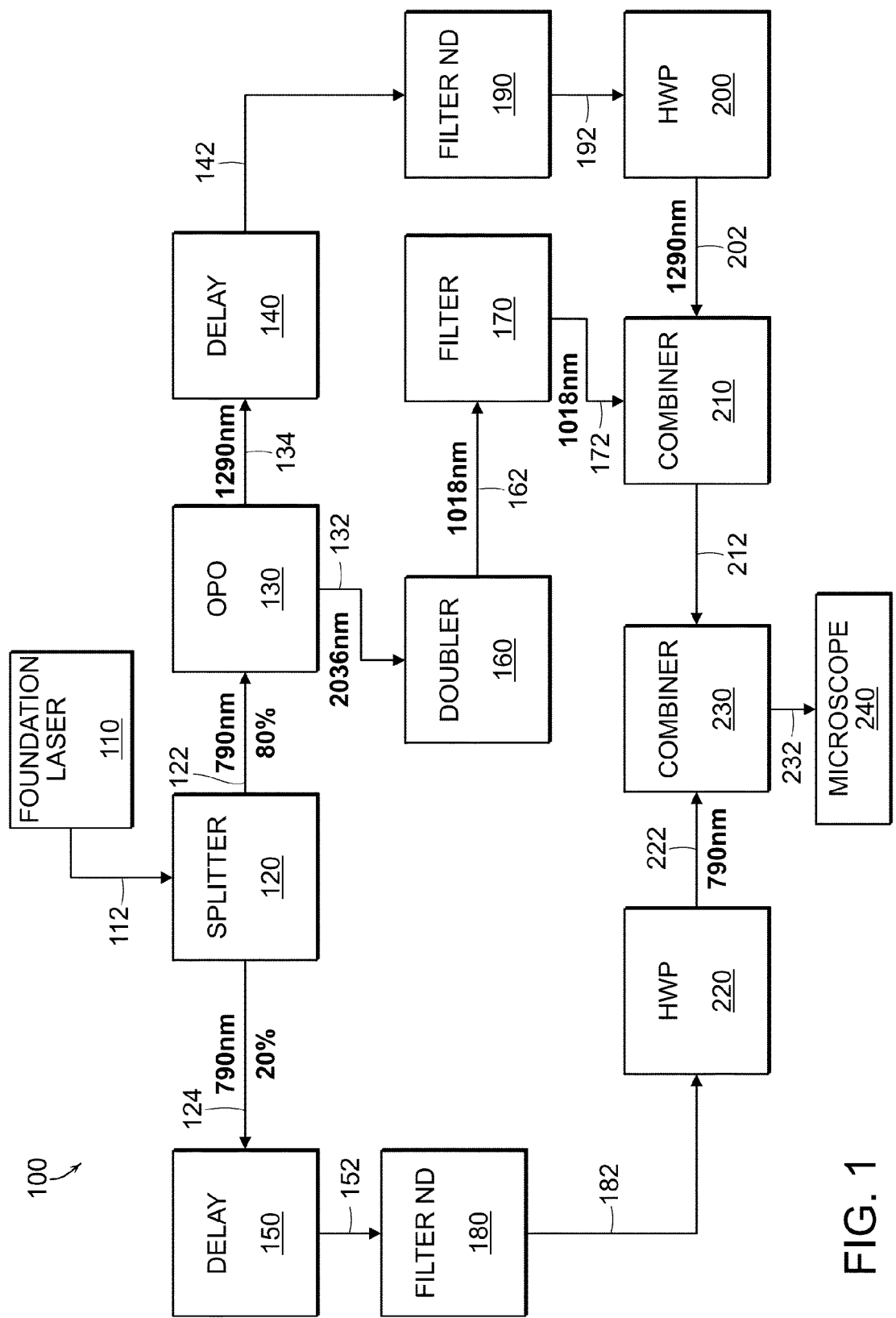
FIG. 1 is a schematic of multimodal nonlinear optical microscopy device.

The invention generally relates to methods for determining aggressiveness of a cancer and treatment thereof. In certain embodiments, methods of the invention involve conducting an assay on a lipid droplet in order to detect an amount of a biomarker within the lipid droplet, and determining aggressiveness of a cancer based upon the amount of the biomarker within the lipid droplet.

A lipid droplet (also known as a lipid body, lipid globule, lipid particle, or oil body) is a ubiquitous fat storage organelle that store triglycerides and sterols for energy production and as biosynthetic precursors. Lipid droplets typically include neutral lipids in the form of triacylglycerols, cholesteryl esters, or retinyl esters (biomarkers within the lipid droplet) surrounded by a phospholipid monolayer. The surface of lipid droplets is adorned with proteins that serve structural and metabolic functions. Lipid droplets are further described for example in Guo et al. (J Cell Sci, 122:749-752, 2009), the content of which is incorporated by reference herein in its entirety.

Formation of a lipid droplet begins when fatty acids that are carried extracellularly by albumin and lipoproteins enter cells. Fatty acids are released from triacylglycerols in lipoproteins by lipoprotein lipase, and enter cells by passive diffusion facilitated by fatty-acid transport proteins or fatty-acid translocase. Fatty acids can also be synthesized de novo from carbohydrates in many cell types. Next, fatty acids enter a bioactive pool through conjugation to CoA, forming fatty acyl-CoA, in an energy-requiring reaction. Fatty acyl-CoA is used by glycerolipid-synthesis enzymes (glycerol-3-phosphate acyltransferase and sn-1-acylglycerol-3-phosphate acyltransferase) in the ER to ultimately generate diacylglycerols. Diacylglycerols are either converted to neutral lipids (triacylglycerols) by DGAT enzymes or enter phospholipid-synthesis pathways.

In contrast to fatty acids, sterols are primarily taken up into cells through endocytosis and lysosomal degradation of lipoproteins. Most cells can also synthesize sterols. Excess sterols are converted to sterol esters through conjugation with fatty acyl-CoA in a reaction that is catalyzed by sterol-O-acyltransferases (e.g. acyl-CoA:cholesterol acyltransferase) in the endoplasmic reticulum.

Thus, neutral lipids that are found in lipid droplet cores are synthesized in the endoplasmic reticulum. Without being limited by any particular theory or mechanism of action, the canonical model suggests that neutral lipids form a lens of oil in the endoplasmic reticulum bilayer that subsequently buds from the membrane (the ER-budding model), taking with it phospholipids from the cytosolic leaflet. Although the model has substantial support, this process has not been observed directly. In a variant of this model, the ER-domain model, lipid droplets remain connected to the endoplasmic reticulum and are lipid-containing protrusions of the endoplasmic reticulum membrane, forming a specialized endoplasmic reticulum domain.

Alternative models for lipid formation have been proposed. In the bicelle model, neutral lipids accumulate between the leaflets of the endoplasmic reticulum membrane but, instead of budding, nascent Lipid droplets are excised from the membrane, taking with them phospholipids from both the cytosolic and luminal leaflets. That model was suggested to explain how large unfolded proteins or viruses might escape from the endoplasmic reticulum lumen into the cytosol. In the vesicular-budding model, small bilayer vesicles that remain tethered to the endoplasmic reticulum membrane are used as a platform for making lipid droplets. Newly synthesized neutral lipids are pumped into the vesicle bilayer and fill the intermembrane space, eventually squeezing the vesicular lumen so that it becomes a small inclusion inside the lipid droplets.

In lipoprotein-producing cells, such as intestinal enterocytes or hepatocytes, neutral lipids can also be directed from the endoplasmic reticulum bilayer into the endoplasmic reticulum lumen to associate with apolipoprotein B for secretion.

The size of lipid droplets varies tremendously, with diameters ranging from as small as 20-40 nm to 100 µm (in white adipocytes). Additionally, lipid droplets can grow in size. Without be limited by any particular theory or mechanism of action, one possibility is that lipid droplets expand as single organelles. If lipid droplets remain attached to the endoplasmic reticulum, proteins and newly synthesized lipids could diffuse laterally to the lipid droplets. If lipid droplets are detached from the endoplasmic reticulum, those proteins and lipids must be transported to the lipid droplets, possibly via vesicular transport. Alternatively, neutral lipids in the core could be produced locally by enzymes, such as DGATs, that are targeted to the lipid droplet surface. In either scenario, the increase in volume of neutral lipids would need to be matched by a corresponding increase of phospholipids at the surface. In agreement with this notion, a key enzyme of phospholipid synthesis, CTP:phosphocholine cytidylyltransferase (CCT), is localized to lipid droplet surfaces during their growth.

Fusion of smaller Lipid droplets to form larger Lipid droplets is also likely to contribute to LD growth (e.g. Guo et al., 2008), and models that implicate SNARE proteins and motor proteins in LD fusion have been proposed (Boström et al., 2007; Olofsson et al., 2008). A fusion mechanism would alleviate the requirement for phospholipid synthesis during the growth of Lipid droplets, because the surface:volume ratio decreases with fusion.

Any assay that is able to analyze contents of a lipid droplet (e.g., triacylglycerols, cholesteryl esters, or retinyl esters within a lipid droplet) may be used with methods of the invention. The assay may be an in vivo assay or an in vitro assay. In certain embodiments, whether the assay is an in vivo assay or an in vitro assay, the assay is carried out using a vibration-based spectroscopic imaging apparatus. In this manner, the assay may be conducted without the use of optical labels or dyes, i.e., a label-free assay. Label free assays are useful for the invention because there are no specific optical labels for lipids. Additionally, fluorescent labels are too bulky and do not provide information about the composition inside a membrane domain or lipid droplet. Such challenges are overcome through label-free spectroscopic imaging apparatuses that rely on molecular vibration as contrast.

If an in vitro assay is employed, the in vitro assay is generally conducted on one or more intact cells. Accordingly, certain embodiments involve obtaining a sample from a patient suspected to have a cancer. The sample is typically a tissue or body fluid that is obtained in any clinically acceptable manner. A tissue is a mass of connected cells and/or extracellular matrix material, e.g. skin tissue, nasal passage tissue, CNS tissue, neural tissue, eye tissue, liver tissue, kidney tissue, prostate tissue, pancreatic tissue, lung tissue, mammary gland tissue, breast tissue, brain tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed. In particular embodiments, the sample is prostate tissue, breast tissue, brain tissue, pancreatic tissue, or colon tissue, typically obtained from a biopsy.

While not required, it may be desirable to enrich for lipid droplets from the sample prior to conducting the assay. Enrichment techniques are known in the art. In one embodiment, flow cytometry techniques can also be used to enrich for lipid droplets from a sample. The use of flow cytometry for separating a target from a sample is described for example in Herzenberg et al. (PNAS 76:1453-1455, 1979); Bianchi et al., (PNAS 87:3279-3283, 1990); and Bruch et al., (Prenatal Diagnosis 11:787-798, 1991), and Saunders et al. (U.S. Pat. No. 5,432,054), the content of each of which is incorporated by reference herein in its entirety.

Further, an agent that stabilizes cell membranes may be added to the sample to reduce cell lysis including but not limited to aldehydes, urea formaldehyde, phenol formaldehyde, DMAE (dimethylaminoethanol), high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, *ginkgo biloba* extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

In certain embodiments, the in vitro assay is carried out using a multimodal nonlinear optical microscopy device that utilizes coherent anti-Stokes Raman scattering (CARS). Such devices are described for example in Cheng et al. (U.S. patent application number 2011/0261349) and Le et al. (BMC Cancer, 9(42): 1-14, 2009), the content of each of which is incorporated by reference herein in its entirety. The assay is used to detect an amount of a biomarker within a lipid droplet. In certain embodiments the biomarker is cholesteryl ester.

Coherent anti-Stokes Raman scattering (CARS) microscopy is a four wave mixing process where two synchronized lasers, pump and Stokes, are tightly focused into a diffraction-limited focal volume. The interaction of the pump field at frequency $\omega p$ and the Stokes field at frequency $\omega S$ with the medium generates an anti-Stokes field at frequency $2\omega p-\omega S$. CARS signal is significantly enhanced when $\omega p-\omega S$ matches a Raman-active vibrational band. Furthermore, the intrinsic coherent property allows CARS signal to increase quadratically with respect to the number of molecular vibrations in the focal volume. Such property renders CARS highly sensitive to lipid-rich structures when $\omega p-\omega S$ matches the symmetric $CH_2$ stretch vibration at 2840 $cm^{-1}$. An additional unique advantage of CARS microscopy is its intrinsic capability for multimodal imaging. A typical CARS microscope with picosecond pulse excitation is capable of simultaneous CARS, sum frequency generation (SFG), and two-photon excitation fluorescence (TPEF) imaging. Moreover, confocal Raman micro-spectroscopy can be performed on such a CARS microscope to generate a spectrum of any objects seen in a CARS image (Slipchenko et al. Journal of Physical Chemistry 2009). With the invention, CARS microscopy is employed to detect an amount of a biomarker (e.g., cholesteryl ester) within the lipid droplet.

Referring to FIG. 1, a block diagram for a nonlinear multimodal platform for optical microscopy and microspectroscopy 100 is provided. The system 100 of FIG. 1 includes a foundation laser beam generator 110, a splitter 120, an Optical Parametric Oscillator (OPO) 130, a delay element 140, a delay element 150, a frequency doubler 160, and a filter 170. The system 100 further includes a Neutral Density (ND) filter 180, another ND filter 190, a Half Wave Plate (HWP) 200, a combiner 210, another HWP 220, and another combiner 230. The system 100 also includes a microscope 240.

The foundation laser 110 is operable coupled to the splitter 120 which splits the laser beam into two outputs 122 and 124 of varying powers. The output 122 is operably divided by the OPO 130 into two output laser beams of varying wavelengths 132 and 134. The output 132 is processed by a frequency doubler 160 which produces the output 162. The output 162 is filtered by the filter 170, which provides an output 172. Also, the output 124 is delayed by the delay element 140 to produce an output 142. The output 142 is filtered by the ND filter 190 which produces the output 192. The output 192 is operably coupled to the HWP 200 to produce an output 202. The outputs 172 and 202 are combined by the combiner 210 to produce a combination laser beam 212. Also, the output 124 is delayed by the delay element 150 to produce an output 152. The output 152 is filtered by the ND filter 180 to produce an output 182. The output 182 is operably coupled to the HWP block 220 to produce an output 222. The combination laser beam 212 and the output 222 are combined to produce a combination laser beam 232 which is an input to the microscope 240.

The platform of FIG. 1 provides capabilities for Coherent Anti-stokes Raman Scattering (CARS), Polarization sensitive CARS (PCARS), Second Harmonic Generation (SHG), Third Harmonic Generation (THG), and Two-Phonon Fluorescence (TPF) imaging modalities. A femtosecond (fs) laser 110 provides a foundation laser source for the above modalities. The terms foundation and pump laser are used interchangeably and are intended to convey the same concept. An example of the fs laser 110 is a Mai Tai laser from Spectra-Physics which provides an output laser 112 at a wavelength of 790 nm at 3.0 W. The splitter 120 is provided to split the output 112 of the fs laser source 110 into two beams. The beam 122 has about 80% of the power of the output 112 of the laser source 110 and the other beam 124 has about 20%. The 80% beam 122 is provided as an input to an Optical Parametric Oscillator (OPO) 130 to generate two outputs 132 and 134 with lower frequencies than the input. The sum of the frequencies of the outputs 132 and 134 is equal to the frequency of the input 122. The input 122 of the OPO 130 is commonly referred to as the "pump" while one output 132 is commonly referred to as the "idler" and the other output 134 is commonly referred to as the "signal." The idler output 132 has a wavelength of 2036 nm and the signal output 134 has a wavelength of 1290. An example of the OPO 130 is an Opal-BB from Spectra-Physics.

For synchronization purposes, the signal output 134 and the 20% output of the splitter 124 are passed through optical delay elements 140 and 150, respectively. The optical delay elements 140 and 150 provide delayed outputs 142 and 152, respectively. The idler output 132 is provided as an input to the frequency doubler 160. The frequency doubler 160 can be a Periodically Poled Lithium Niobate (PPLN) crystal-based doubler. The frequency doubler 160 provides an output 162 which has a wavelength 1018 nm. The output 162 is also referred to as the Stokes laser. The output 162 is filtered by a colored glass filter 170 which provides the filtered output 172. An example of the filter 170 is RG 850 manufactured by Schott. The delayed 20% beam 152 is also filtered by the neutral density filter 180 which provides the filtered output 182. Further, the delayed signal 142 output from the delay element 140 is filtered by the neutral density filter 190 which produces the filtered output 192. The filtered output 192 is applied to the HWP 200 for altering the polarization state of the filtered output 192 which travels through the half wave plate 200, i.e., for polarization rotation to be used in PCARS. The half wave plate 200 produces an output 202. The filtered output 172 and the output 202 are combined by the combiner 210 to generate a collinearly combined combination laser beam 212 of 1290 nm and 1080 nm beams. The filtered output 182 is also applied to the HWP 220 which provides an output 222. The combination laser beam 212 and the output 222 are combined by the combiner 230 to produce the collinearly generated combination laser beam 232. The default polarizations of 790 nm, 1018 nm and 1290 nm beams are vertical before the microscope. The combination laser beam 232 is used as an input for platform microscope such as a flow view 1000 confocal microscope manufactured by Olympus.

A 60×/CARS water objective with a 1.2 numerical aperture (1-U2B893IR, Olympus) may be used to focus all laser beams into a specimen. Backward signal may be collected by the same objective and detected by either embedded internal spectral detectors or an external detector. An example of an internal detector is a Grating spectrometer with a photomultiplier tube (PMT). An example of an External detector is a R7683 from Hamamatsu Photonics. Forward signal may be collected by an air condenser and detected by a second external PMT detector. An example of an air condenser is an Olympus 0.55 NA air condenser. Proper bandpass filters are used to selectively transmit a certain NLO signal. The acquisition time for each frame of 512×512 pixels is 1.1 seconds.

For CARS imaging of lipid droplets and Raman analysis of biomarkers within lipid droplets, the pump laser ($\omega_1$) at 707 nm (14140 cm$^{-1}$) and the Stokes laser ($\omega_2$) at 885 nm (11300 cm$^{-1}$) maps individual lipid droplets based on the resonant signal from CH$_2$ symmetric stretch vibration at 2840 cm$^{-1}$. The confocal Raman signal generated by the pump laser detects characteristic bands for a cholesterol ring at 428 cm$^{-1}$, 538 cm$^{-1}$, 614 cm$^{-1}$, and 702 cm$^{-1}$, an ester bond at 1742 cm$^{-1}$, aCH$_2$ deformation band at 1448 cm$^{-1}$, and a cholesterol-specific C—H stretch vibration at 2860 cm$^{-1}$. CARS signal are detected by external detectors with the 650/45 nm bandpass filter or by an internal spectral detector with the 620-670 nm filter. Images may be analyzed using FluoView software (Olympus America Inc., PA) and Image J (NIH).

In certain embodiments, the in vitro assay is carried out using a vibrational photoacoustic imaging apparatus. Such an apparatus may also be used for in vivo assays. The apparatus generally includes a light source, a hollow body coupled to the light source such that light is transmitted through the hollow body, and a detector. The apparatus is typically configured such that light from the light source is directed onto a tissue and the detector is coupled to the apparatus such that it can detect a spectroscopic signal generated from tissue that has been excited by the light source. An exemplary device is described for example in Cheng et al. (International publication number WO 2012/024687), the content of which is incorporated by reference herein in its entirety. The device operates based on overtone excitation of molecular vibration targeting specific chemical bonds along with acoustic detection of pressure waves that are generated in a biological tissue as a result of the overtone excitation. The apparatus provides label-free (unstained and untagged) non-invasive or minimally invasive imaging that does not damage tissues during characterization of biomarkers within lipid droplets. Typically, a pulsed, wavelength-tunable, monochromatic radiation is directed into a sample. The wavelength of the radiation is adjusted to match the overtone vibrational frequency of a molecule at near-infrared region. Vibrational absorption of the incident radiation and subsequent conversion of the vibrational energy into heat generates a pressure transient inside a sample, thereby producing a detectable acoustic signal having molecule-specific information.

A photoacoustic effect takes place when radiation is absorbed by a tissue sample. The absorbed energy is converted to heat which then causes local thermal expansion through the thermal elastic process. The thermal expansion thereafter generates pressure wave transient that propagates through the sample tissue as an acoustic wave and can be detected by one or more transducers. Information obtained from the amplitude and the time-of-flight of the acoustic waves can be used to construct an image of the absorbing structure of tissues. Different biological tissues have different photoacoustic responses because of differences in absorption coefficient, thermal elasticity, size of absorber, etc. It should also be appreciated that different acoustic waves initiated by different structures arrive at the transducers at different times. This is because of flight times of these waves differ based on the depths of the structures, as the ultrasound waves propagate at the speed of sound within a tissue. According to one embodiment, a tunable nanosecond (ns) laser is used to induce overtone vibration absorption of selected molecules and more particularly, molecules with selected chemical bonds. The generated ultrasound waves is detected by a transducer and recorded through amplifier(s) and custom built data acquisition devices.

Overtone absorption is an important principle of near-infrared spectroscopy that measures bulk absorbance or reflectance of samples. According to the anharmonicity theory, the frequency of an overtone band is described by $$\Omega_{n-1}=\Omega_0 n - \chi \Omega_0 (n+n^2),$$

where $\Omega_0$ is the frequency of the fundamental vibration, $\chi$ is the anharmonicity, and n=2, 3, . . . represent the first, second, and so on, overtones.

Figure 2:
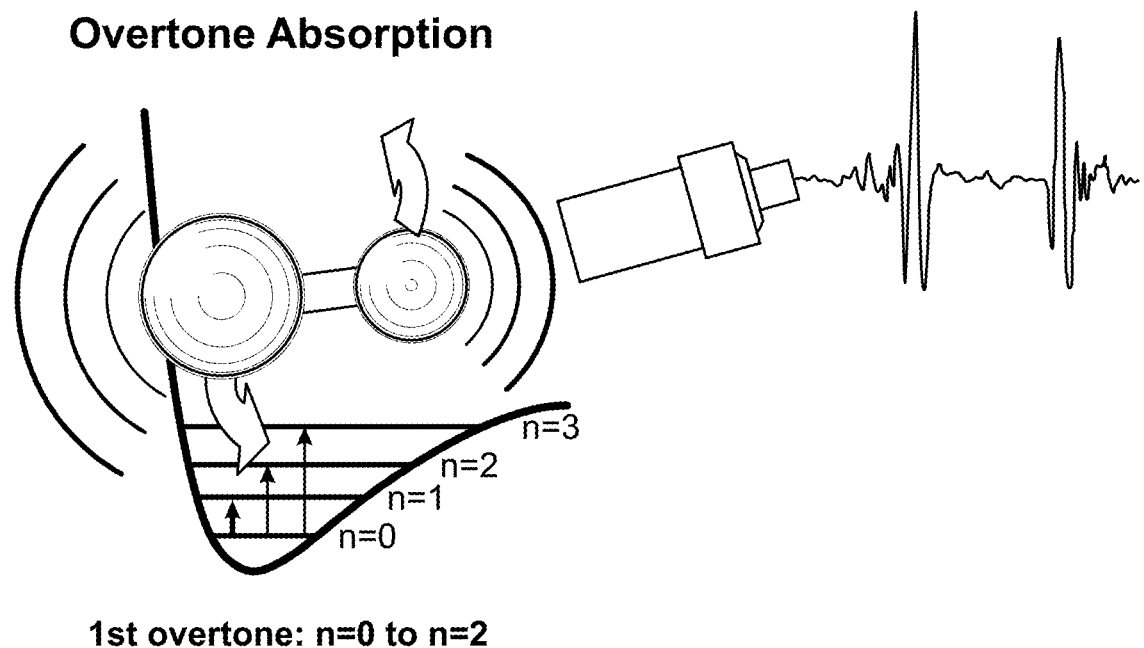
FIG. 2 depicts a diagram of the 1st (2v) and 2nd (3v) overtone absorption of a molecule.

Referring to FIG. 2, a diagram representation of overtone excitation is depicted. Using the near-infrared spectroscopic approach, molecular spectra in chemical and biological samples can be excited according to radiation signals representing the overall overtone absorption and the elastic scattering in a sample. The spectral information can also be retrieved to perform a molecular scan or chemogram of biological tissues, e.g. biomarkers within lipid droplets. The bulk measurement of absorbance or reflectance, however, obscures depth information. The elastic scattering further compromises the imaging potential of near-infrared spectroscopy. Notably, most of the second overtone frequencies of molecules of interest are located in the near-infrared region from 700 to 1300 nm, where the background tissue is minimally absorbing. Within this spectral region, overtone vibrational absorption provides opportunities to generate a chemically selective photoacoustic transient in a biological structure.

Figure 3:
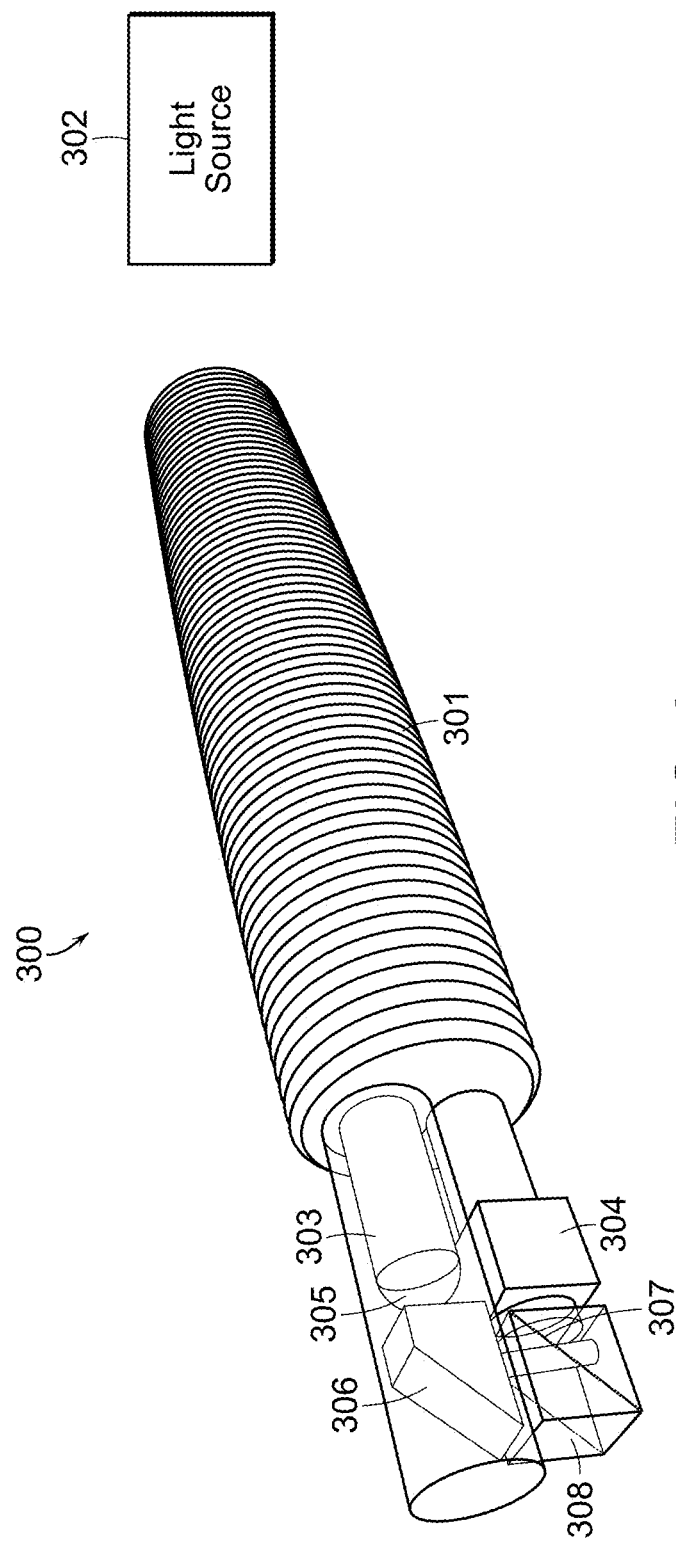
FIG. 3 is a schematic of an exemplary configuration of an apparatus of the invention.

FIG. 3 shows an exemplary embodiment of a vibrational photoacoustic imaging apparatus 300. The apparatus includes a hollow body 301, which is generally a catheter. The catheter and catheter body are configured for intraluminal introduction to the target body lumen. The dimensions and other physical characteristics of the catheter bodies will vary significantly depending on the body lumen that is to be accessed. In the exemplary case of an endoscope intended for rectal introduction, the proximal portions of the catheter bodies will typically be very flexible. In other embodiments, the catheter is suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

Apparatus 300 also includes at least one light source 302. Exemplary light sources include a narrow line width tunable laser source or a superluminescent diode source. Examples of narrow line width tunable laser sources include, but are not limited to, lasers having a Bragg diffraction grating or a deformable membrane, lasers having a spectral dispersion component (e.g., a prism), or Fabry-Pérot based tuning laser.

Figure 7:
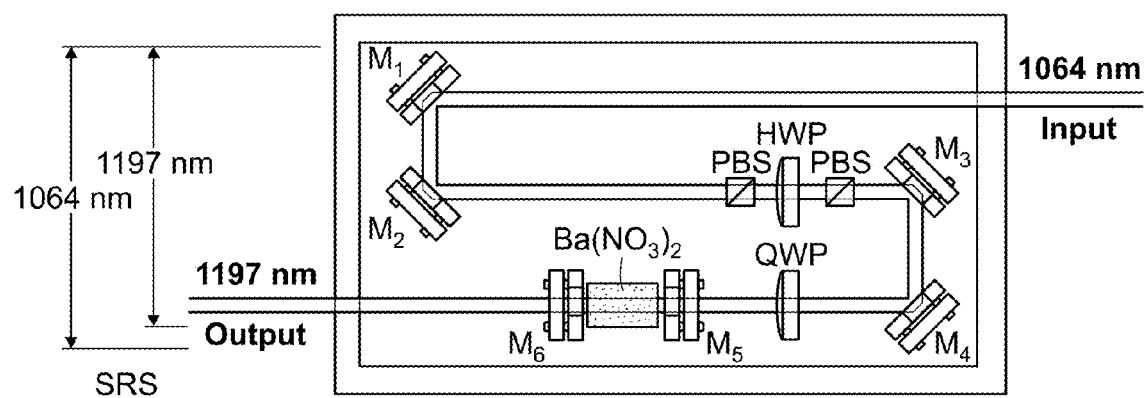
FIG. 7 is a schematic of an exemplary light source.

FIG. 7 shows an exemplary light source for use with apparatuses of the invention. The light source in FIG. 7 is a Raman laser that shifts an Nd:YAG laser wavelength from 1064 nm to 1197 nm based on the simulated Raman scattering process. With an input energy of 290 mJ, 105 mJ at 1197 nm was obtained. The laser in FIG. 7 was constructed with $Ba(NO_3)_2$ as the gain medium and generated energy over 100 mJ per pulse. An Nd:YAG laser (Surelite III, Continuum) providing 10-Hz, 1064 nm pulses with duration of 5 ns and 1.0 J pulse energy was used to pump the Raman laser. A $Ba(NO_3)_2$ crystal of $8 \times 8 \times 80$ mm$^3$ was placed between two mirrors to form a resonator. Anti-reflection (AR) material was coated on the front and the rear side of the crystal for maximum transmission at 1064 and 1197 nm. The cavity mirror $M_5$ was coated with high reflectivity (HR) at 1197 nm. The output coupler $M_6$ was coated for HR at 1064 nm and 40% transmission at 1197 nm. The input pump laser beam at 1064 nm entered the laser cavity after passing through a half wave plate (HWP) and a polarizing beam splitter (PBS). The HWP and PBS combination controlled the pulse energy into the crystal.

The light source 302 is coupled to the hollow body 301 such that light 307 is transmitted through the hollow body. In certain embodiments, the light source 302 is housed within the body 301. In other embodiments, the light source 302 is outside of the hollow body 301. In either configuration, light 307 from the light source 302 will generally travel through at least one optical fiber 303. The basic structure of a generic optical fiber generally consists of layered glass cylinders. There is a central cylinder called the core. Surrounding this is a cylindrical shell of glass, possibly multilayered, called the cladding. This cylinder is surrounded by some form of protective jacket, usually of plastic (such as acrylate). For protection from the environment and more mechanical strength than jackets alone provide, fibers are commonly incorporated into cables. Typical cables have a polyethylene sheath that encases the fibers within a strength member such as steel or Kevlar strands.

Apparatus 300 also includes a detector 304. In certain embodiments, the detector 304 is an ultrasound transducer. Ultrasound transducers are well known in the art and any ultrasound transducer may be used with apparatuses of the invention. Ultrasound transducers are described for example in Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et al., U.S. Pat. No. 5,373,845, Seward et al., Mayo Clinic Proceedings 71(7):629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et al., U.S. Pat. No. 5,183,048, Eberle et al., U.S. Pat. No. 5,167,233, Eberle et al., U.S. Pat. No. 4,917,097, Eberle et al., U.S. Pat. No. 5,135,486, and other references well known in the art relating to intraluminal ultrasound devices and modalities. Typically, the detector is acoustically coupled to the light source by acoustic coupler 308.

Apparatus 300 is configured such that light 307 from the light source 302 is directed onto a tissue and the detector 304 is coupled to the apparatus 300 such that it can detect a spectroscopic signal generated from tissue that has been excited by the light source 302. An exemplary configuration is shown in FIG. 3. In that configuration, light 307 from the light source 302 is directed down an optical fiber within hollow body 301 until it reaches lens 305 and prism 306. At that time, the light 307 is redirected 90° and through an optically transparent portion of the body 301 so that it impinges on tissue. The 90° direction is only exemplary and the light 307 can be redirected at any desired angle.

Additionally, the redirection of the light 307 shown in FIG. 3 is only exemplary. Any way of redirecting light may be used in the described embodiment. For example, a blazed Fiber Bragg Grating within the optical fiber may be used to redirect the light. A blazed Bragg grating includes obliquely impressed index changes that are at a nonperpendicular angle to the longitudinal axis of the optical fiber 303. A standard unblazed Fiber Bragg Grating partially or substantially fully reflects optical energy of a specific wavelength traveling down the axis of the fiber core of an optical fiber back up the same axis. A blazed Fiber Bragg Grating reflects that optical energy away from the longitudinal axis of the optical fiber. For a particular combination of blaze angle and optical wavelength, the optical energy will leave the blazed Fiber Bragg Grating substantially normal (i.e., perpendicular) to the longitudinal axis of the optical fiber.

In this embodiment, the detector 304 is position immediately adjacent the optically transparent portion 307. Vibrational absorption of the incident radiation from the light source 302 and subsequent conversion of the vibrational energy into heat generates a pressure transient inside a sample, thereby producing a detectable acoustic signal having molecule-specific information that is detected by the detector 304.

Figure 4:
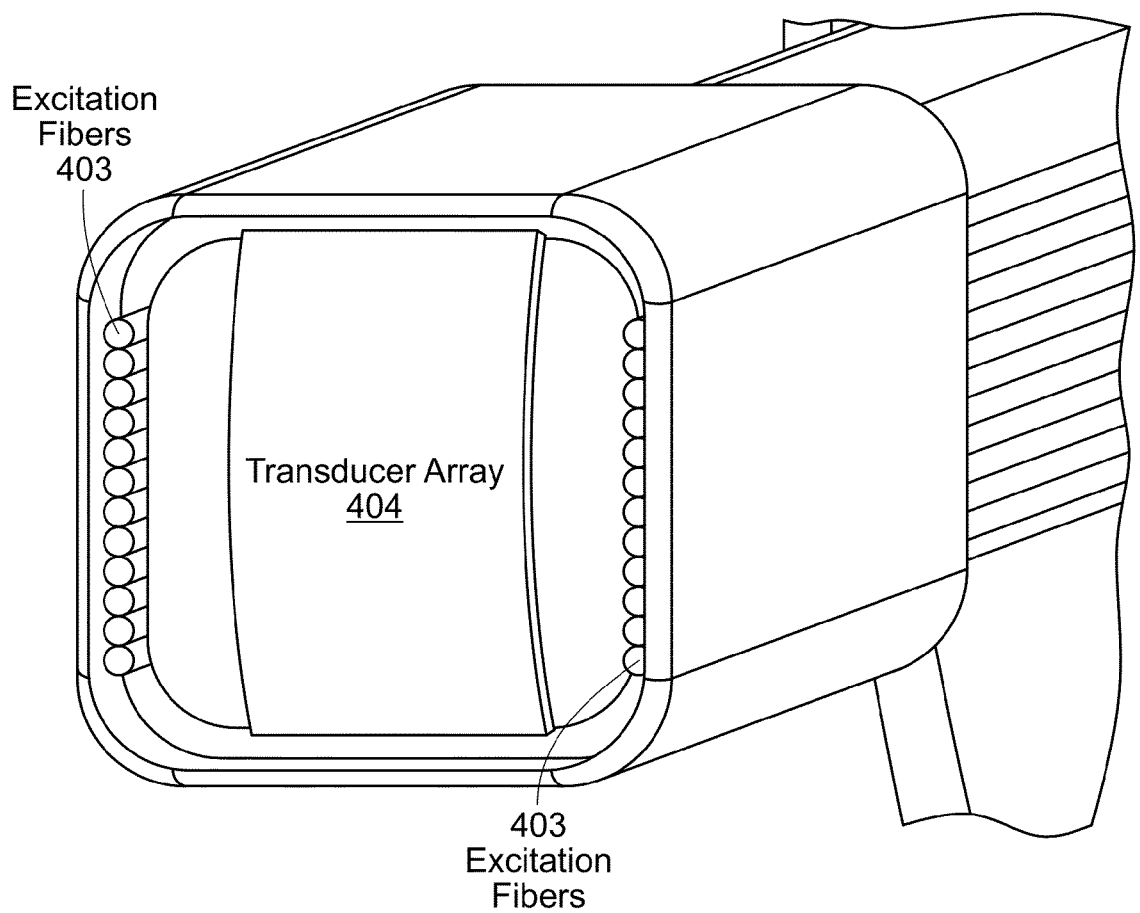
FIG. 4 is a schematic of another exemplary configuration of an apparatus of the invention.

Another exemplary configuration is shown in FIG. 4. In that configuration, two arrays of optical fibers 403 are arranged on either side of the detector 404 such that the detector 404 is between the arrays of optical fibers. For exemplary purposes, the detector is shown as an array of ultrasound transducers. In this configuration, the detector 404 and the optical fibers look straight ahead, such that the light from the light source is not redirected prior to exiting the optical fibers. Such a configuration allows for forward looking imaging. In certain embodiments, each fiber is slightly bent at the endpoints to facilitate the illumination of object towards the plane facing the center of the transducer array. A curved array transducer (C9-5ec, Philips Healthcare) with radius of curvature of 8 mm, a field of view of 150° and a frequency range of 5 to 9 MHz may be used to acquire the signals from the tissue. For each position of the endoscope, two images may be acquired sequentially at 1197 nm and 1064 nm. The two images are compared to remove the non-vibration contrast. The data is acquired in real time and the image is then reconstructed outside the system.

Figure 6:
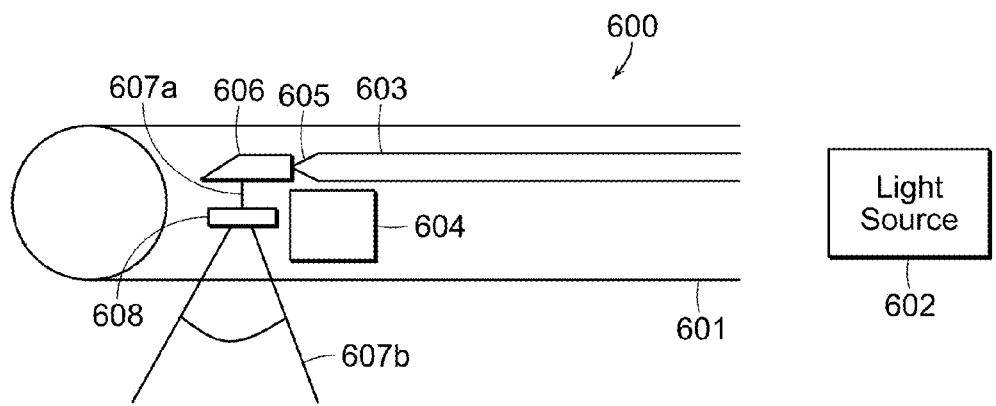
FIG. 6 is a schematic of an exemplary configuration of an apparatus of the invention having an optical diffuser.

In certain embodiments, apparatuses of the invention include an optical diffuser, as shown in the exemplary apparatus 600 in FIG. 6. The apparatus includes a hollow body 601, which is generally a catheter. Apparatus 600 also includes at least one light source 602. The light source 602 is coupled to the hollow body 601 such that light 607a is transmitted through the hollow body. In certain embodiments, the light source 602 is housed within the body 601. In other embodiments, the light source 602 is outside of the hollow body 601. In either configuration, light 607a from the light source 602 will generally travel through at least one optical fiber 603. Apparatus 600 also includes a detector 604. In certain embodiments, the detector 604 is an ultrasound transducer.

Figure 5:
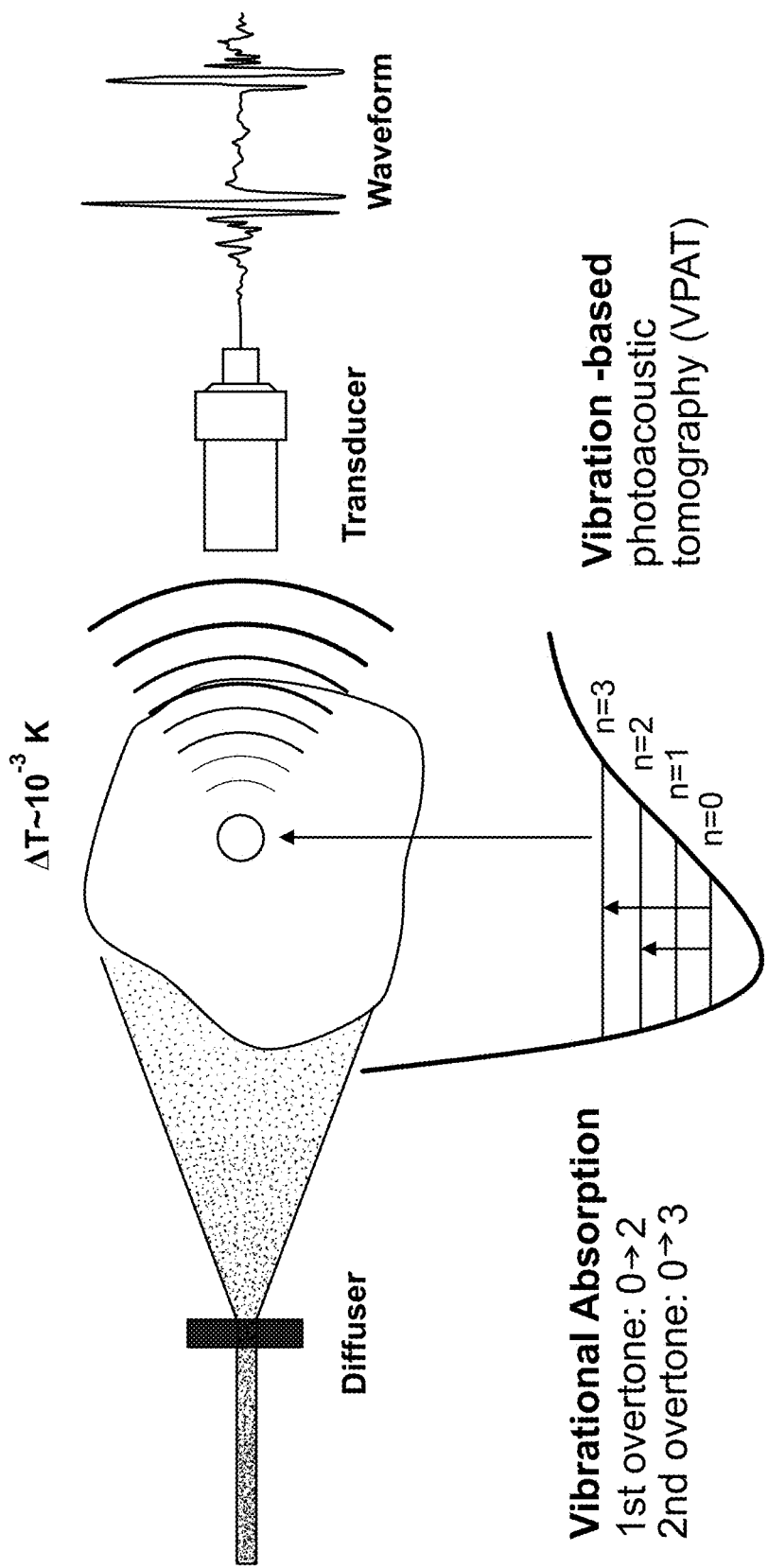
FIG. 5 depicts a diagram of the 1st (2v) and 2nd (3v) overtone absorption of a molecule using vibration-based photoacoustic tomography (VPAT).

Apparatus 600 is configured such that light 607a from the light source 602 is sent through an optical diffuser 608 to produce diffuse light 607b. Any optical diffuser known in the art may be used with apparatuses of the invention, and exemplary optical diffusers are commercially available from Thorlabs, Inc. (Newton, N.J.). The optical diffuser allows for diffused photon excitation of harmonic vibration of chemical bond (i.e., overtone transitions from n=0 to 2, 3 . . . , see FIG. 5) in the near infrared region, inherent relaxation of vibrational energy into heat, and acoustic detection of the generated ultrasound waves from the object.

The diffuse light 607b is directed onto a tissue and the detector 604 is coupled to the apparatus 600 such that it can detect a spectroscopic signal generated from tissue that has been excited by the light source 602. In the configuration in FIG. 6, light 607a from the light source 602 is directed down an optical fiber within hollow body 601 until it reaches lens 605 and prism 606. At that time, the light 607a is redirected 90° and through optical diffuser 608. The light becomes diffuse light 607b and is directed through an optically transparent portion of the body 601 so that it impinges on tissue. The 90° direction is only exemplary and the light 607a can be redirected at any desired angle.

In certain embodiments, apparatuses of the invention include pull-back capability, so that the detector and emitted light are translated along a length of the hollow body. Generally, spiral pull-back scanning is accomplished using a rotary drive apparatus and a linear drive apparatus, which define the radial operation of the transducer and the light. The rotary drive apparatus plays a role in defining the rotation (rotational operation) of the transducer and emitted light in the circumferential direction. The rotational operation is realized by the driving operation of a radial scanning motor. The linear drive apparatus plays a role in defining the movement (axial direction motion) of the transducer and emitted light in the axial direction (the distal direction in body lumen and the opposite direction thereto). The axial direction motion is realized by driving a linear drive motor, rotating a ball screw and operating a supporting portion which supports the rotary drive apparatus in the linear direction.

The linear drive apparatus is provided with a moving amount detector for detecting an operation of the linear drive motor and calculating the moving amount of the rotary drive apparatus from a predetermined reference position in the axial direction. In this embodiment disclosed by way of example, as the moving amount detector, a three-phase encoder is used. Reference numeral is one example of pulse signals in phase A, phase B and phase Z outputted from the three-phase encoder. In the operation control apparatus, by counting the pulse number of the pulse signal outputted from the moving amount detector and concurrently by detecting a phase, the moving amount of the rotary drive apparatus in the axial direction and the moving direction thereof are judged. Additional spiral pull-back mechanisms are described for example in Suzuki et al. (U.S. patent application number 2012/0215091), the content of which is incorporated by reference herein in its entirety.

The vibrational acoustic apparatuses described herein may be used to detect any biomarker within a lipid droplet. In certain embodiments, the biomarker is cholesteryl ester. In those embodiments, the apparatus of the invention detects the second overtone of C—H bonds around 1200 nm.

The amount of the biomarker within the lipid droplet (e.g., triacylglycerols, cholesteryl esters, or retinyl esters) is then compared again reference levels from samples known to be cancer-free. The data herein show that increased levels of biomarkers within the lipid droplet is indicative of cancer. Additionally, the data herein show that the higher the levels of the biomarkers within the lipid droplets, the more aggressive the cancer. Methods of the invention may be used to determine the aggressiveness of any cancer. Exemplary cancers include prostate cancer, pancreatic cancer, breast cancer, colon cancer, and brain cancer.

Methods of the invention may also involve providing a course of treatment to the patient based on results of the determining step. The treatment plan will be based on the aggressiveness of the cancer. For example, the course of treatment may involve continued monitoring or administration of an agent that blocks storage of the biomarker within the lipid droplet. Exemplary agents include fatty acid synthase inhibitors, cholesterol acyltransferase (ACAT) inhibitors, low-density lipoprotein (LDL) reducing compounds, and HMG-CoA reductase inhibitors. In certain embodiments, the agent blocks storage of cholesteryl ester in a lipid droplet.

In certain embodiments, the agent is a cholesterol acyltransferase (ACAT) inhibitor. ACAT is a membrane-bound enzyme located in the rough endoplasmic reticulum of various tissues, where it facilitates esterification of cholesterol and fatty acids into intracellular cholesterol esters. At least two isoforms of this enzyme exist: ACAT1 and ACAT2. ACAT1 regulates cholesterol homeostasis in the brain, macrophages, and adrenal glands, and ACAT2 esterifies cholesterol in the small intestine and liver.

An ACAT inhibitory compound refers to any agent that has demonstrated in vitro or in vivo binding affinity for ACAT such that the normal activity of the ACAT enzyme is reduced or eliminated. An ACAT inhibitory compound useful herein can have affinity for other targets (enzymes or receptors) besides ACAT, but in general it is desirable to use an ACAT inhibitory compound having relatively weak or no binding affinity for hormone receptors. Relatively weak in the present context means that $IC_{50}$ or $K_D$ of the compound for ACAT is lower than for a hormone receptor.

Exemplary ACAT inhibitors include acaterin, avasimibe, acetamide bezafibrate, CI-999, CL-277082, CL-283546, CL-283796, colestyramine CP-105191, CP-113818, crepiside I, crilvastatin, cyclandelate, EAB-309, eflucimibe, eldacimibe, and epicochlioquinone. Additional exemplary ACAT inhibitors are shown for example in Simeon et al., (Journal of Lipid Research, 36:1199-1210, 1995), Hekimi et al. (International publication number WO 2008/058383), White et al. (International publication number WO 2009/067397), and White (U.S. patent application number 2009/0192220), the content of each of which is incorporated by reference herein in its entirety.

Without being limited by any particular theory or mechanism of action, it is believed and the data herein show that the ACAT inhibitors interrupt the cholesterol metabolism in prostate tumor cells by decreasing LDL uptake and the level of arachidonic acid, an essential fatty acids. Such disruption depletes cholesteryl ester from the lipid droplets in the tumor, thereby directly depriving the tumor of cholesteryl ester and suppressing cell growth rate of the tumor significantly. In this manner, the ACAT inhibitor is administered to directly target the tumor and act directly on the tumor itself.

The agent that blocks storage of the biomarker within the lipid droplet (inhibitor) will often be used in the form of a pharmaceutically acceptable salt. Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleate, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

The inhibitors herein may be used, for example, for the preparation of pharmaceutical compositions that comprise an effective amount of an inhibitor, or a pharmaceutically acceptable salt thereof, as an active ingredient together or in admixture with a significant amount of one or more inorganic or organic, solid or liquid, pharmaceutically acceptable carriers.

The compositions herein are suitable for administration to a warm-blooded animal, including, for example, a human (or to cells or cell lines derived from a warm-blooded animal, including for example, a human cell), for the treatment or, in another aspect of the invention, prevention of (also referred to as prophylaxis against) a disease associated with the hepatitis B virus, comprising an amount of a compound of the present methods or a pharmaceutically acceptable salt thereof, which is effective for this inhibition, together with at least one pharmaceutically acceptable carrier.

The pharmaceutical compositions according to the methods are those for enteral, such as nasal, rectal or oral, or parenteral, such as intramuscular or intravenous, administration to warm-blooded animals (including, for example, a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The dose of an inhibitor of the present methods or a pharmaceutically acceptable salt thereof to be administered to warm-blooded animals, for example humans of approximately 70 kg body weight, is for example, from approximately 3 mg to approximately 10 g, from approximately 10 mg to approximately 1.5 g, from about 100 mg to about 1000 mg/person/day, divided into 1-3 single doses which may, for example, be of the same size. Usually, children receive half of the adult dose.

The pharmaceutical compositions have from approximately, for example, 1% to approximately 95%, or from approximately 20% to approximately 90%, active ingredients. Pharmaceutical compositions according to the invention may be, for example, in unit dose form, such as in the form of ampoules, vials, suppositories, dragees, tablets or capsules.

The pharmaceutical compositions of the present invention are prepared in a manner known per se, for example by means of conventional dissolving, lyophilizing, mixing, granulating or confectioning processes.

Solutions of the active ingredients, and also suspensions, and especially isotonic aqueous solutions or suspensions, are used, it being possible, for example in the case of lyophilized compositions that have the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The solutions or suspensions may have viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned, for example, liquid fatty acid esters that contain as the acid component a long-chained fatty acid having from 8-22, or from 12-22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, .beta.-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefosse, Paris), "Miglyol 812" (triglyceride of saturated fatty acids with a chain length of $C_8$ to $C_{12}$, Huls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredients with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

Suitable carriers are for example, fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticizer, such as glycerol or sorbitol. The dry-filled capsules may comprise the active ingredients in the form of granules, for example with fillers, such as lactose; binders, such as starches, and/or glidants, such as talc or magnesium stearate, and if desired with stabilizers. In soft capsules the active ingredients are preferably dissolved or suspended in suitable oily excipients, such as fatty oils, paraffin oil or liquid polyethylene glycols, it being possible also for stabilizers and/or antibacterial agents to be added. Dyes or pigments may be added to the tablets or dragee coatings or the capsule casings, for example for identification purposes or to indicate different doses of active ingredient.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1

Figure 8:
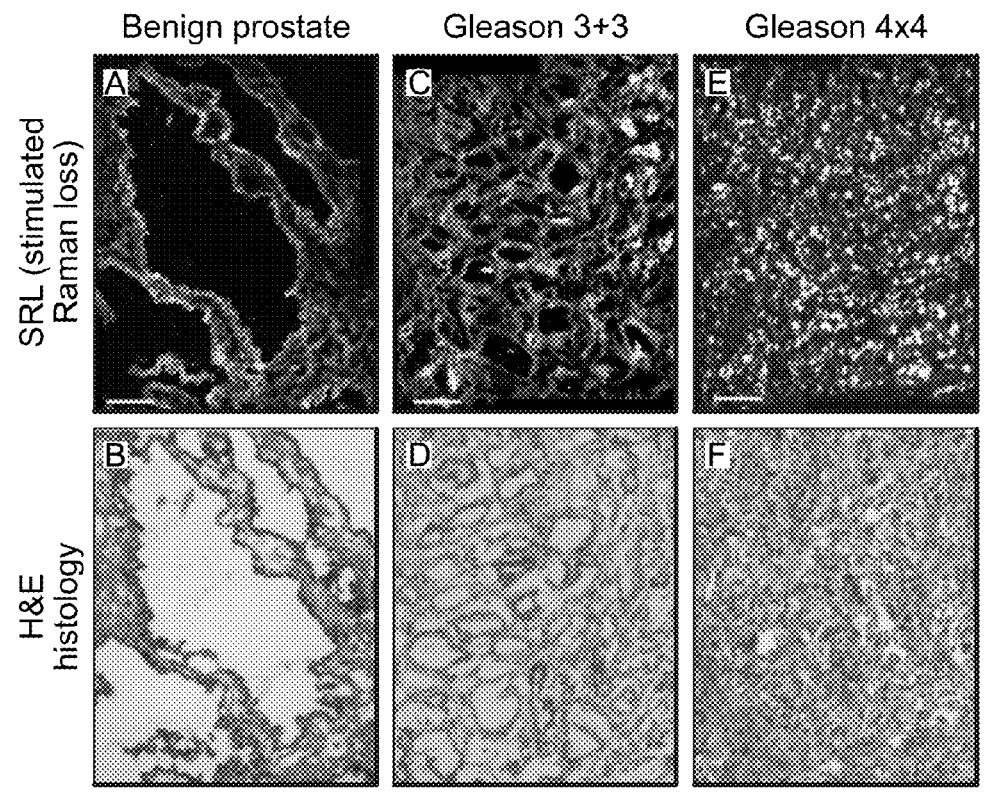
FIG. 8 shows lipid accumulation in human prostate cancer tissues. The SRL signals arise from C—H stretch vibration. Scale bars=100 µm. Panel A shows SRL of benign prostate tissue. Panel B shows H&E histology of benign prostate tissue. Panel C shows SRL of Gleason 3+3 tissue. Panel D shows H&E histology of Gleason 3+3 tissue. Panel E shows SRL of Gleason 4+4 tissue. Panel F shows H&E histology of Gleason 4+4 tissue.

Direct Observation of Cholesteryl Ester-Containing Lipid Droplets in Advanced Tumors by Spectroscopic Imaging of Benign and Cancerous Tissues from Patients Using multimodal nonlinear optical (NLO) microscopy, lipid accumulation in tissues from benign prostate, low-grade (Gleason 3+3), and high grade (Gleason 4+4) prostate cancer were evaluated. FIG. 8 shows the stimulated Raman loss (SRL) images and histological images obtained from adjacent sections of the same tissue. By tuning the excitation frequency to the C—H stretch vibration mode, the SRL signals arise from lipid-rich membranes and lipid droplets. The SRL images produced substantially same information regarding tissue morphology as the histology image. Thus, based on the blinded diagnosis by a pathologist, intracellular lipids at a tissue region defined by Gleason scores were analyzed. In benign prostate glands, single layer of epithelial cells facing a large lumen (FIG. 8, Panel A), were observed. In low-grade prostate cancer, much smaller glandular structures were observed and lipid droplets were found in most of the tumor cells (FIG. 8, Panel B). In high-grade prostate cancer, cell clusters or sheet substantially without any glandular structures were observed. In addition, lipid droplets were found in all tumor cells (FIG. 8, Panel C). Strikingly, the high-grade prostate cancer tissues contained significantly more lipid droplets than the low-grade ones, suggesting an important role of lipid accumulation in prostate cancer progression.

Figure 9:
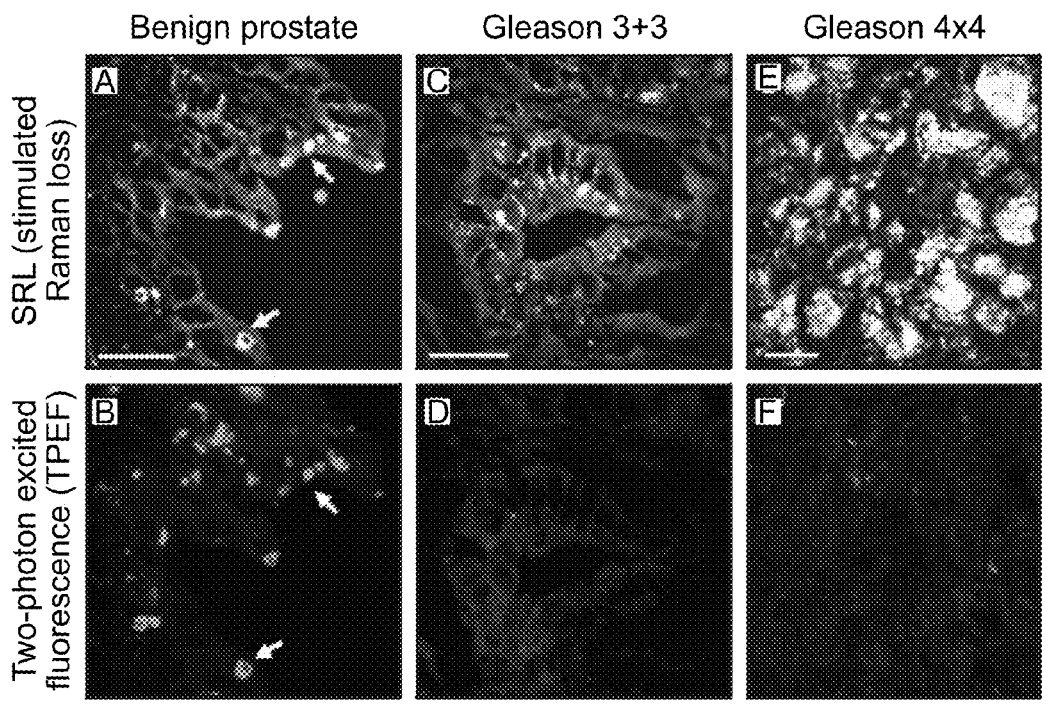
FIG. 9 depicts zoom-in images showing different types of lipid droplets found in benign v. cancerous prostate tissue. The TPEF signal arises from the tissue autoflourescence. The lipid bodies in benign tissues are lipofuscin. The lipid droplets in cancer tissue are non-flourescent and located in the cytoplasm. The amount of lipid droplets show significant difference between Gleason pattern 3 and 4. Scale bars=20 µm. Panel A shows SRL of benign prostate tissue. Panel B shows TPEF of benign prostate tissue. Panel C shows SRL of Gleason 3+3 tissue. Panel D shows TPEF of Gleason 3+3 tissue. Panel E shows SRL of Gleason 4+4 tissue. Panel F shows TPEF of Gleason 4+4 tissue.
Figure 10:
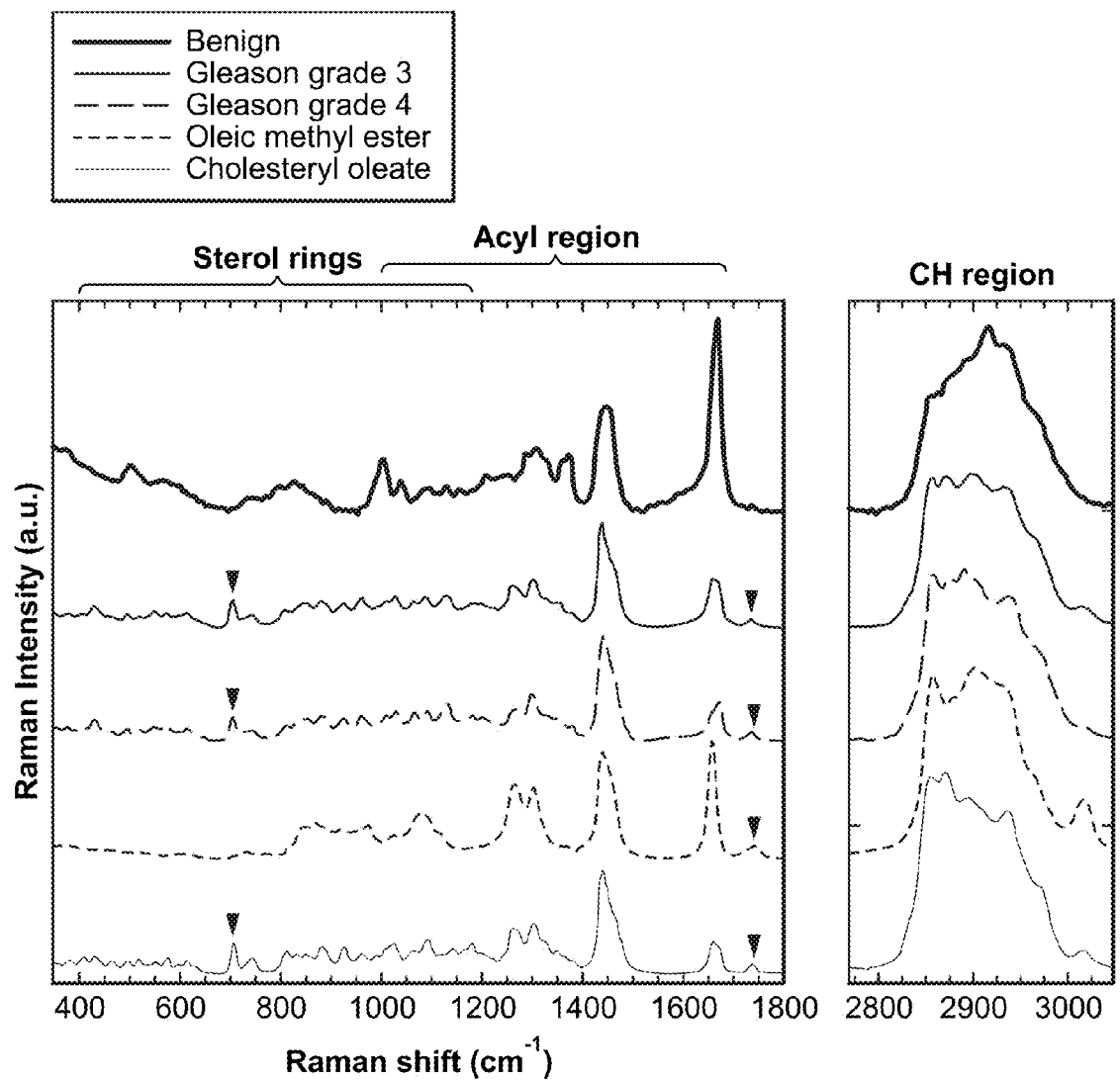
FIG. 10 shows Raman spectra of the lipid droplets in benign v. cancerous tissues from human patients. The characteristic peak at 702 $cm^{-1}$ arises from the cholesterol ring vibration. The peak at 1742 $cm^{-1}$ arises from the ester bond vibration.

Additionally, SRL and two-photon excited fluorescence (TPEF) were combined to dissect the autofluorescence properties (FIG. 9). The particles in the benign tissue showed a strong green TPEF signal (brighter regions in FIG. 9, Panel B). According to the literature (Ablin et al., Urol Res 1, 149-151 (1973); and Brunk et al., Free Radic Biol Med 33, 611-619 (2002)) those structures are assigned to be lipofuscin, a lipid-pigment complex. In contrast, the lipid droplets in both low grade and high-grade cancers did not emit any autofluorescence, indicating they are compositionally different from those in benign tissues. To determine the composition, confocal Raman spectra of individual lipid droplets were obtained using a spectrometer mounted on the NLO microscope. Excited by a 5-ps laser, Raman spectra of Lipid droplets in benign prostate (top curve), Gleason score 3 (second curve from top) and Gleason score 4 (third curve from top) are shown in FIG. 10. As controls, the Raman spectra of oleic methyl ester were also measured (fourth curve from the top) as well as that of cholesteryl oleate (bottom curve). The intensity ratio of two fingerprint Raman bands, namely the C=O ester stretching at 1742 $cm^{-1}$ and the sterol ring mode at 702 $cm^{-1}$, can be used to calculate the molar ratio cholesteryl ester to triacylglyceride in a lipid droplet. The intensity ratio of another two bands, namely the =C—H deformation on at 1267 $cm^{-1}$ and $CH_2$ twist at 1302 $cm^{-1}$, can be used to determine the degree of acyl chain unsaturation.

The spectrum of lipofuscin-like structures in benign prostate showed bands for lipid (1200-1800 $cm^{-1}$), protein (~1000 $cm^{-1}$), and prominent $CH_3$ stretching around 2930 $cm^{-1}$, but did not show the C=O stretch band at 1742 $cm^{-1}$. This result suggests the lipofuscin-like structures are composed of proteins and unesterified lipids. Degradation of the lipids by reactive oxygen species could be the source of the autofluorescence signal. The spectra for lipid droplets in both low grade and high grade prostate cancer showed the sterol ring band at 702 cm$^{-1}$ and the C=O band at 1742 cm$^{-1}$. Comparison with the spectrum of pure cholesteryl ester (FIG. 10) indicates that cholesteryl ester is a dominant component in these lipid droplets. Furthermore, lipid droplets in high grade cancer showed a much lower level of acyl chain unsaturation than the lipid droplets in low-grade cancer, as indicated by the $I_{1267}/I_{1302}$ ratio.

Additionally, cholesteryl ester containing lipid droplets have been found in drug-resistant pancreatic cancer PANC-1 cells, and in estrogen receptor negative MDA-MB-231 breast cancer but not in estrogen receptor positive MCF-7 breast cancer. Together, the imaging data revealed a previously unrecognized cholesteryl ester containing lipid store as a marker for many kinds of aggressive human cancers.

Example 2

Receptors and Enzymes that are Involved in Lipid Accumulation

In order to elucidate the mechanisms by which cholesteryl ester containing lipid droplets are accumulated in prostate cancer cells, a high-passage LNCaP cell model was selected that closely recapitulates the progression of human prostate cancer from the androgen-responsive to the hormone refractory state (Igawa, Prostate 50:222-235, (2002). In that model, high-passage LNCaP cells (passage number higher than 81) exhibits more aggressive growth and much lower androgen responsiveness compared to the parental low-passage LNCaP cells (passage number less than 33). Both high-passage (HP) and low-passage (LP) cells were shown to be androgen receptor (AR) positive (Igawa, Prostate 50:222-235, (2002). Under the SRL microscope utilized as described herein, the LNCaP-HP and LNCaP-LP cells exhibited very different morphology (FIG. 11, Panels A and C).

Both cells contained a large number of intracellular lipid droplets, which can be labeled by oil red O (ORO) in fixed cells (shown as bright regions and spots in FIG. 11, Panels B and D). The compositions of those lipid droplets are different, as indicated by the Raman spectra shown below the images (FIG. 11, Panels E and F). The lipid droplets in LNCaP-HP cells are enriched in cholesterol ester, whereas the lipid droplets in LNCaP-LP cells are enriched in triacylglycerol (TAG). Strikingly, Raman spectra from the lipid droplets in LNCaP-HP cells and those in Gleason grade 3 tissues are nearly identical. These results surprisingly indicate that intracellular accumulation of cholesterol ester in lipid droplets is a marker of prostate cancer progression.

Figure 12:
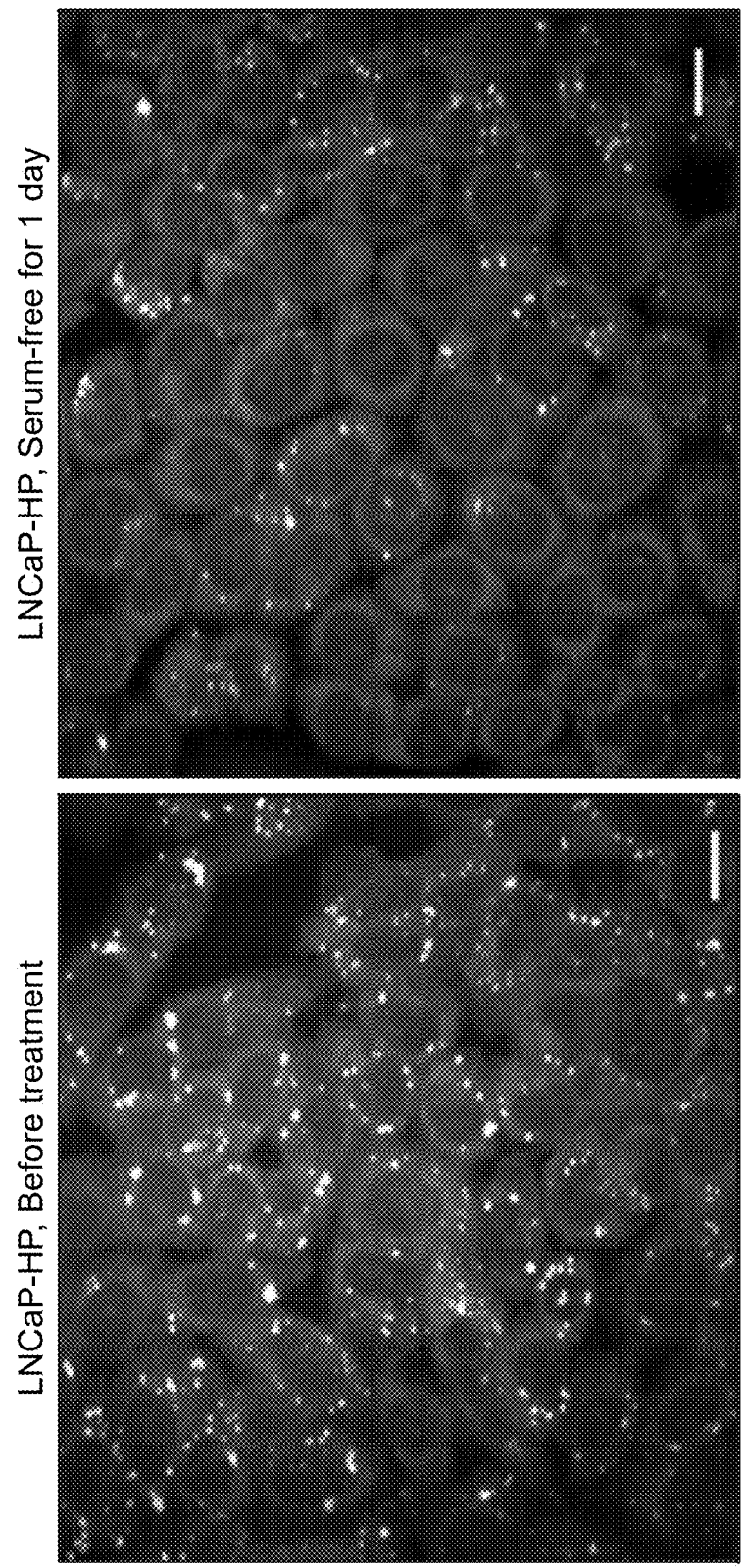
FIG. 12 is a set of photographs showing that cholesteryl ester containing lipid droplets is serum dependent. Scale bars=10 µm. The left panel is LNCaP-HP cells before treatment. The right panel is LNCaP-HP cells serum free for one day.
Figure 13A:
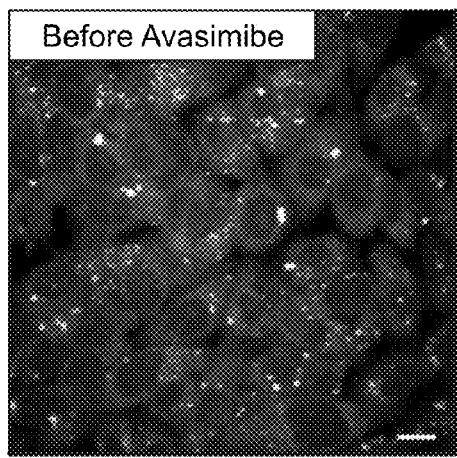
FIG. 13 shows that formation of cholesteryl ester containing lipid droplets can be blocked by an ACAT inhibitor. Scale bars=10 µm. Panel A shows cells prior to treatment with avasimibe. Panel B shows cells after treatment with avasimide. Panel C shows the Raman spectra of cholesteryl ester in cells before and after treatment with avasimide. Panel D shows the structure of avasimide.
Figure 13B:
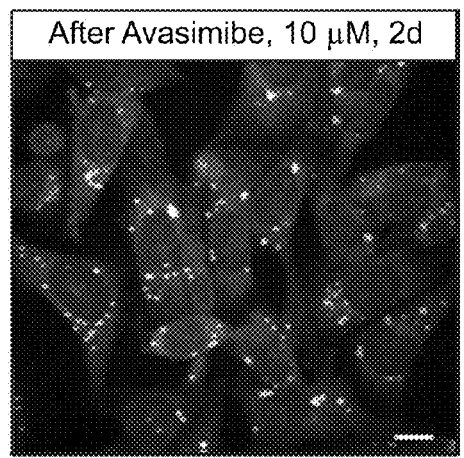
Figure 13C:
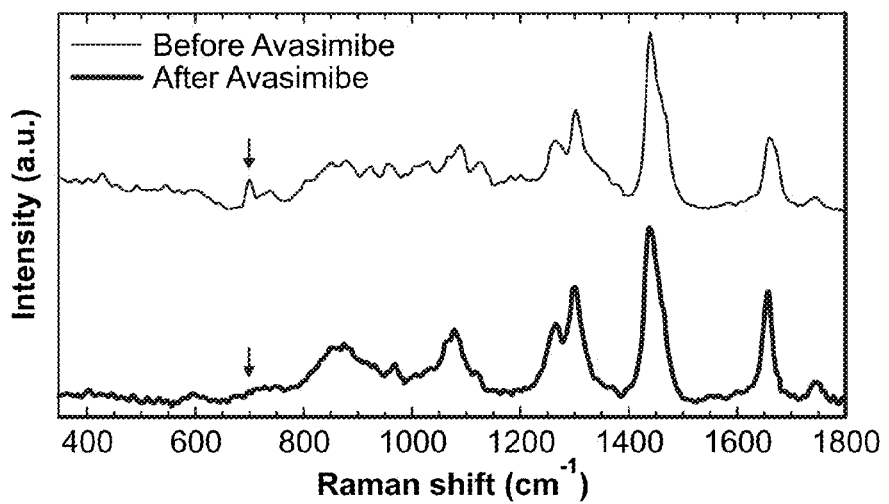
Figure 13D:
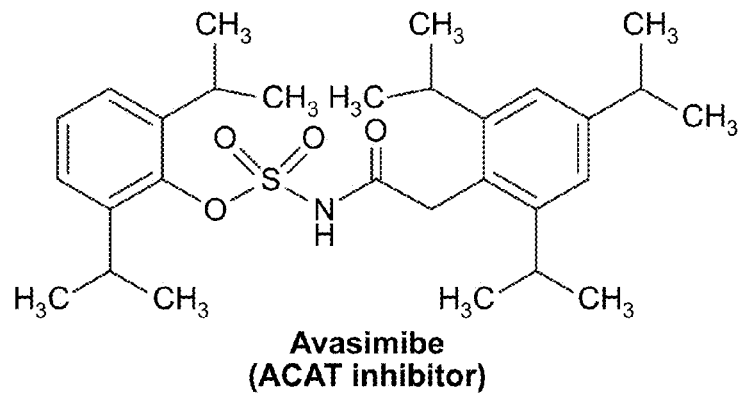

To investigate the source for cholesteryl ester storage, serum can be removed, which contained considerable LDLs, from the culture medium for a period of time, e.g., 24 h. SRL images of cells in the same dish before and after the treatment showed that serum removal significantly reduced the amount of lipid droplets inside the cells (FIG. 12). The data indicate that cholesteryl ester accumulation in LNCaP-HP cells is possibly contributed by an increased uptake of LDL.

Example 3

Cholesterol Ester Accumulation and Depletion Impacting Prostate Tumor Aggressiveness The LNCaP-HP cells were treated with an ACAT inhibitor, avasimibe (structure shown in FIG. 13, Panel D), at 10 μM for 2 days. It was found that avasimibe treatment reversed the cell morphology to that of LNCaP-LP cells (FIG. 13, Panels A and B. Moreover, avasimibe completely blocked the accumulation of CHOLESTERYL ESTER from the Lipid droplets, as indicated by the disappearance of the 702 cm$^{-1}$ Raman peak (FIG. 13, Panel C). Those data show that elevated activity of ACAT is a contributor of cholesteryl ester accumulation and cell progression.

Figure 14:
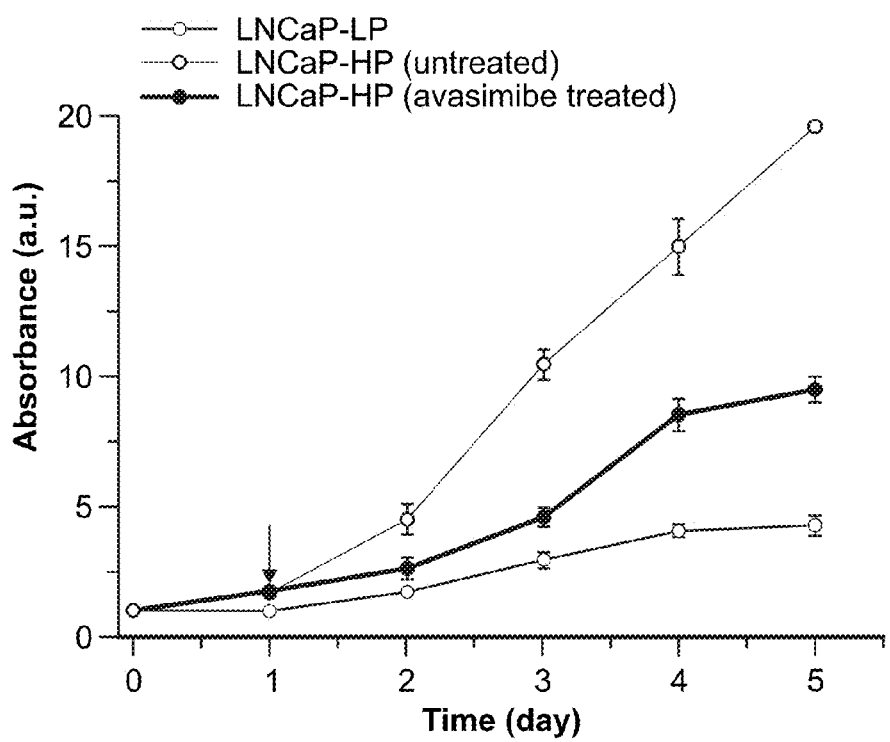
FIG. 14 is a graph showing that LNCaP-HP cells proliferate much faster than LNCaP-LP cells. Cholesteryl ester depletion with ACAT inhibitor avasimide significantly reduced growth rate of LNCaP-HP cells. ACAT treatment started at day 1.

To study the impact of cholesteryl ester storage on tumor growth, the growth rate of LNCaP-HP and LNCaP-LP cells were measured using MTT assay (a colorimetric assay for measuring number of cells present, where the color is proportional to the number of cells). The LNCaP-HP and LNCaP-LP cells showed a cell number doubling time of 12 h and 36 h, respectively. Importantly, ACAT inhibition with avasimibe significantly slowed down the proliferate rate of LNCaP-HP cells (FIG. 14). Collectively, those data indicate that cholesteryl ester containing lipid droplets represent a previously unknown marker of tumor cell aggressiveness as well as the effect of ACAT inhibitors on proliferation of the cells.

Vibrational spectromicroscopy can be used to determine the amount and compositions of lipid droplets in human tumor tissues and single living cancer cells. A vibrational photoacoustic endoscope will be developed for imaging deep tissue with penetration depth and a field of view both at centimeter scale. LDL nanoparticles may be loaded with imaging probes and therapeutic agents for cancer treatment by targeting the altered lipid metabolism. Besides imaging, other bio-analytical tools including mass spectrometry can be used to probe trace molecules such as androgen inside cells.

Example 4

Determining the Amount and Composition of Intracellular Lipid Droplets in Human Benign and Cancerous Tissues and Developing Vibrational Endoscopy for Cancer Diagnosis Using Lipids as a Marker High-speed imaging capability of stimulated Raman microscopy can be integrated with the fingerprint analysis capability of spontaneous Raman spectroscopy. A sample scanning stage can be coupled with the laser scanning microscope to ensure large-area mosaic mapping. This platform allows quantitation of total amount of lipid droplets, percentage of cholesterol ester, and degree of acyl chain unsaturation. Based on the surprising finding of cholesteryl ester rich lipid droplets in human prostate cancer tissues and not in benign prostate tissue, cholesteryl ester containing lipid droplets may serve as a marker of tumor aggressiveness. This marker may be used for prostate cancer imaging by using an imaging technique referred to as vibrational photoacoustic (VPA) microscopy. This technique permits bond-selective imaging of deep tissues with centimeter-scale penetration (Wang, Phys. Rev. Lett. 106:238106 (2011)).

The amount of stored lipid may be quantified in both low grade and high grade prostate cancer tissues (~200 specimens), in order to clarify the clinical role of lipid accumulation in prostate cancer progression. Gleason grades (3-5) of individual cancer foci, and not the Gleason sum, may be evaluated. Adjacent normal tissue, benign prostatic hyperplasia tissue, and low grade and high grade prostatic intraepithelial neoplasia (PIN) can be examined so that the differentiating capacity of lipid accumulation can be defined. Besides the amount of lipids, the molar fraction of cholesteryl ester inside the lipid droplets can also be evaluated. The cholesteryl ester concentration can also be compared among different types of prostate cancer. Subsequently, a blinded analysis of samples from patients with known outcomes can be evaluated for predictive value. The data herein show that cholesteryl ester storage is a marker of aggressiveness in prostate cancer. Based on the finding of cholesteryl ester enriched lipid droplets in human prostate cancer tissue, a transrectal VPA endoscope for label-free, non-invasive detection of molecular markers including the cholesterol ester in human tissue can be developed. Such development would be transformative as it has the potential to replace histology (including biopsy) for diagnosis of aggressive prostate cancer.

Example 5

Analyzing the Correlation Between the Amount of Lipid Store and Gleason Grade of Prostate Cancer The amount of lipid store will be represented by the area percentage of lipid droplet content in prostate cancer tissues. A threshold can be used so that the SRL signals from cell membranes and other structures, such as collagen and elastin, were not counted. In order to have valid comparison, experimental conditions can be kept the same and the threshold for image analysis can also be kept the same. The ImageJ software can be used for the percentage measurement. T-test can be used to determine if there is a significant difference between low grade and high grade prostate cancer. Finally, the best cutoff can be found to distinguish the low grade and high grade prostate cancer with high sensitivity and specificity. In one exemplary study, specimens from at least 10 different patients can be analyzed for each group.

The high grade prostate cancer tissues may likely have significantly more lipid accumulation than the low grade tissues, which can further clarify the important role of lipid accumulation in prostate cancer progression. The data show that lipid store can be used as a molecular marker to help distinguish low grade and high grade prostate cancer where inter-observer discordance can be up to 40% (Cheng et al., Essentials of Anatomic Pathology Ch. 9, Humana Press, 2002)).

Example 6

Evaluating Lipid Accumulation in Prostatic Intraepithelial Neoplasia (PIN) Specimen By following the same procedures used for prostate cancer tissues, both lipid amount and composition in low grade and high grade prostatic intraepithelial neoplasia (PIN) can be analyzed. In one exemplary study, sample size can be at least 10 for each group.

PIN tissues may likely have less, if any, lipid accumulation than cancer tissues (low grade PIN<high-grade PIN). The lipid composition may be cholesteryl ester rich neutral lipid similar to the lipid store in cancer tissues, or TAG-rich neutral lipid.

PINs might not have neutral lipid store similar to cancer tissues, which would suggest the lipid accumulation plays an important role in transformation from pre-cancer to cancer, instead of the transformation from normal to pre-cancer.

Example 7

Measuring the Concentration of Cholesteryl Ester in Lipid Droplets for Both Pre-Cancerous and Cancerous Prostate Tissues The peak ratio between 702 cm$^{-1}$ and 1742 cm$^{-1}$ ($I_{702}/I_{1742}$) can be used to indicate the fraction of cholesteryl ester out of all neutral lipids (CE+TAG). As $I_{702}/I_{1742}$ does not depend on the types of cholesteryl ester, the value obtained from cholesteryl oleate can be used as the value for 100% cholesteryl ester. Because Raman peak intensity is linear to molecular concentration, the molar ratio of cholesteryl ester in any lipid droplets of the examined tissues can be calculated.

Cholesteryl ester is expected to be the major neutral lipid inside lipid droplets in cancerous prostate tissues. The cholesteryl ester fraction out of total neutral lipid may be reduced in pre-cancerous (PIN) tissues.

Using peak height to calculate the ratio between different Raman bands might not be entirely accurate. This potential problem may be solved by fitting the peaks with Lorentzian curves and using the areas under peaks to calculate the ratio ($A_{702}/A_{1742}$). Although Raman peak intensity is theoretically linear to molecular concentration, demonstrating a linear correlation may be advantageous. To do this, the Raman spectrum of mixtures of cholesteryl oleate and triolein can be recorded at different molar ratios and generate a calibration curve.

Example 8

Evaluating the Lipid Accumulation in Other Types of Human Cancer

The same procedures as described above can be followed for evaluating the lipid accumulation in other types of human cancer. As numerous lipid droplets in cell lines of these two cancers have been found, lipid accumulation is likely present in human specimen.

Example 9

Trans-Rectal Detection of Prostate Cancer by VPA Endoscope

Figure 15:
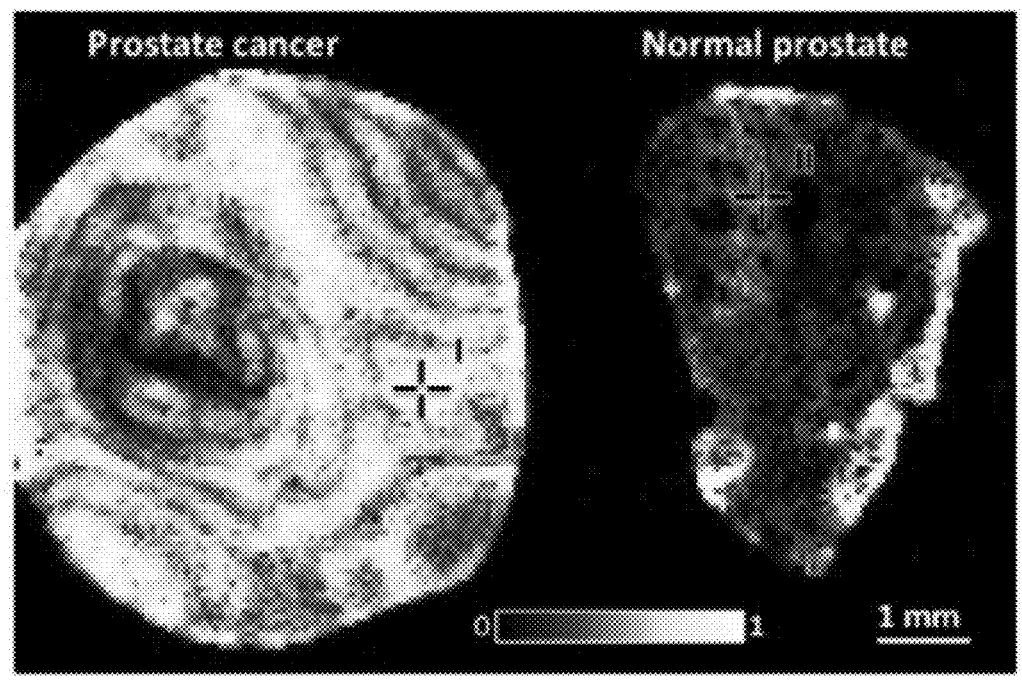
FIG. 15 is VPA images of cancerous (Gleason 4) and benign prostate tissue by excitation of the first overtone of CH bond.
Figure 16:
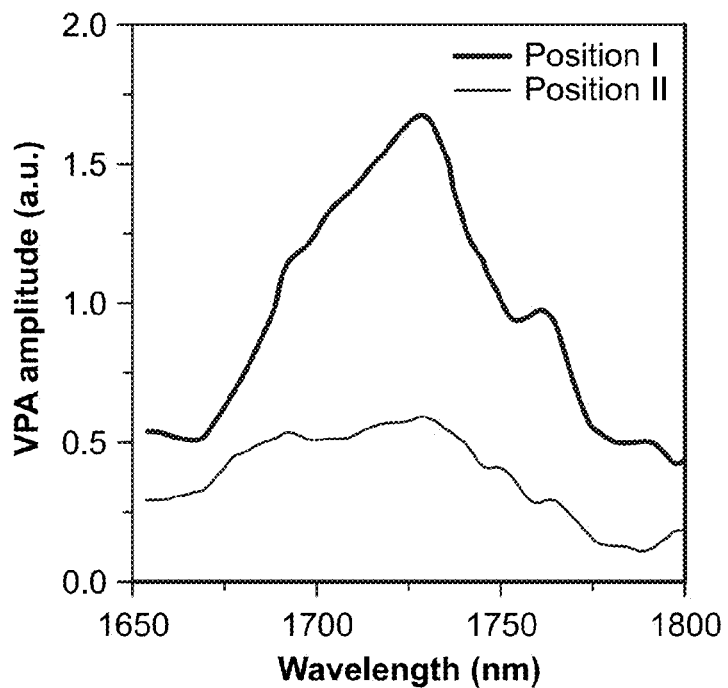
FIG. 16 shows VPA spectra from the two tissues shown in FIG. 15.
Figure 17:
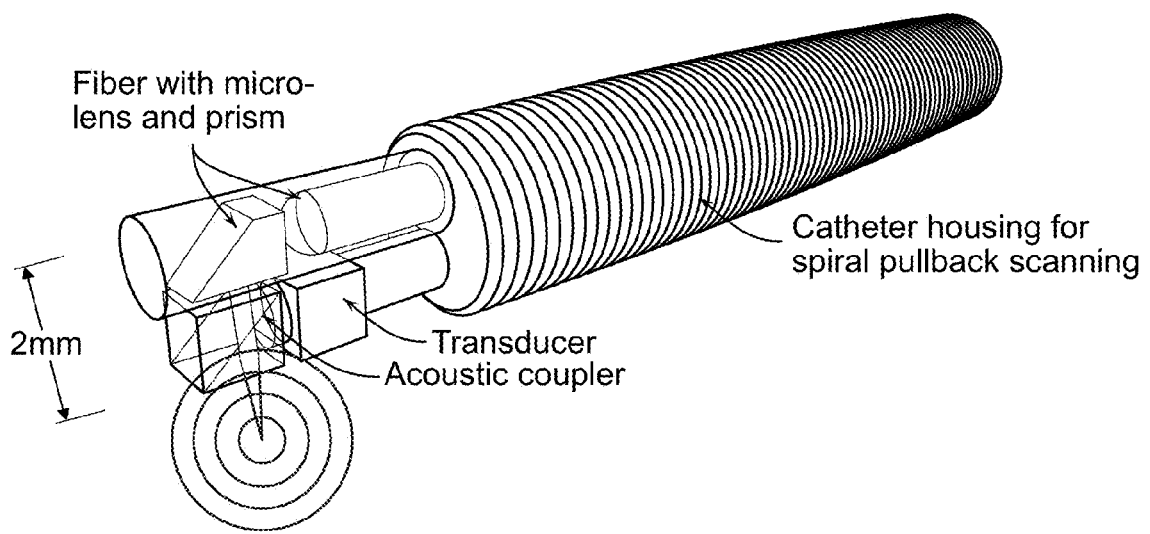
FIG. 17 is a schematic of a VPA endoscope.

The VPA imaging method is based on excitation of molecular overtone vibration and acoustic detection of the resultant pressure waves in the tissue, where the acoustic detection eliminates the tissue scattering issues encountered in near-infrared spectroscopy and enables depth-resolved signal collection in one scan. Based on the finding of increased amount of lipids in prostate cancer, VPA images of advanced prostate cancer and benign prostate were acquired and compared as illustrated in FIG. 15, where the contrast arose from the first overtone transition of C—H bonds (FIG. 16). Based on the microscopy study, a fiber-based vibrational photoacoustic endoscope can be developed for clinical detection of tumors using lipids as a molecular marker. Schematic of the VPA endoscope according to one embodiment of the present disclosure is shown in FIG. 17. A 20-MHz ultrasound transducer of 0.5×0.5 mm size is used for detection, and the acoustic coupler is miniaturized to fit the transducer. A catheter housing of 2 mm diameter, modified from current intravascular ultrasound catheter (e.g., from Boston Scientific Co.), can be used to bundle the transducer wire and the optical fiber. A 1-kHz nanosecond laser and a spiral pullback scanning system can be applied to ensure real-time data acquisition.

As the VPA signal is linearly proportional to the density of certain chemical bonds, a significant difference in the VPA images between low-grade (Gleason) and high-grade prostate cancer may be visualized. Moreover, the percentage of triacylglyceride and cholesterol ester can be determined through the multivariate curve resolution—alternative least square fitting of the VPA spectra.

If the ultrasound transducer of 0.5×0.5 mm size is not sufficiently sensitive, a Fabry-Perot cavity based ultrasound sensor can be used instead. In this configuration, the ultrasonic wave induces vibration of the diaphragm, which causes interference of light in the Fabry-Perot cavity. Such interference is then measured by a photodiode. The Fabry-Perot sensor may increase the sensitivity by three orders of magnitude.

Example 10

Figure 18:
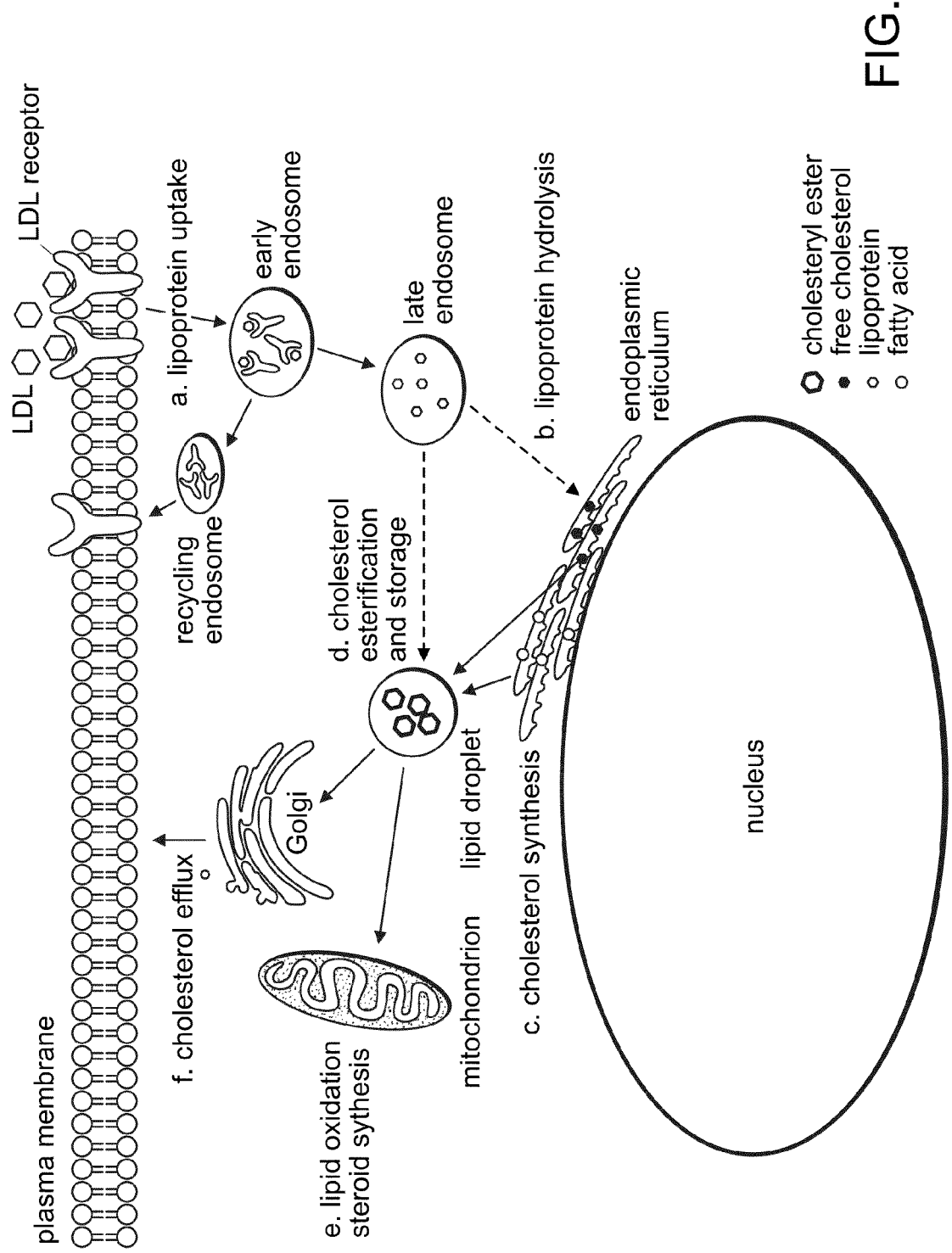
FIG. 18 is a schematic showing cholesteryl ester lipid droplets as a source for de novo synthesis of steroid in prostate cancer cells.

Investigating Tumor Behaviors Under Conditions of Lipid Storage and Depletion to Unravel the Impact of Lipid Accumulation and Deprivation on Cancer Aggressiveness Advanced prostate cancer is known to rely on activation of androgen receptor. Because cholesterol as a precursor for androgen is synthesized in endoplasmic reticulum whereas the first step converting cholesterol to pregnenolone occurs inside the mitochondrion, cholesteryl ester containing lipid droplets likely play a role in de novo androgen synthesis through active transport of cholesterol from the endoplasmic reticulum to mitochondria or Golgi, as illustrated in FIG. 18. cholesteryl ester rich LNCaP-HP cells have a higher proliferation rate than LNCaP-LP cells, and that depleting cholesteryl ester significantly lowered the proliferation of LNCaP-HP cells. Because the LNCaP-HP cells are derived from LNCaP-LP cells without castration, these cells imitate the high-grade human prostate cancer tissue that has been examined. As cholesteryl ester accumulation in LNCaP-HP cells can be significantly reduced by either lowering exogenous LDL level or inhibiting cholesterol esterification, the effects of cholesteryl ester accumulation and depletion on aggressiveness of LNCaP cells can be examined by comparing the cellular behaviors before and after cholesteryl ester depletion.

Cholesteryl ester accumulation can be depleted by either lowering exogenous LDL level or inhibiting ACAT. Cancer cell behaviors can be measured for various groups of cells (e.g., group 1 and 2: LNCaP-HP cells with or without cholesteryl ester depletion by lowering exogenous LDL level; group 3&4: LNCaP-LP cells with or without cholesteryl ester depletion by lowering exogenous LDL level, as the negative controls for groups 1 and 2; groups 5 and 6: LNCaP-HP cells with or without cholesteryl ester depletion by inhibiting ACAT; and group 7 and 8: LNCaP-LP cells with or without CE-depletion by inhibiting ACAT, as the negative controls for 5 and 6). Measurements can include cell proliferation, percentage of dividing cells, cell migration and invasion. To determine how cholesteryl ester is utilized for cell activities, and whether cholesteryl ester is used for de novo synthesis of androgen through intracellular active transport of LDs, can be checked.

Example 11

Measuring Cell Growth of LNCaP-HP Cells with CE Storage and Depletion

Cell proliferation by MTT assay for a period of time, e.g., about 2 weeks, can be tracked to obtain both exponential growth phase and stationary phase, thereafter, quantitatively cell doubling time and maximum cell number between cells with cholesteryl ester storage and cells with cholesteryl ester depletion, can be compared. In addition, cell division can be monitored and quantitated using DAPI labeling and flow cytometry. Furthermore, the expression level of cyclin D1 which plays an important role in regulation of cell mitosis can be measured in LNCaP-HP cells with or without cholesteryl ester depletion.

LNCaP-HP cells likely show more aggressive growth than LNCaP-LP cells, indicated by higher proliferation rate and greater fraction of DNA synthesis/cell mitosis cycle phases. The LNCaP-HP cells likely lose capabilities of aggressive growth after CE depletion, and expression of cyclin D1 likely can be suppressed in LNCaP-HP cells after CE depletion.

Example 12

Figure 19:
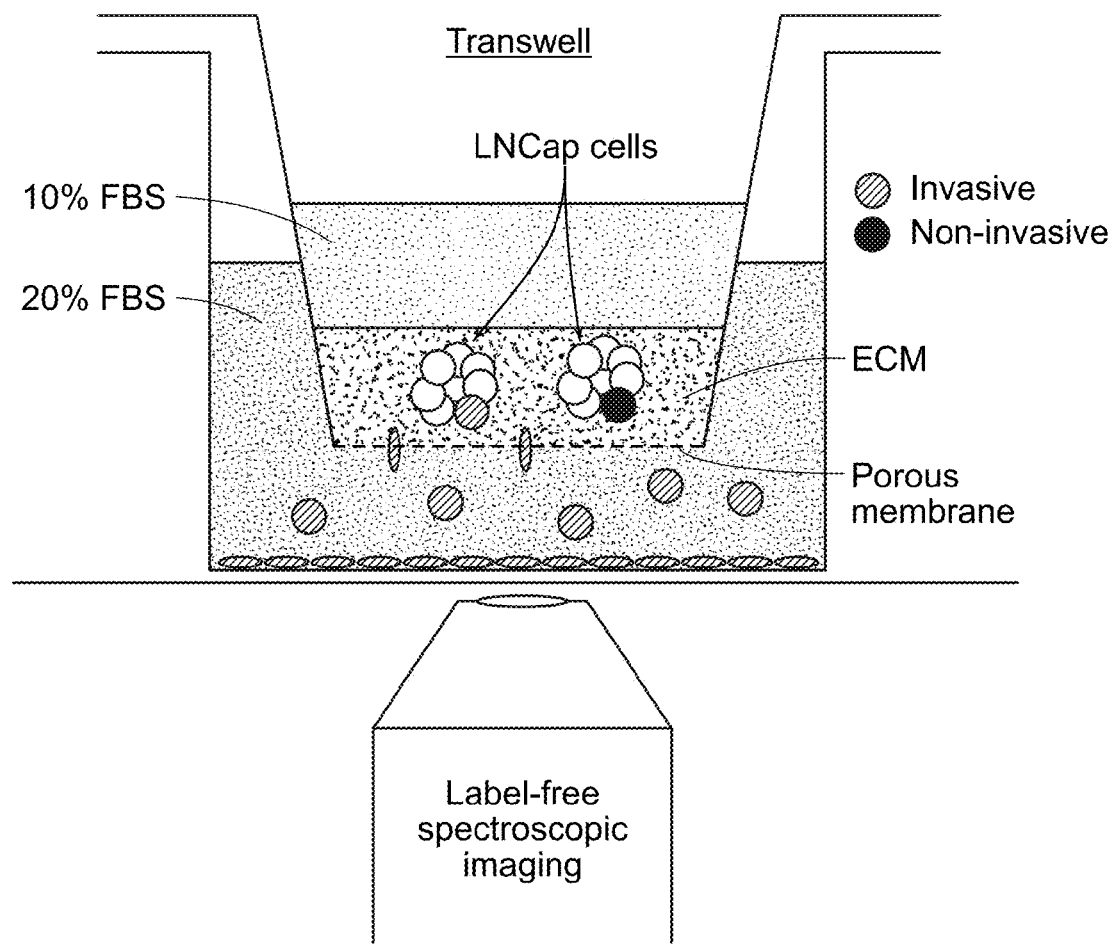
FIG. 19 is a schematic showing a 3D culture model for cell migration and invasion assay.

Measuring Cell Migration and Invasion of Cholesteryl Ester Stored and Cholesteryl Ester Depleted LNCaP Cells in 3D Culture According to one embodiment, a 3D culture model includes a transwell with membrane pore size of about 8 μm and a well of a tissue culture plate (FIG. 19). Cells can be seeded in the transwell with or without the layer of extracellular matrix (ECM), which can be recapitulated by Matrigel. The ECM layer is used for cell invasion measurement. The ECM layer occludes the membrane pores, blocking non-invasive cells from migrating through. Invasive cells, on the other hand, migrate through the ECM layer and adhere to the bottom of the membrane. Applying this model to the NLO microscopy allows us to track the cells that migrate through Matrigel, transverse the porous membrane, and finally settle down at the bottom of the well. Large area mapping with a field of view of at least 5×5 mm can be performed, so that the number of invaded cells can be quantitated. As cells migrate or invade, they can remodel ECM. As matrix metalloproteinases (MMPs) are often responsible for ECM remodeling, the MMP activity using zymography can be measured. As the surface receptor CD44 binds to ECM and is associated with cancer metastasis, the expression level of this protein via immunostaining LNCaP-HP cells can be checked with cholesteryl aster stored or depleted.

LNCaP-HP cells likely demonstrate higher rates of migration than LNCaP-LP cells, indicated by a greater number of cells passing through the porous membrane and settling down at the bottom of the well. CE depletion likely suppresses the aggressive migration of LNCaP-HP cells. Furthermore, the MMP activity and CD44 expression are likely higher in LNCaP-HP cell than that in LNCaP-LP cell, and cholesteryl ester depletion should inhibit the MMP activity and reduce CD44 expression in LNCaP-HP cells.

Example 13

Measuring the Level of De Novo Androgen Synthesis and Mapping the Intracellular Location of Androgen Receptor in LNCaP Cells with Cholesteryl Ester Storage and Depletion Cells can be cultured in charcoal stripped medium to avoid exogenous source of androgen, and then the level of testosterone and dihydrotestosterone can be measured inside cells using LC-MS (B, M. R. et al., Cancer Research 68, 4447-4454 (2008)). Moreover, immunostaining of the androgen receptor can be performed and the intracellular location of the androgen receptor can be determined by confocal fluorescence microscopy.

LNCaP-HP cells shows higher activity of de novo androgen synthesis than LNCaP-LP cells, and cholesteryl ester depletion can lower de novo androgen synthesis in LNCaP- HP cells. Furthermore, cholesteryl ester accumulation can be correlated with an effective translocation of androgen receptor to the nucleus.

Example 14

Determining the Role of Lipid Droplet Trafficking in De Novo Androgen Synthesis

Lipid droplet trafficking inside LNCaP-HP cells can be recorded by SRL microscopy and analyzed by single particle tracking method. Mitochondria can be labeled by a mitotracker and visualized by two-photon fluorescence on the same microscope. Because lipid droplets use Rab18 as an adapter to motor proteins, Rab18 using RNA interference can be knocked out and the androgen level and androgen receptor translocation using methods described herein can be monitored. As a result, directional lipid droplet movements inside the cells are likely to be seen. Blocking lipid droplet trafficking is expected to lower the level of androgen and reduce the translocation of androgen receptor into the nucleus.

However, cholesteryl ester depletion may not be able to completely shut down aggressive activities of LNCaP-HP cells. Fatty Acid Synthase (FASN) inhibitor is a potential candidate that may be used individually or in combination with one or both of ACAT inhibitor and LDL lowering agent to exert the most profound effect on cancer aggressiveness. While emphasis is placed on LNCaPHP cells which exhibit the same lipid profile as human specimen, other prostate cancer cell lines, including androgen-independent C4-2 cells developed in mice with castration after initial LNCaP transplantation, PC3 (from bone metastase), and DU145 (from brain metastase) can also be checked.

Example 15

Figure 20:
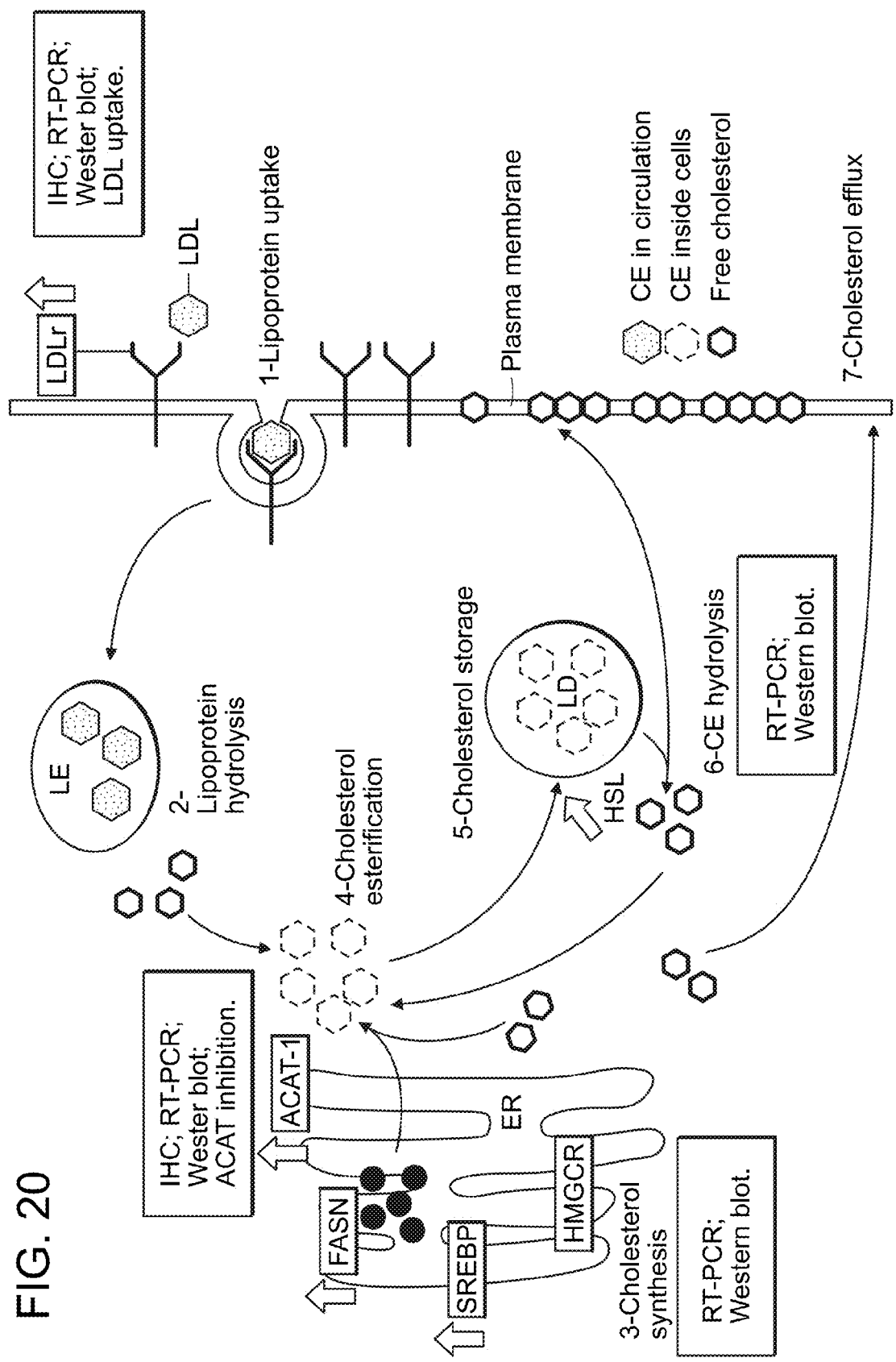
FIG. 20 is a schematic showing a proposed diagraph of cholesterol metabolism deregulation and cholesteryl ester storage in prostate cancer cells. The box on the left shows methods for gene and protein expression assays.

Examining Receptors and Enzymes that are Involved in Lipid Accumulation in Tumor Cells and Developing Novel Methods for Cancer Imaging and Treatment by Targeting the Altered Lipid Metabolism The data herein show that cholesterol metabolism is altered in human prostate cancer (FIG. 20). In general, cholesterol esterification is one way by which cells accumulate cholesterol while avoiding toxicity induced by high-level of free cholesterol (Simons, Science 290:1721-1726, (2000)). The key regulatory mechanisms of cholesteryl ester storage include cholesterol de novo biosynthesis rate-limited by HMG-CoA reductase, uptake of exogenous cholesterol mediated by low density lipoprotein receptor (LDLr), cholesterol esterification mediated by ACAT1 activity, and cholesterol efflux mediated by high density lipoprotein receptor (HDLr) (Tosi et al., Clinica Chimica Acta 359:27-45, (2005)). Both LDL deprivation and ACAT inhibition blocked the storage of cholesteryl ester in lipid droplets. There may likely be a role of LDL in cholesteryl ester storage in prostate cancer which may provide new opportunities of cancer treatment by targeting the altered cholesterol metabolism. In particular, targeted delivery of ACAT inhibitor through the LDLr mediated endocytosis offers a new promise for treating the castration-resistant prostate cancer. Furthermore, the dysregualted cholesterol metabolism can be studied (as illustrated in FIG. 20).

Immunohistochemistry and RT-PCR of key enzymes and receptors including LDLr, ACAT, and HMG-CoA on human tissues can be studied to identify the expression levels of these proteins in cancer tissue compared to benign tissue. In addition Western blot and RT-PCR can be used to measure expression level of these proteins (e.g. LDLr, ACAT, and HMG-CoA), on both LNCaP-LP and LNCaP-HP cells). These experiments can determine if the LNCaP-HP cell model recapitulates lipid metabolism characteristics of advanced human prostate cancer. To further investigate the effects of each mechanism (de novo synthesis, uptake, esterification) on cholesteryl ester accumulation, LNCaP-HP cells can be treated with HMG-CoA reductase inhibitor, lipoprotein-deficient serum with or without addition of LDL-cholesterol, ACAT inhibitors (e.g., Pfizer CP-113 818 or Sandoz-58035), and lipid accumulation can be monitored by imaging.

Example 16

Measuring the Expression Levels of Key Enzymes and Receptors that Regulate Intracellular Cholesteryl Ester Accumulation in Human Tissues and the LNCaP Cell Model Immunohistochemistry and Western blot for LDLr, ACAT1, and HMG-CoA can be performed on human prostate tissues. Furthermore, Western blot and RT-PCR can be used to measure expression levels of protein/gene including LDLr, ACAT1, and HMG-CoA in LNCaPLP and -HP cells.

Significantly higher expression level of LDLr and ACAT1 are likely, however, lower or similar levels of HMG-CoA in cancer tissues compared to benign tissues are also likely. Also, a significantly higher expression level (for both protein and gene) of LDLr and ACAT1 are also likely, but lower or similar level of HMG-CoA in LNCaP-HP cells compared to LNCaP-LP cells are also likely. If the immunohistochemistry signal is difficult to quantify the expression level between benign and cancer tissues, Western blot or ELISA can be used to quantitate the protein levels.

Example 17

Measuring the Effect of LDL Uptake and ACAT Inhibition on Cholesteryl Ester Accumulation in LNCaP-HP Cells Initially the LDL in the culture medium can be removed by using lipoprotein-deficient medium over a period of time. When cholesteryl ester accumulation is significantly reduced, LDL can be added back to monitor the change of cholesteryl ester accumulation inside LNCaP-HP cells. Furthermore, the LNCaP-HP cells can be treated with various ACAT inhibitors, such as Pfizer CP-113 818 or Sandoz-58035, and then the cells can be analyzed with spectroscopic imaging.

LNCaP-HP cells likely have significantly higher LDL uptake than LNCaP-LP cells. LNCaP-HP cells can gradually re-gain the cholesteryl ester rich LDs after the re-addition of LDL to the lipoprotein-deficient medium, whereas the lipid accumulation in LNCaP-LP cells may not be affected by either depletion of lipoprotein or re-addition of LDL. Furthermore, similar results from the ACAT inhibitors can be achieved as Avasimibe can deplete CE accumulation.

Example 18

Encapsulating Imaging Probes into LDL for In Vivo Cancer Imaging

Figure 21:
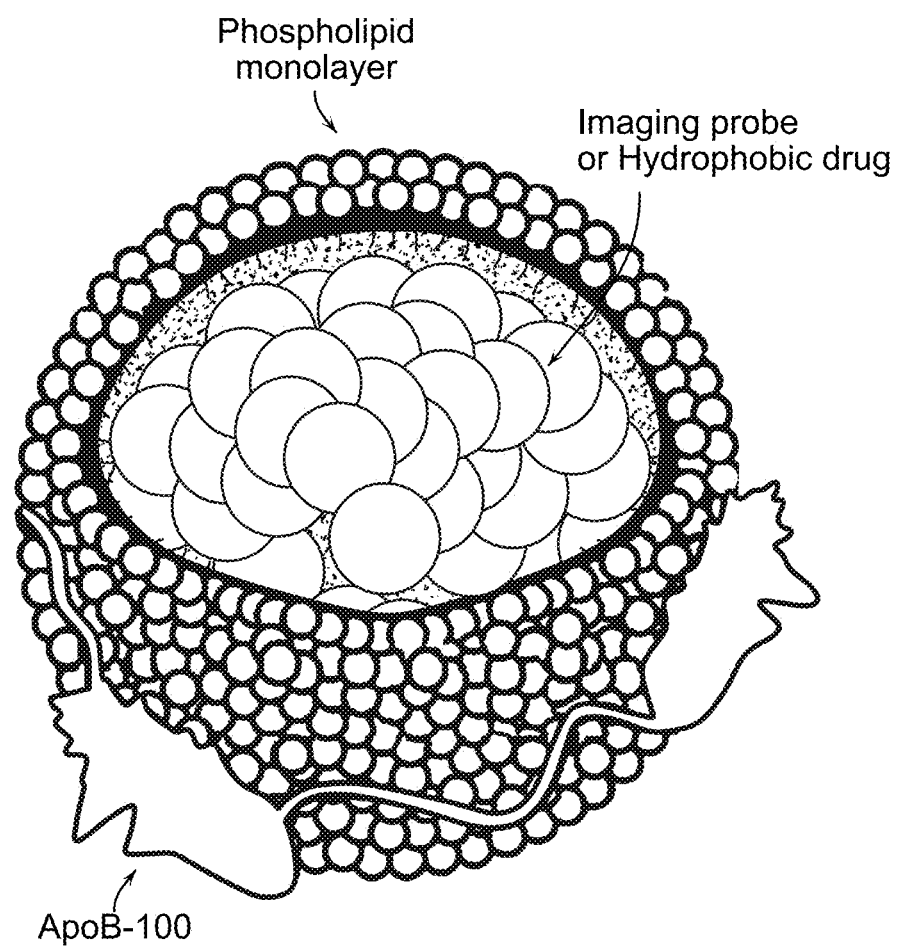
FIG. 21 is a schematic showing LDL nanoparticles as a carrier for targeted imaging and treatment of advanced prostate cancer.

The dry film method can be used to load lipophilic near infrared dye (DiI) into LDL particles (FIG. 21). A dry film of DiI can be prepared under $N_2$ gas and then mixed with LDL solution in phosphate buffered saline (PBS), followed by incubation over a period of time at a temperature of, e.g., 37° C. Cellular uptake of the labeled LDL particles can be checked in LNCaP-HP cells. A LNCaP xenograft mouse model, for which the tumor cells are known to overexpress LDLr (Leon et al., The Prostate 70:390-400 (2010)), can be used. The labeled LDL can be administrated through tail vein. Serum level of labeled LDL can be measured by in vivo imaging of blood vessels, e.g., in ear lobe in two groups of mice. Organs can be exercised and biodistribution of the labeled LDL can be determined using an IVIS instrument in another two groups of mice. An intense fluorescence signal from the tumor cells in vitro and the solid tumor in vivo can then be generated. However, if the loading efficiency is not sufficient, a reconstitution method can be utilized. In order to make the analysis of DiI-LDL uptake more quantitative, flow cytometry can be used to quantify the fluorescent signals from DiI-LDL inside cells.

Example 19

Encapsulating ACAT Inhibitor into LDL and Therapeutic Methods for Treating Castration Resistant Prostate Cancer In one embodiment, potent ACAT inhibitor (ACATi), examples of which are identified herein, can be encapsulated into LDL using various methods, e.g., thin film or reconstitution method (FIG. 21). Loading efficiency can be determined by UV-Vis spectroscopy. The LNCaP-HP cells can be treated with ACATi-loaded LDL and the proliferation rate can be measured by the MTT assay. For in vivo studies, the blood level of ACATi can be measured by paper-spray mass spectrometry (Wang et al., Angew. Chem. Int. Ed. 49:877-880 (2010)). The volume of xenografted LNCaP tumor and serum prostate specific antigen (PSA) level can be measured between the control group, the LDL vehicle group, and the ACATi-loaded LDL group. Organ toxicity assay can then be conducted (Shi, Nat. Nanotechnol. 5:80-87, (2010)).

A lower growth rate in LNCaP cells treated with ACATi-loaded LDL is likely. In vivo, a dose-dependent toxicity in mice may be likely. At the dosage of tolerable toxicity, a slower growth of the tumor after the treatment may be likely. However, if the effectiveness in not significant, ACAT inhibitor can be combined with an FDA approved anti-cancer drug, paclitaxel. Such combination therapy may likely increase the effectiveness.

Example 20

In Vivo Treatment for Prostate Cancer

Metabolic reprogramming allows cancer cells to sustain high proliferative rates and resist cell death. Whereas alterations to glucose and amino acid metabolism have been extensively studied, altered lipid metabolism in cancer is increasingly recognized based on the findings of imbalanced lipid signaling network and dysregulated lipogenic enzymes. Storage of esterified lipids in lipid droplets, an essential aspect of lipid metabolism, is however underappreciated in cancer research despite recent advances in lipid droplet biology. In cell lines of human prostate cancer, lipid accumulation was commonly seen and partially attributed to the up-regulation of fatty acid synthase (FASN), a key lipogenic enzyme implicated in many human malignancies. Technically, because the composition of individual lipid droplets is not accessible with traditional methods such as electron or fluorescence microscopy, the exact role of lipogenesis in prostate cancer progression remains elusive. By employing vibrational spectromicroscopy that quantifies not only the amount but also the composition of lipid droplets in live cells and intact tissues, we report an unexpected enrichment of cholesteryl ester in high-grade prostate cancer and metastatic diseases, but not in normal and benign prostate. Molecular and animal studies further identified cholesteryl ester as a biomarker and cholesterol esterification as a target of treatment.

Figure 22:
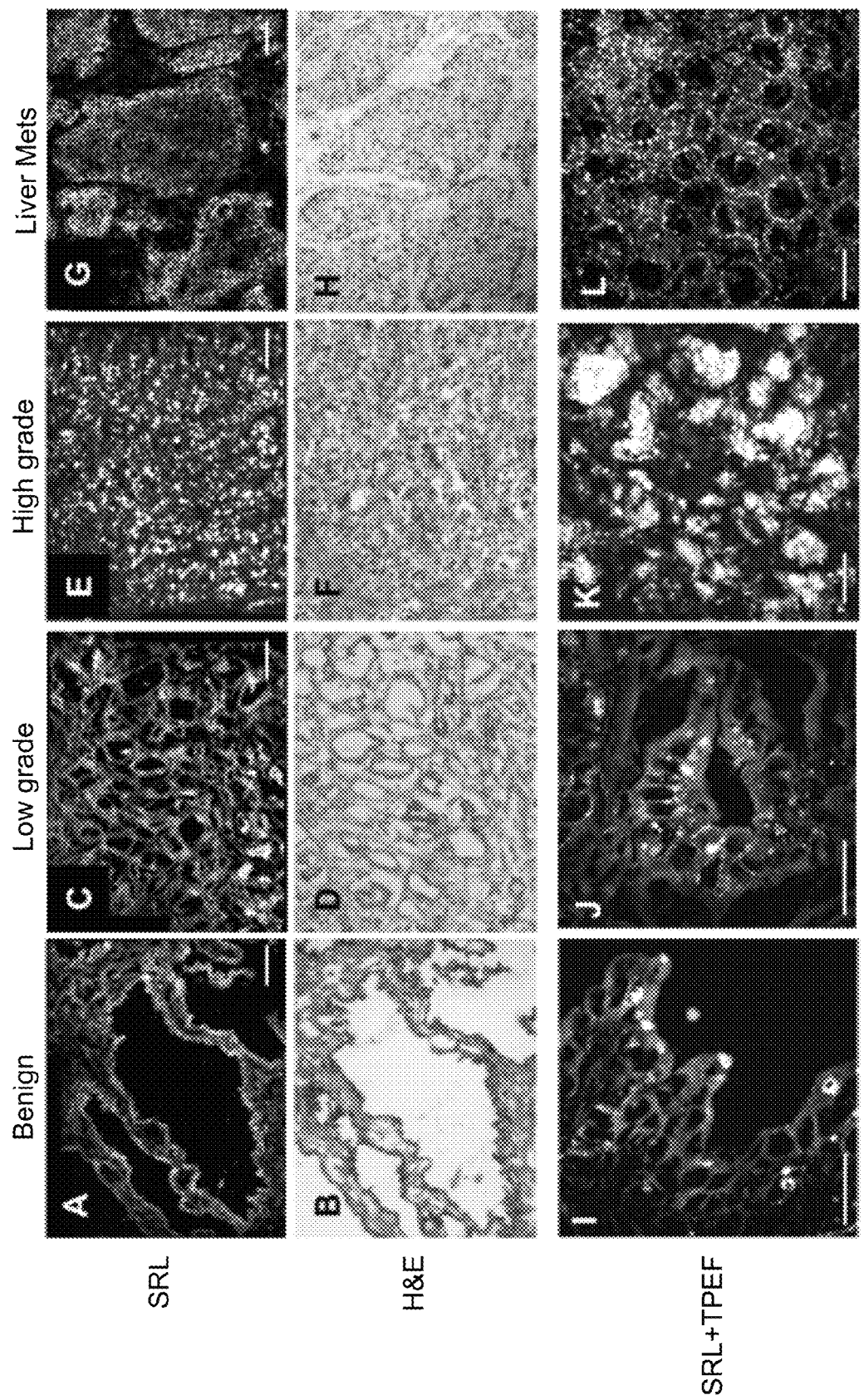
FIG. 22 panels A-F and I-K are images showing different types of lipid droplets found in benign v. cancerous prostate tissue. Panel A shows SRL of benign prostate tissue. Panel B shows H&E histology of benign prostate tissue. Panel C shows SRL of low grade prostate cancer tissue. Panel D shows H&E histology of low grade prostate cancer tissue. Panel E shows SRL of high grade prostate cancer tissue. Panel F shows H&E histology of high grade prostate cancer tissue. Panel I shows SRL combined with TPEF of benign prostate tissue. Panel I shows SRL combined with TPEF of benign prostate tissue. Panel J shows SRL combined with TPEF of low grade prostate cancer tissue. Panel K shows SRL combined with TPEF of high grade prostate cancer tissue. Panels G-H and L show images of liver mets. Panel G shows SRL of liver mets. Panel H shows H&E histology of liver mets. Panel L shows SRL combined with TPEF of liver mets.

Tissues collected from a broad spectrum of human prostate lesion types including normal (n=13), benign (n=16), prostatic intraepithelial neoplasia (PIN) (n=3), low grade prostate cancer (Gleason grade 3) (n=12), high grade prostate cancer (Gleason grade 4/5) (n=12), and metastases (n=9) was examined. By tuning the beating frequency to be resonant with C—H stretch vibration, substantial stimulated Raman loss (SRL) signals (grey color) arose from the lipid-rich cell membranes and intracellular lipid droplets, whereas weak SRL signals were generated by the lipid-poor cell nuclei. The lipid droplets showed the strongest signal among all the structures because of their abundance in C—H bonds. Morphologically, the SRL images provided identical information as hematoxylin and eosin (H&E)-stained slides. In normal, benign and PIN prostate gland, a single layer of epithelial cells facing a large lumen was observed by SRL (FIG. 22, Panel A) and confirmed by the H&E staining (FIG. 22, Panel B) of the adjacent slice. In the same manner, small glandular structures were observed in low grade prostate cancer (FIG. 22, Panel C) and cell clusters or sheets without any glandular structures in high grade prostate cancer (FIG. 22, Panel E), with neighboring slices stained with H&E (FIG. 22, Panels D and F). FIG. 22, Panel G, presents an SRL image of liver metastatase confirmed in the H&E slide (FIG. 22, Panel H). SRL images of adrenal, abdominal, rib lung, lymph node, and liver metastases were also observed. As a striking observation, lipid accumulation occurred ubiquitously in all stages of prostate cancer, and the lipid amount was positively associated with the Gleason grade. The intracellular lipid droplets accumulated in each type of prostate lesions were more clearly seen in the high magnification images (FIG. 22, Panels I-L). By combining SRL with two-photon excited fluorescence (TPEF) on the same microscope, it was found that the intracellular particles in benign prostate glands expressed both SRL and TPEF signals (FIG. 22, Panel I), suggesting that these particles contained not only lipids but also autofluorescent components. These autofluorescent granules were consistently seen in all 13 normal prostates, 16 benign prostates, and 3 PIN lesions, and assigned to be lipofuscin according to previous reports on pigments in benign prostate. In contrast, except 4 border line cases, the 20 primary prostate cancer lesions and all 9 metastases contained lipid droplets but no autofluorescent granules (FIG. 22, Panels J-L).

Figure 23:
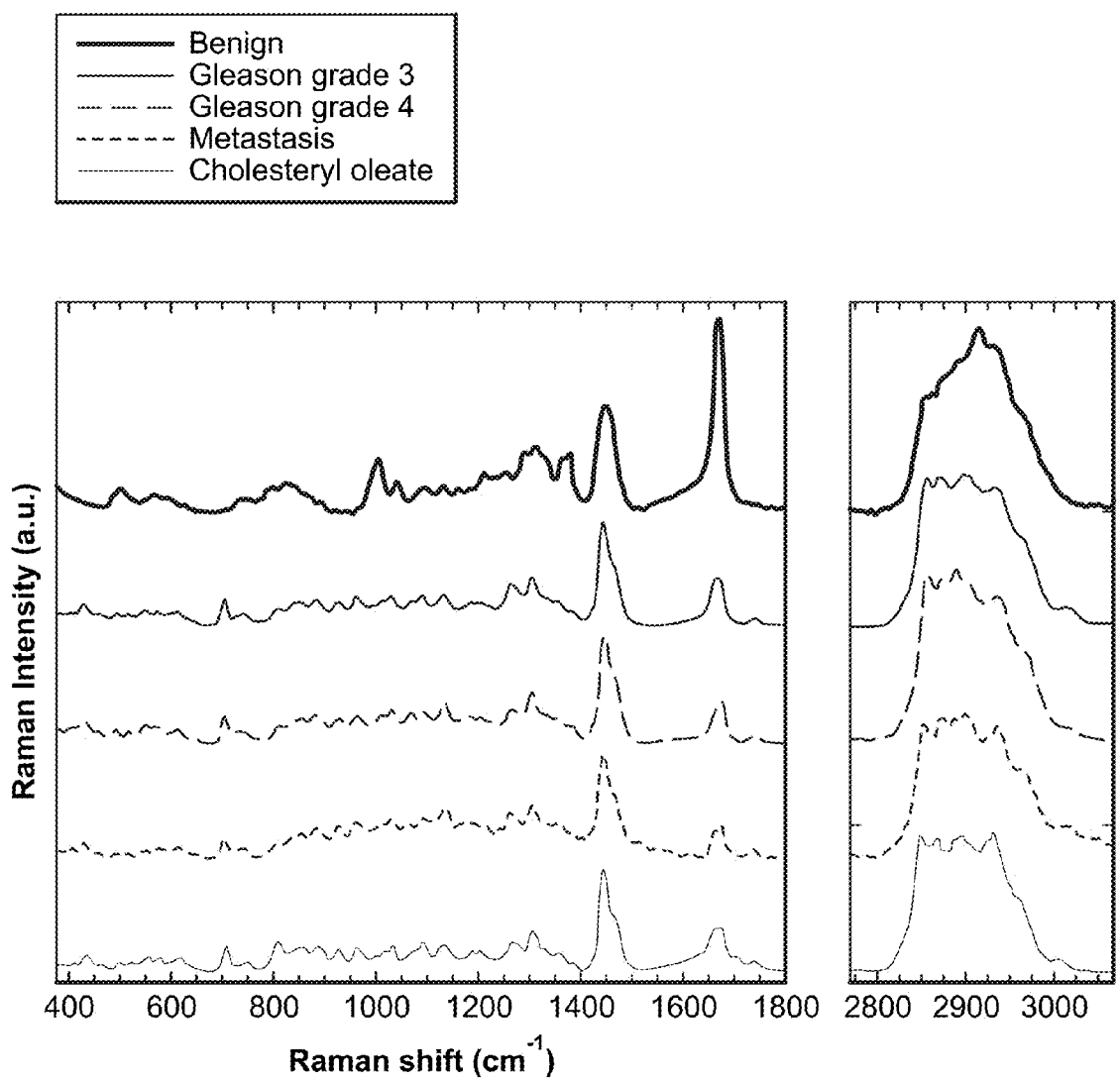
FIG. 23 shows representative spectra collected from benign prostate, Gleason grade 3, Gleason grade 4, and metastatic cancer.
Figure 24:
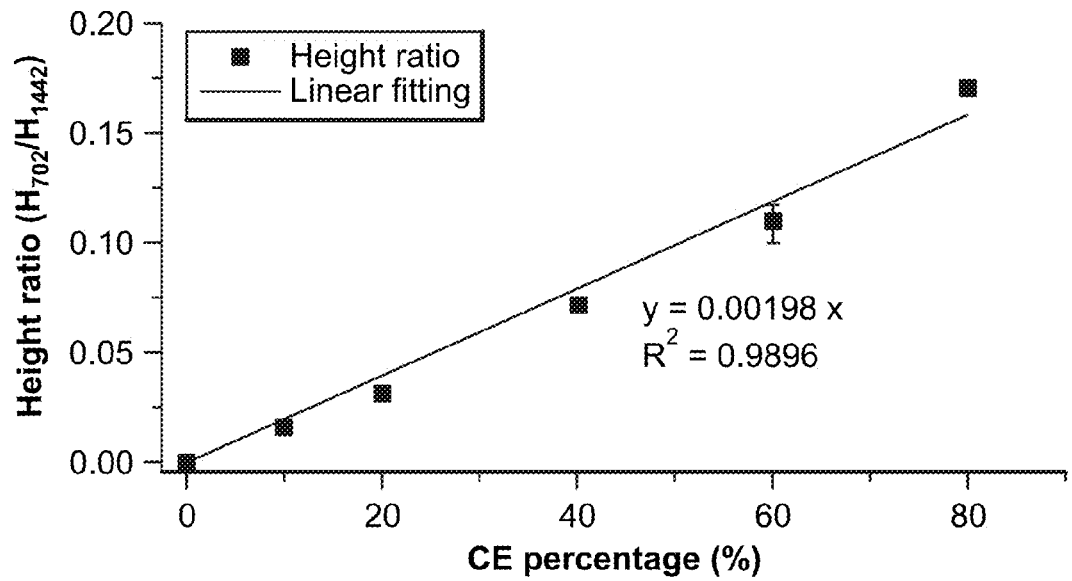
FIG. 24 is a graph showing the height ratio between the most prominent cholesterol band at 702 $cm^{-1}$ and the $CH_2$ deformation band at 1442 $cm^{-1}$.
Figure 25:
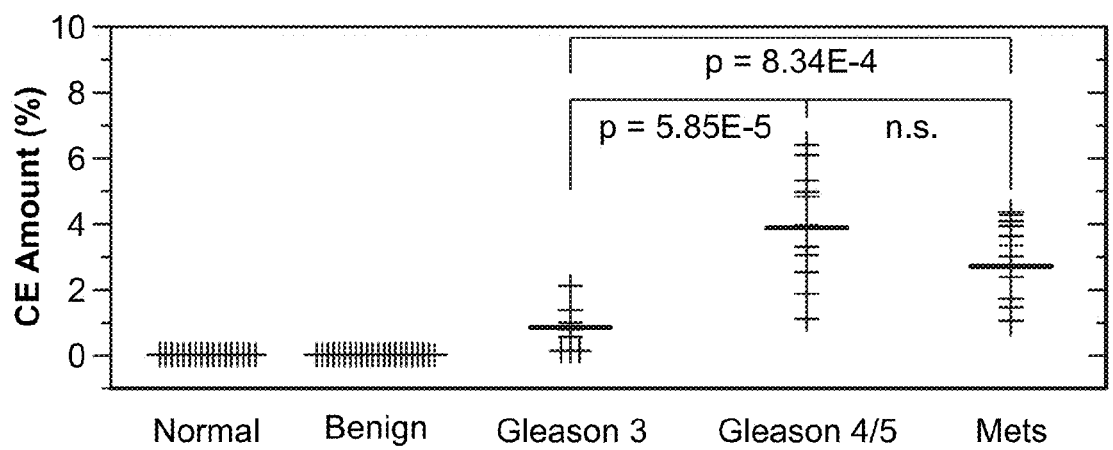
FIG. 25 is a graph showing cholesteryl ester amount in each of normal, benign, Gleason 3, Gleason 4/5, and mets tissue.

To evaluate the compositions of the lipids, we performed confocal Raman spectral analysis of individual autofluorescent granules or Lipid droplets accumulated in each lesion type. FIG. 23 shows representative spectra collected from benign prostate, Gleason grade 3, Gleason grade 4, and metastatic cancer. The autofluorescent granules seen in benign prostate consistently showed bands for lipid (1200-1800 $cm^{-1}$), phenylalanine (~1000 $cm^{-1}$) and prominent $CH_3$ stretching (~2930 $cm^{-1}$), but lacked the C=O ester stretching band at 1742 $cm^{-1}$. These data suggest that the autofluorescent granules are composed of unesterified lipids and proteins. Similar Raman profiles were seen in both normal prostate and PIN lesion. Importantly, the spectra of intracellular Lipid droplets in low-grade, high-grade, and metastatic prostate cancer (FIG. 23) were obviously different from those collected in normal, benign, and PIN lesions, but nearly identical to the spectrum of pure cholesteryl oleate (cyan line), with characteristic bands for cholesterol ring around 428, 538, 614 and 702 cm$^{-1}$ and for ester bond at 1742 cm$^{-1}$. Given that neutral lipids in Lipid droplets are predominantly triacylglycerol and cholesteryl ester, emulsions mixed of cholesteryl oleate and glyceryl trioleate were studied by Raman spectroscopy. It was found that the height ratio between the most prominent cholesterol band at 702 cm$^{-1}$ and the CH$_2$ deformation band at 1442 cm$^{-1}$ was linearly proportional to molar percentage of cholesteryl ester out of total lipids (FIG. 24). Based on this calibration curve, we found that lipid droplets were ubiquitously rich in cholesteryl ester in all types of cancer tissues, above 90% for low grade, high grade, and metastatic cancer. By large-area mapping and quantitation, the area fraction of cholesteryl ester rich lipid droplets was found to be 0.78±0.65% for low grade cancer, 3.93±1.74% for high-grade cancer, and 2.76±1.19% for metastatic cancer. The lipid droplet fraction was found significantly higher by ~5 folds (p=8.85E$^{-5}$) in high grade relative to low grade prostate cancers (FIG. 25).

Figure 26:
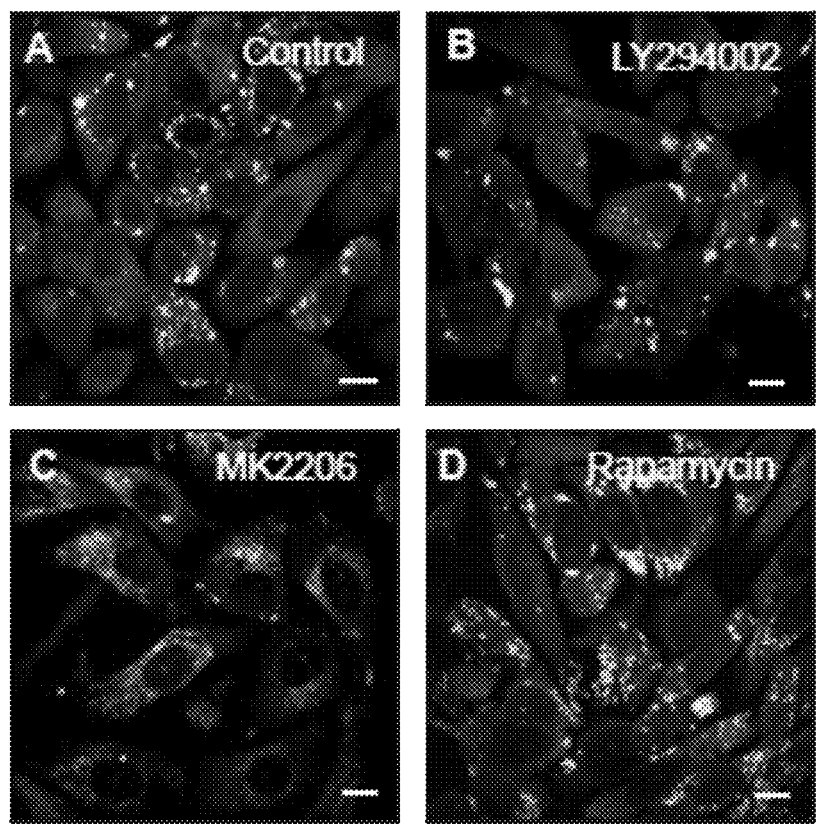
FIG. 26 is a set of images of lipid droplets in cells. Panel A is a control. Panel B shows cells treated with LY294002. Panel C shows cells treated with MK2206. Panel D shows cells treated with Rapamycin.
Figure 27:
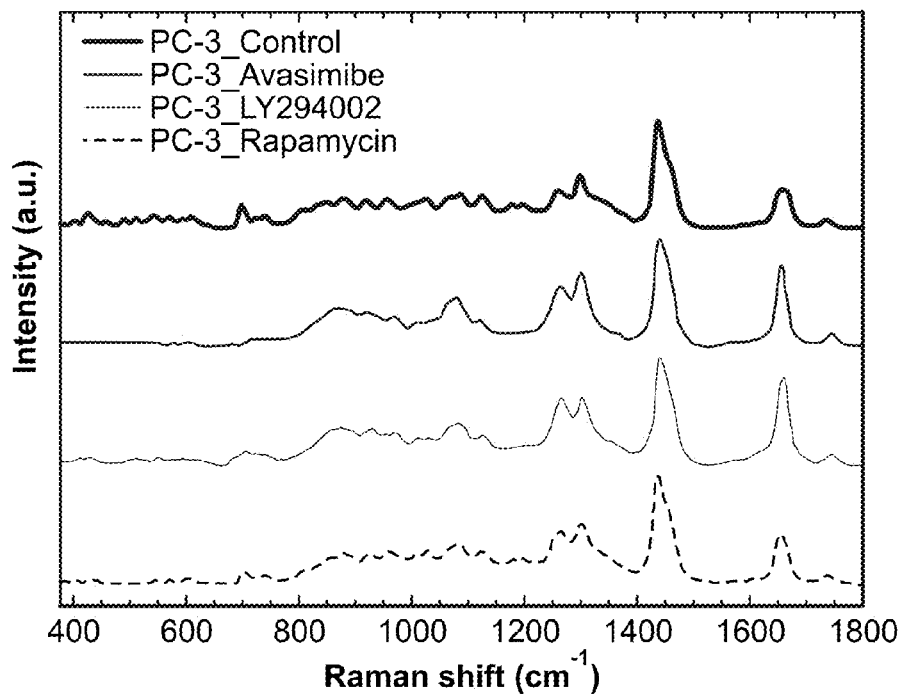
FIG. 27 is a set of Raman spectra of the different sets of cells from FIG. 26.

The data show that cholesteryl ester rich lipid droplets are abundant in high grade and metastatic prostate cancer, which prompted an investigation into the mechanism accounting for cholesteryl ester accumulation. A broad spectrum of human prostate epithelial cells has been examined. The data shows that cholesteryl ester accumulates in PC-3 (PTEN-negative) but not in DU145 (PTEN-positive), which led to examining whether cholesteryl ester accumulation is a result of upregulated PI3K/AKT/mTOR pathway. Loss of the tumor suppressor PTEN has been widely observed in both localized and metastatic prostate cancer and correlated with high Gleason grade. With loss of PTEN, PI3K signaling is hyper-activated, which, in turn, leads to AKT activation. The upregulated PI3K/AKT pathway has been increasingly implicated in proliferation, apoptosis, oncogenesis, and metastasis of prostate cancer. AKT mediates the phosphorylation and activation of mTOR complex 1 (mTORC1) which plays critical roles in the regulation of protein and lipid biosynthesis. To determine whether the PI3K/AKT/mTOR pathway regulates cholesteryl ester accumulation, both types of cholesteryl ester rich cell lines, PC-3 and high passage LNCaP (LNCaP-HP), were treated with LY294002 (PI3K inhibitor), MK2206 (AKT inhibitor), and Rapamycin (mTOR inhibitor), respectively. In LNCaP-HP cells, lipid droplets were completely eliminated by LY294002, and significantly reduced by Rapamycin. Moreover, cholesteryl ester percentage in the remaining lipid droplets was significantly reduced. In PC-3 cells, although lipid droplet amount was not much reduced upon LY294002 and Rapamycin treatments (FIG. 26, Panels A, B, and D), cholesteryl ester percentage was significantly reduced as shown by spectral analysis (FIG. 27). In both PC-3 and LNCaP-HP cells, MK2206 treatment not only radically removed lipid droplets (FIG. 26, Panel C) but also induced massive accumulation of autofluorescent granules indicative of autophagy.

Figure 28:
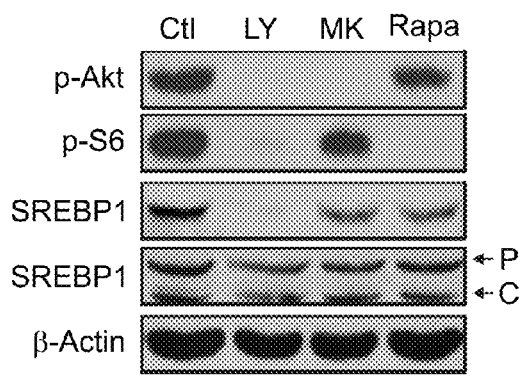
FIG. 28 is an immunoblot showing that inhibition of the PI3K/AKT/mTOR pathway suppressed the level of cleaved SREBP-1 but not SREBP-2 in PC-3 cells, indicating that cholesteryl ester storage is related to the cleavage of SREBP-1 isoforms.

It has been shown that mTOR plays a key role in regulating the function of sterol regulatory element-binding proteins (SREBPs) which control lipid and cholesterol homeostasis. Specifically, when cellular sterol levels decrease, SREBP-1a and/or -2 precursors are cleaved to activate the expression of genes involved in de novo cholesterol synthesis and LDL-cholesterol uptake. By using immunoblotting, the data show that inhibition of the PI3K/AKT/mTOR pathway suppressed the level of cleaved SREBP-1 but not SREBP-2 in PC-3 cells, indicating that cholesteryl ester storage is related to the cleavage of SREBP-1 isoforms (FIG. 28). Similar results for on LNCaP-HP cells were obtained. These results collectively suggest that cholesteryl ester accumulation is mediated by the PI3K/AKT/mTOR/SREBP activities.

Figure 29:
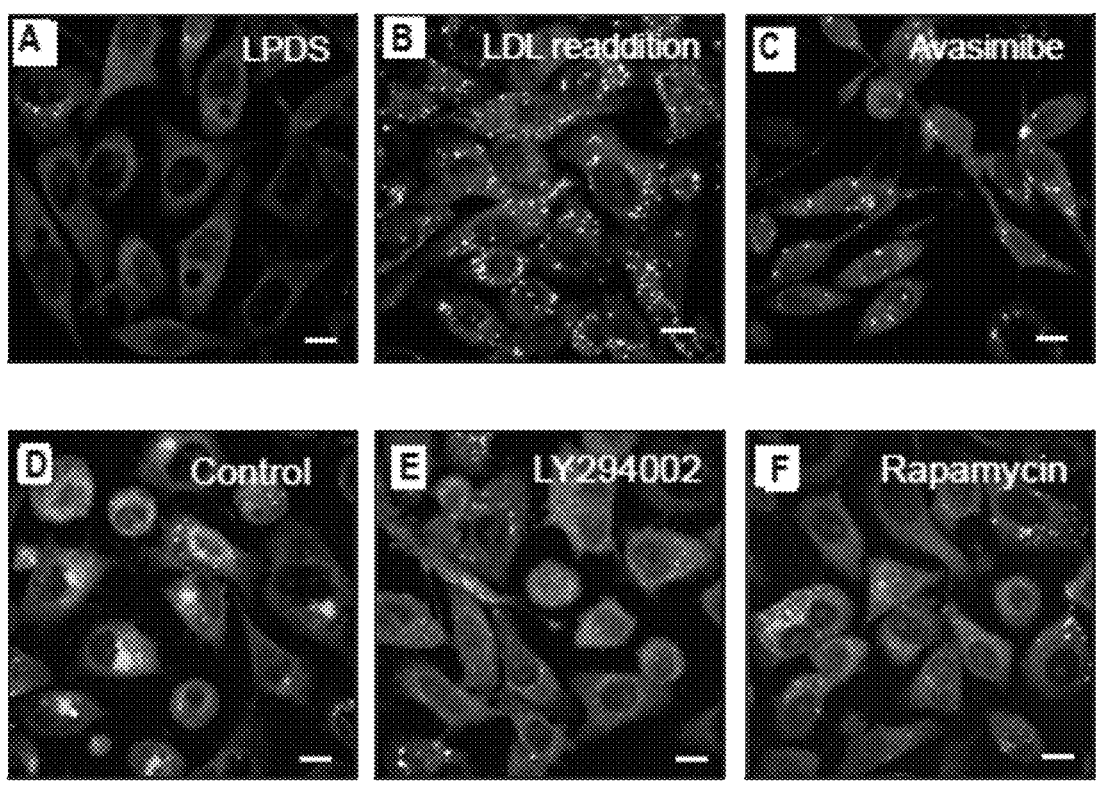
FIG. 29 is a set of images of lipid droplets in cells. Panel A shows cells treated with lipoprotein-deficient serum (LPDS). Panel B shows cells after re-addition of low-density lipoprotein (LDL) into the LPDS medium. Panel C shows cells treated with avasimibe. Panel D is a control and shows cells given only DiI-labeled LDL. Panel E shows cells treated with LY294002 and given DiI-labeled LDL. Panel F shows cells treated with rapamycin and given DiI-labeled LDL.
Figure 30:
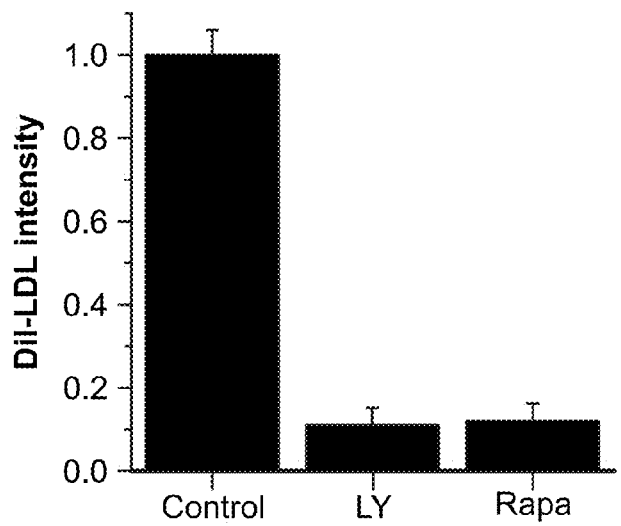
FIG. 30 is a graph showing DiI-LDL intensity in control cells, LY294002 treated cells, and rapamycin treated cells.

Because cholesterol can be either de novo synthesized via the mevalonate pathway or taken up from exogenous lipoproteins, the source of cholesterol used for cholesteryl ester accumulation was investigated. PC-3 cell were first treated with Simvastatin, an inhibitor of 3-hydroxy-3-methylglutaryl coenzyme A HMG-CoA reductase, the rate-limiting enzyme of the mevalonate pathway. Simvastatin neither decreased lipid droplet amount nor significantly reduced cholesteryl ester percentage in the lipid droplets. In contrast, after treating cells with lipoprotein-deficient serum (LPDS), lipid droplets nearly disappeared in cholesteryl ester rich PC-3 and LNCaP-HP cells (FIG. 29, Panel A), but remained the same amount in cholesteryl ester poor cells including LNCaP-LP, DU145, and C4-2. Re-addition of low-density lipoprotein (LDL) into the LPDS medium restored lipid droplets and cholesteryl ester in both PC-3 and LNCaP-HP cells (FIG. 29, Panel B). By treating cells with DiI-labeled LDL (DiI-LDL), it was found that LDL uptake was the most prominent in the cholesteryl ester rich PC-3 and LNCaP-HP cells among all the cell lines. Moreover, inhibition of the PI3K/AKT/mTOR pathway significantly blocked the uptake of DiI-LDL in PC-3 (FIG. 29, Panels C-F and FIG. 30). These results collectively indicate that exogenous LDL is the primary source for cholesteryl ester accumulation.

It is well known that LDL enters a cell via LDL receptor (LDLr) and traffics to the late endosome and lysosome where it is hydrolyzed to free fatty acids and free cholesterol. The excess free cholesterol together with the fatty acyl CoA substrate is then converted to cholesteryl ester by Acyl coenzyme A: cholesterol acyltransferase (ACAT) and stored in lipid droplets. Thus, cells were separately treated with Avasimibe and Sandoz 58-035, two different ACAT inhibitors. Both inhibitors effectively suppressed cholesteryl ester accumulation in PC-3 (FIG. 27) and LNCaP-HP cells, with amount of Lipid droplets remaining unchanged (FIG. 29, Panel C). The significant reduction of cholesteryl ester accumulation upon Avasimibe treatment was further confirmed by an independent biochemical assay of cell lysates.

Figure 31:
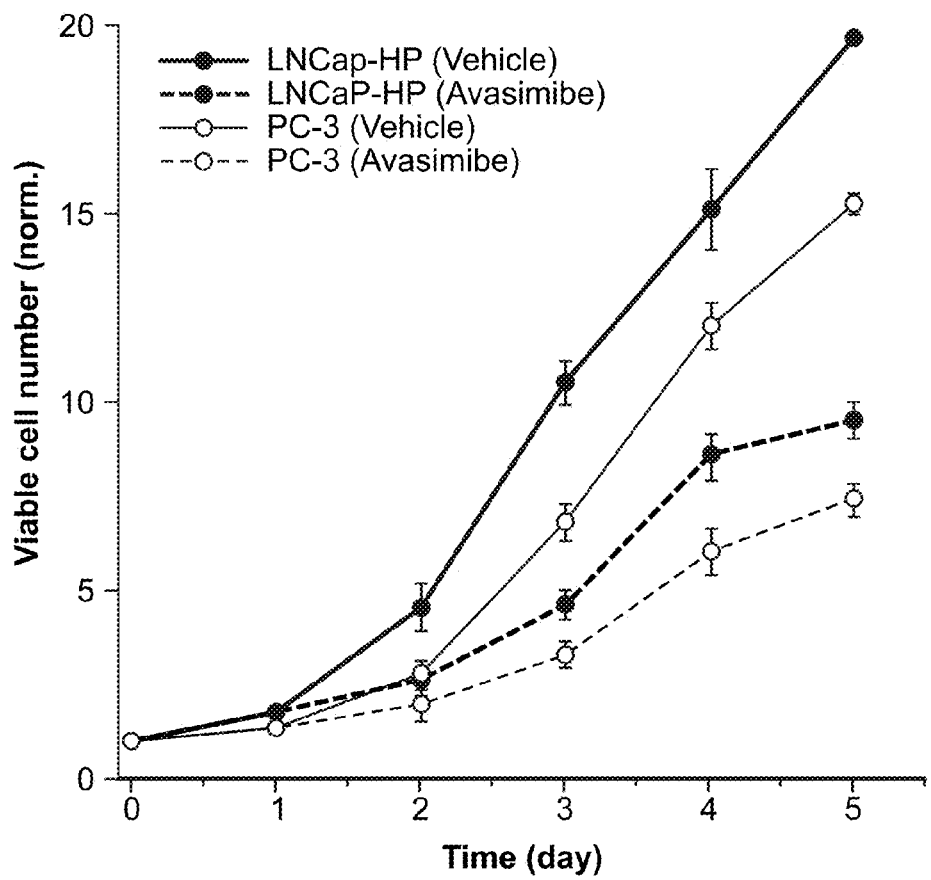
FIG. 31 is a graph showing viable cell numbers in control and avasimibe treated cholesteryl ester rich PC-3 and LNCaP-HP cells.
Figures 32A, 32B, 32C:
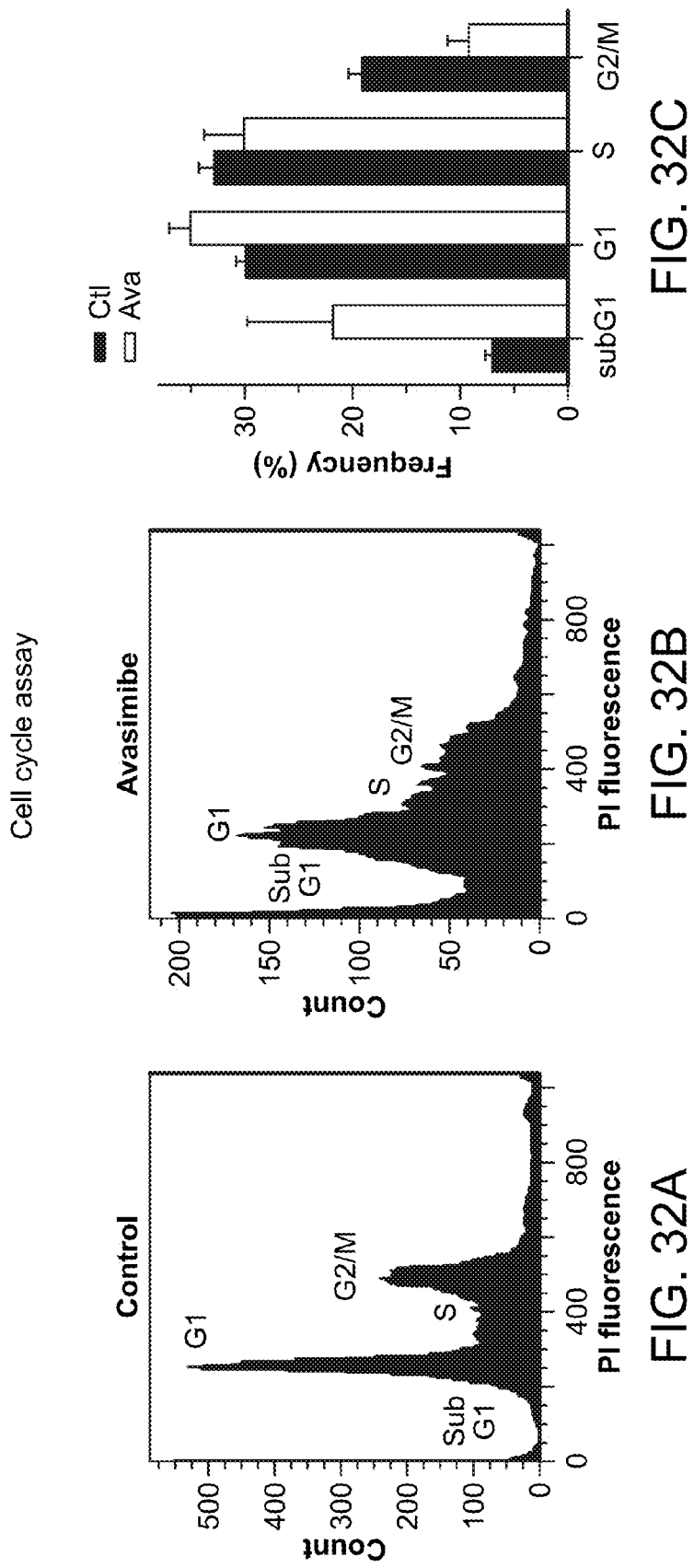
FIG. 32, Panels A-C show a flow cytometry analysis. The analysis reveals that exposure of PC-3 cells to Avasimibe resulted in both cell cycle arrest and apoptosis, i.e. the G2/M phase population was 2 times smaller whereas the sub G0/G1 population was ~3 times larger in Avasimibe-treated group compared to control group. Panel A is the control group. Panel B is the Avasimibe treated group. Panel C combines the control and the Avasimibe treated groups.

Because cholesteryl ester accumulation was found in PCa but not in normal prostate, how cell viability could be affected by regulating cholesteryl ester levels with the ACAT inhibitor Avasimibe was evaluated. As shown in FIG. 31, Avasimibe treatment significantly hampered the proliferation of cholesteryl ester rich PC-3 and LNCaP-HP cells. The inhibitory effect of Avasimibe on the growth of PC-3 and LNCaP-HP cells was considerably greater than that in cholesteryl ester poor cancer cells including LNCaP-LP, DU145, and C4-2. Specifically, around 48% and 55% reduction in viable cell number was detected in PC-3 and LNCaP-HP cells, respectively, upon 3 days of 7.5 µM Avasimibe treatment, resulting an IC50 value of 7.32 uM for PC-3 cell and 9.64 uM for LNCaP-HP cell. Flow cytometry analysis of the cells revealed that exposure of PC-3 cells to Avasimibe resulted in both cell cycle arrest and apoptosis, i.e. the G2/M phase population was 2 times smaller whereas the sub G0/G1 population was ~3 times larger in Avasimibe-treated group compared to control group (FIG. 32). At the same doses, no toxic effect on normal prostate RWPE1 cell was found. The data show that Avasimibe effectively and selectively inhibits the growth of the cholesteryl ester rich PCa cells by cell cycle arrest and apoptosis induction.

To test the potential of using Avasimibe to treat advanced PCa in vivo, Avasimibe (15 mg/kg body weight by i.p. injection) was administered to the mice bearing PC-3 xenografts.

Figure 33:
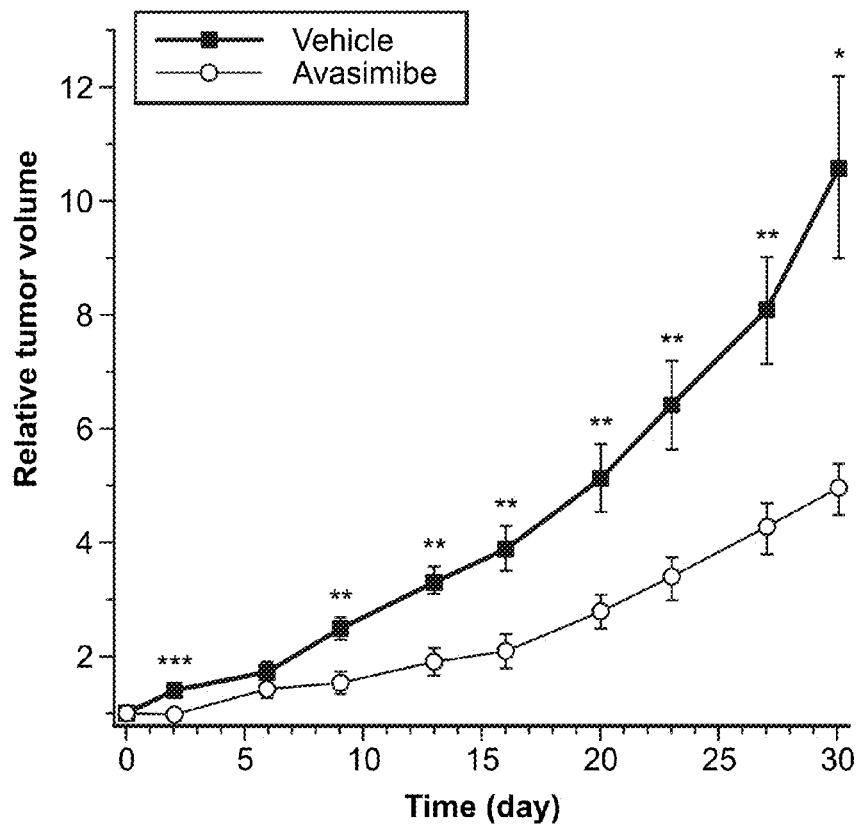
FIG. 33 is a graph showing that avasimibe administered to mice decreased tumor size compared to controls.
Figure 34:
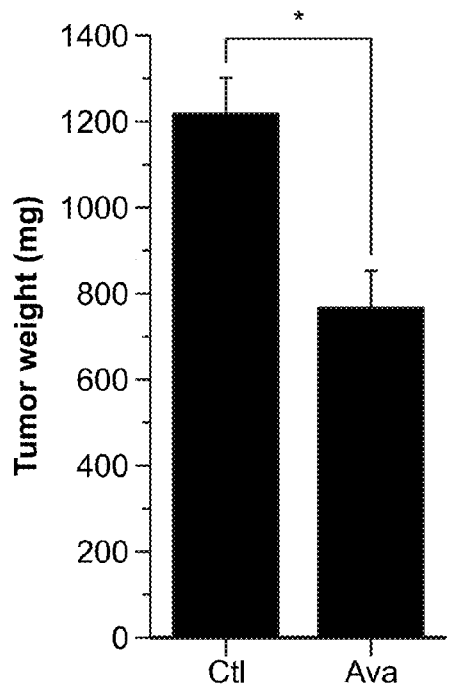
FIG. 34 is a graph showing that Avasimibe induced ~40% reduction in tumor weight by the end of 30-day treatment.
Figure 36:
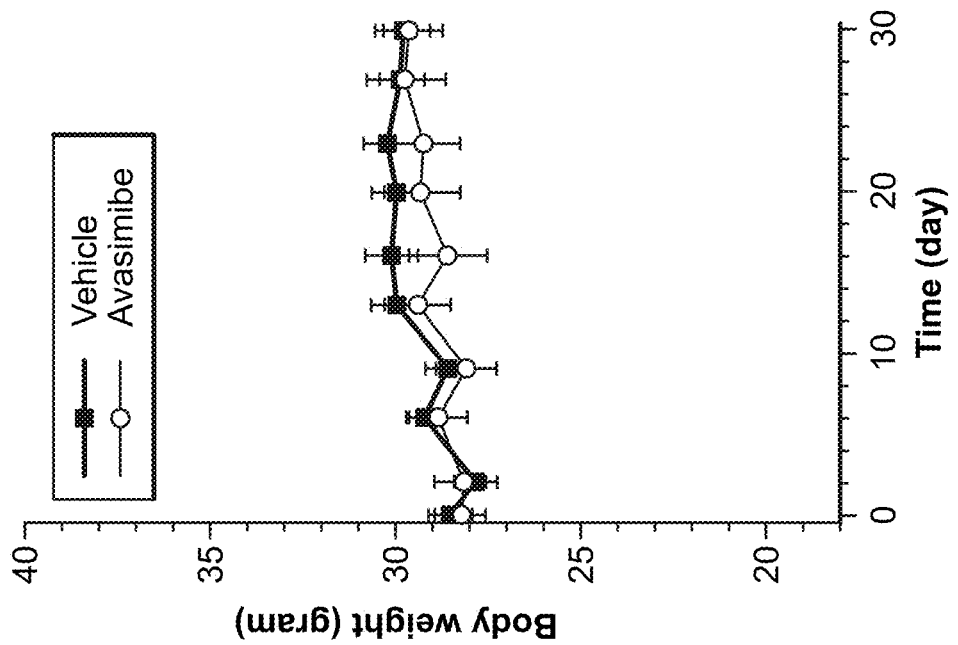
FIG. 36 is a graph showing that the body weight of control and avsimibe treated mice remained steady over the course of treatment.
Figure 35:
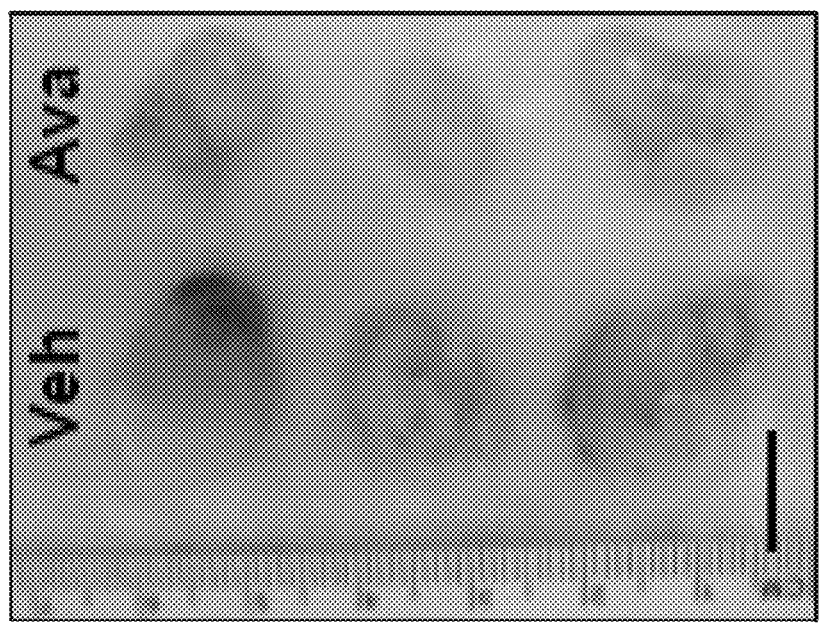
FIG. 35 is a photograph of harvested tumors from control and Avasimibe treated mice. Harvested tumors from animals treated with Avasimibe tended to be less bloody in appearance.
Figure 37:
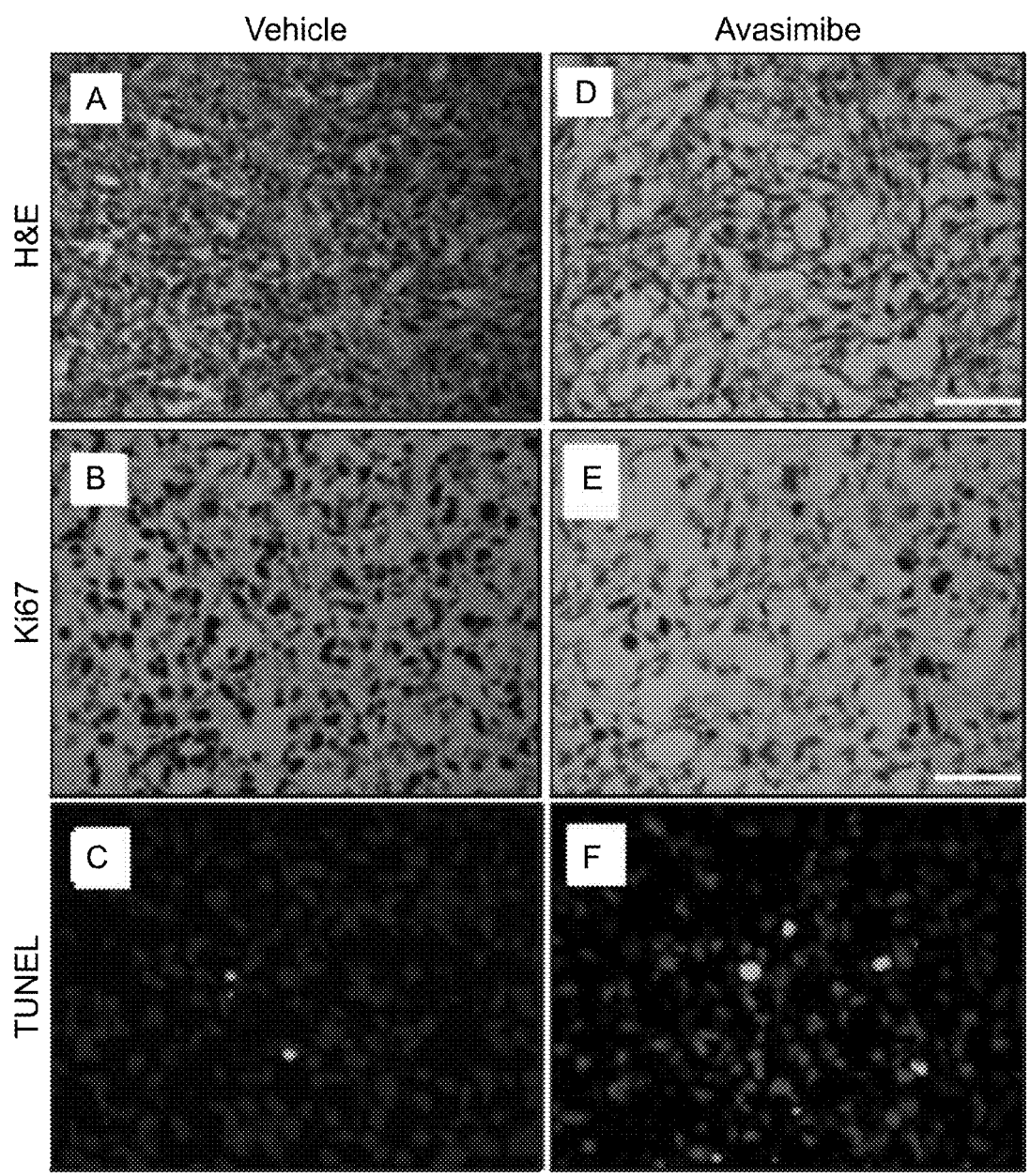
FIG. 37 is a set of photographs of cells containing lipid droplets. Panel A is cells treated with vehicle and shows H&E histology. Panel B is cells treated with vehicle and shows the proliferation marker Ki67. Panel C is cells treated with vehicle and shows apoptosis (TUNEL). Panel D is cells treated with Avasimibe and shows H&E histology. Panel E is cells treated with Avasimibe and shows the proliferation marker Ki67. Panel F is cells treated with Avasimibe and shows apoptosis (TUNEL).
Figures 38, 39:
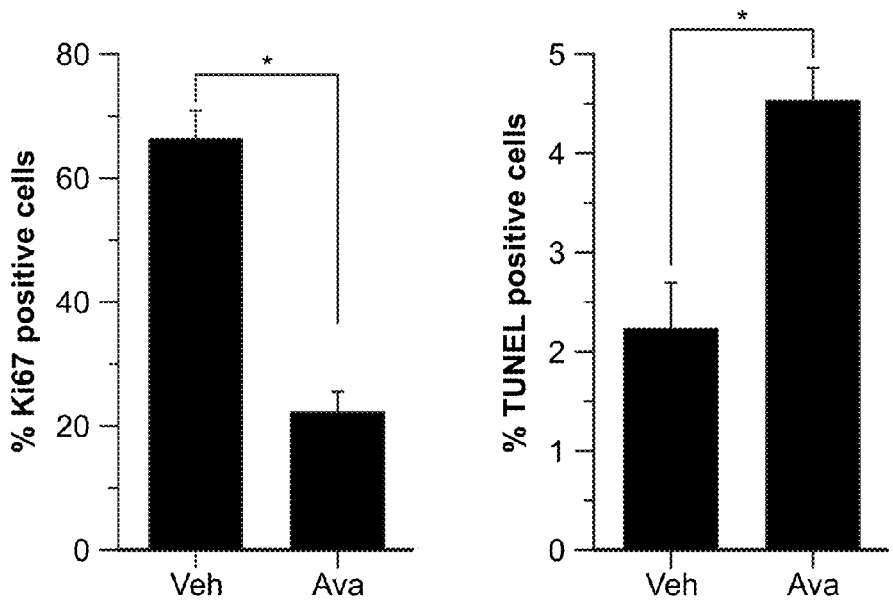
FIG. 38 is a graph showing the percentage of Ki67 positive cells treated with vehicle compared to the percentage of Ki67 positive cells treated with Avasimibe.
FIG. 39 is a graph showing the percentage of TUNEL positive cells treated with vehicle compared to the percentage of TUNEL positive cells treated with Avasimibe.

Daily treatment of mice with the Avasimibe inhibited the growth of PC-3 tumors by ~2 folds (FIG. 33), and induced ~40% reduction in tumor weight by the end of 30-day treatment (FIG. 34). Harvested tumors from animals treated with Avasimibe also tended to be less bloody in appearance (FIG. 35). Importantly, Avasimibe did not cause general toxicity to animals indicated by no change in animal behavior or body weight (FIG. 36). Spectroscopic imaging of extracted tissues revealed that cholesteryl ester content significantly dropped in Avasimibe-treated PC-3 tumor compared to vehicle-treated ones, indicating that Avasimibe worked to inhibit cholesteryl ester formation in tumor cells in vivo. Pathological review of sections of heart, kidney, liver, lung, and spleen harvested from mice receiving Avasimibe showed no signs of toxicity. Immunohistochemistry (IHC) using markers for proliferation (Ki67) and apoptosis (TUNEL) showed that Avasimibe significantly reduced proliferation by ~70% and increased apoptosis by ~2 folds (FIGS. 37-39). These results were consistent with the shrinkage of tumor size as well as the in vitro data of cell cycle arrest and apoptosis.

Figure 40:
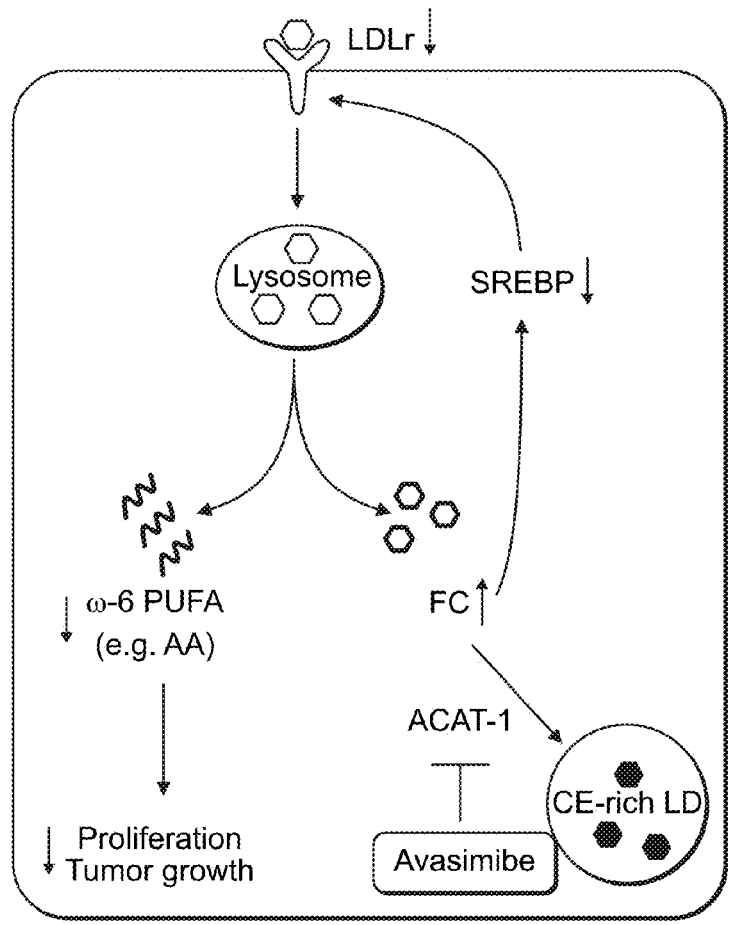
FIG. 40 is a diagram showing a proposed mechanism by which abrogating ACAT activity would up-regulate cellular level of free cholesterol and then down-regulate SREBP and LDLr in PCa cells.
Figure 41:
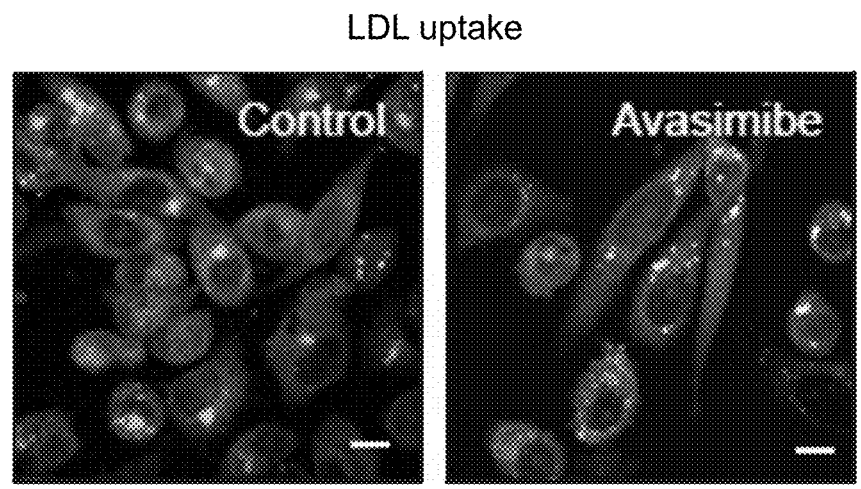
FIG. 41 is a set of images showing cellular uptake of DiI-labeled LDL. The panel on the left are control cells. The panel on the right are cells treated with Avasimibe.
Figure 42:
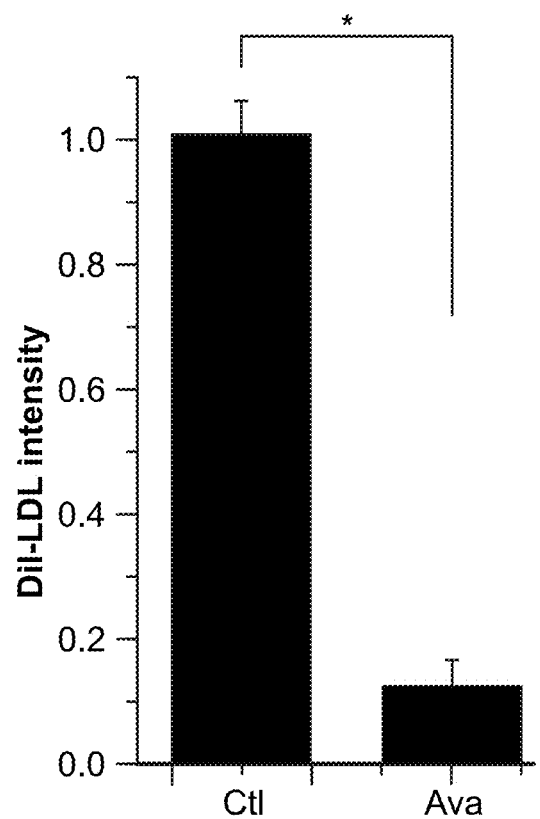
FIG. 42 is a graph showing DiI-LDL intensity for control and Avasimide treated cells.
Figure 43:
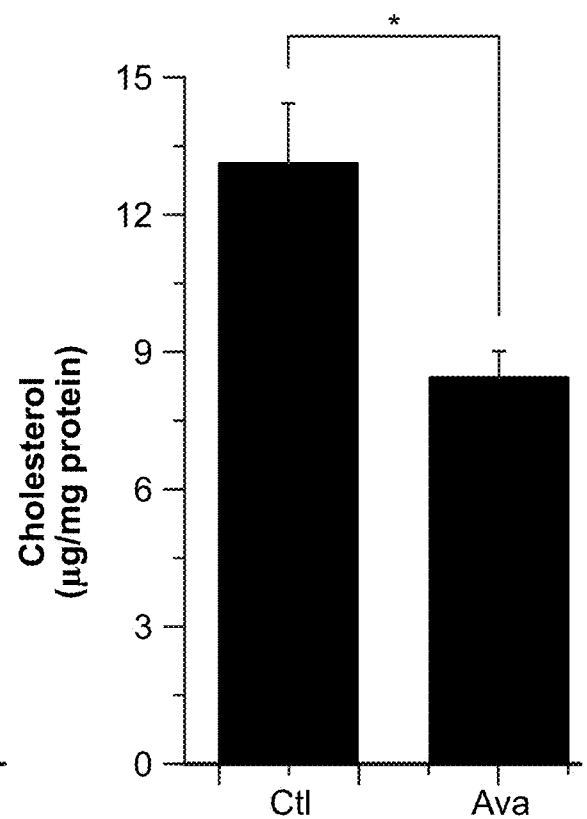
FIG. 43 is a graph showing the level of free cholesterol in control and Avasimibe treated cells.
Figure 44:
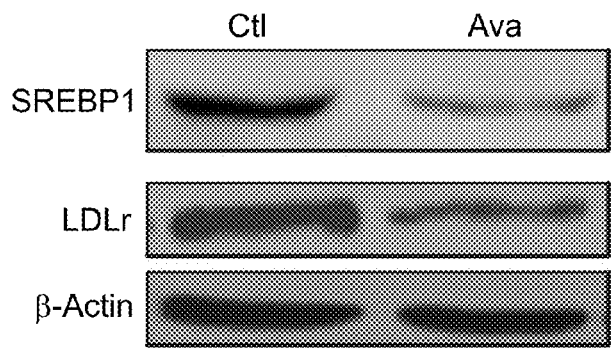
FIG. 44 is an immunoblot of control and Avasimibe treated cells. The blot shows that Avasimibe induced down-regulation of LDLr and SREBP-1
Figure 45:
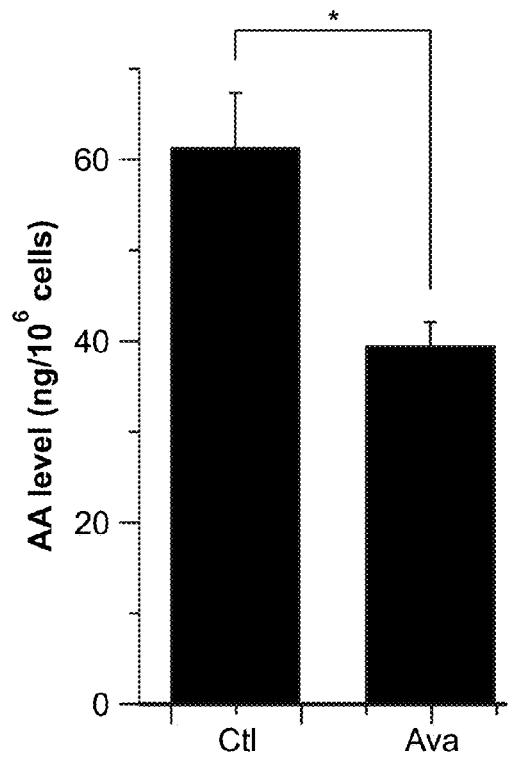
FIG. 45 is a graph showing AA levels in control and Avasimibe treated cells.
Figure 46:
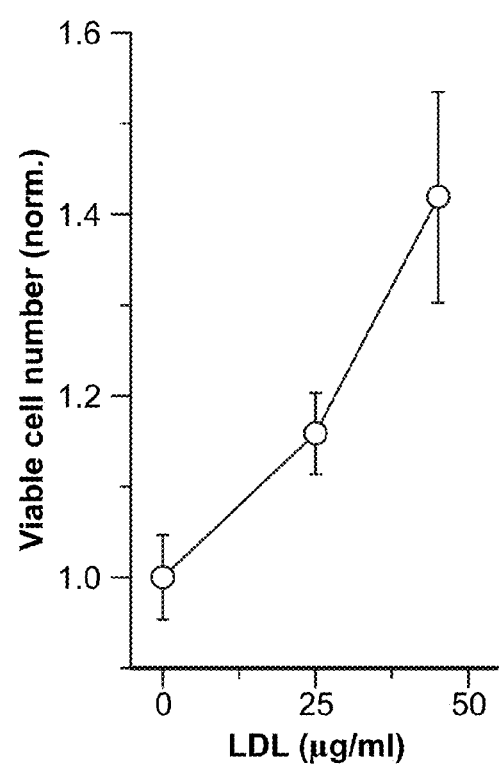
FIG. 46 is a graph showing viable cell number as compared to LDL.
Figure 47A:
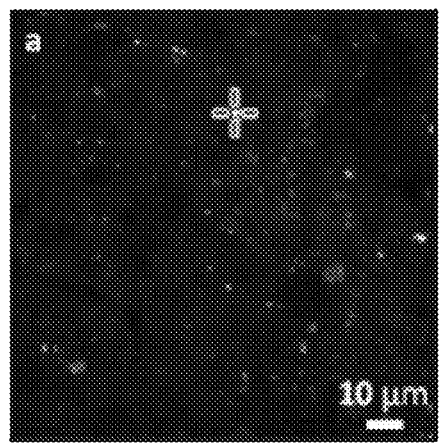
FIG. 47 Panels A-D show that Stimulated Raman scattering (SRS) imaging and Raman spectral analysis revealed lipid droplet and cholesteryl ester accumulation in human pancreatic cancer tissue. Panel A shows normal pancreatic tissue. Panel B shows pancreatic cancer tissue. SRS imaging were performed at a speed of 2 μs/pixel, using 665 nm as pump and 820 nm as stokes beam. Panel C shows Raman spectra acquired from the positions marked by crosses. Raman spectra were taken using a 707 nm laser as excitation source. The spectra were offset for clarity. Panel D is a graph showing that the height ratio of the peak at 702 $cm^{-1}$ to the peak at 1442 $cm^{-1}$ is proportional to cholesteryl ester percentage. Raman spectra used for analysis were taken from emulsified mixture of cholesteryl oleate and glyceryl trioleate (Sigma), which is to mimic the composition of intracellular lipid droplets.
Figure 47B:
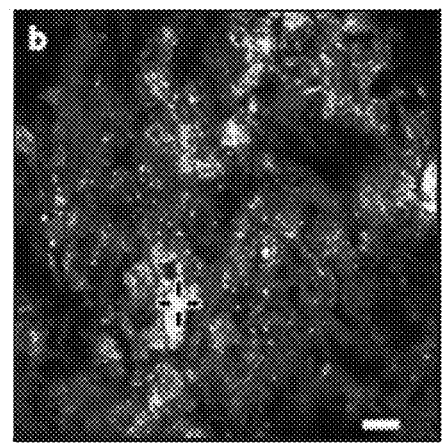
Figure 47C:
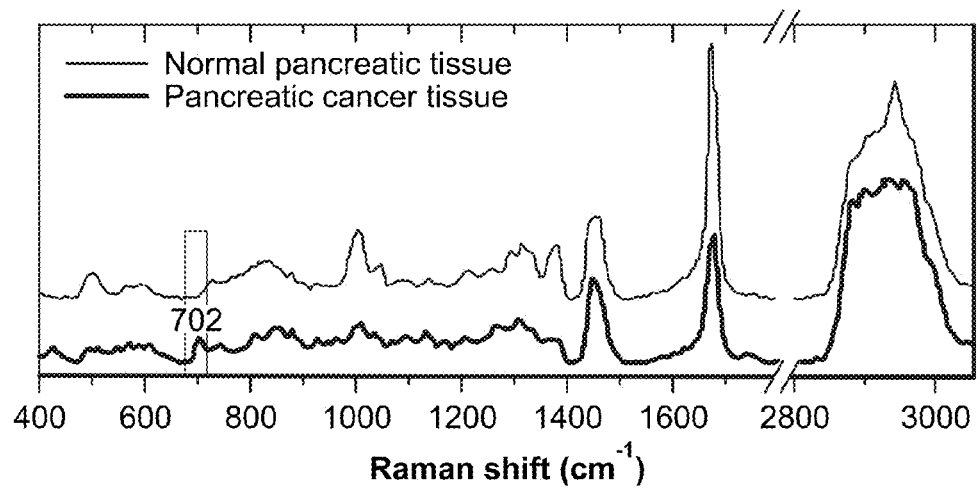
Figure 47D:
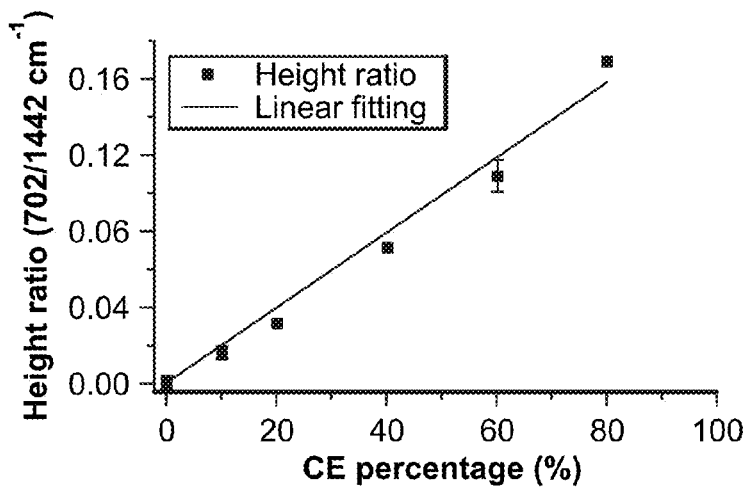

Finally, it was investigated whether Avasimibe-mediated suppression of tumor growth is associated with the regulation of cholesterol metabolism machinery. It was hypothesized that abrogating ACAT activity would up-regulate cellular level of free cholesterol and then down-regulate SREBP and LDLr in PCa cells (FIG. 40). To test this hypothesis, cellular uptake of DiI-labeled LDL was first monitored upon 2-day Avasimibe treatment, and it was found that Avasimibe drastically inhibited LDL uptake in PC-3 (FIGS. 41-42) as well as in LNCaP-HP cells. Using a standard biochemical assay, it was found that 2-day Avasimibe treatment reduced the level of CE but slightly increased the level of free cholesterol in PC-3 (FIG. 43). Furthermore, immunoblotting measurement showed that Avasimibe induced down-regulation of LDLr and SREBP-1 for PC-3 (FIG. 44), and of LDLr and SREBP-2 for LNCaP-HP. These data show that Avasimibe blocks cholesteryl ester accumulation via decreased uptake of LDL-cholesterol. To provide an explanation for enhanced uptake of LDL and then storage of excess cholesterol in the form of cholesteryl ester in aggressive prostate cancer, it was noticed that LDL is the primary carrier of essential polyunsaturated fatty acid including arachidonic acid (AA). Inside cells, AA is converted to a wide range of eicosanoids, which have been implicated in various pathological processes such as inflammation and cancer. LC-MS data of PC-3 cell lysates revealed that Avasimibe significantly reduced the level of AA (FIG. 45). As independent evidence, it was shown elsewhere and reported here that LDL (FIG. 46) and AA promoted the growth of PC-3 cells in a dose-dependent manner. These data collectively show that Avasimibe hindered proliferation of cholesteryl ester rich prostate cancer cells by limiting the uptake of a critical proliferative factor, AA, via down-regulation of LDLr.

In summary, the data herein show that cholesteryl ester is a marker for molecular differentiation between low grade and high grade prostate cancer. The data also show that abrogating the cholesterol metabolism selectively inhibits cell growth and induces cell death in late stage prostate cancer.

Example 21

Pancreatic Cancer

The pancreas is a unique organ that has both exocrine and endocrine compartments. These compartments are responsible for production of digestive enzymes and hormones that regulate two important physiological processes: digestion and glucose metabolism. Pancreatic cancer is the fourth leading cause of cancer-related death in the United States, with a 5-year survival rate of only about 4%. In 2012, there were estimated 43,920 new cases and 37,390 deaths related to pancreatic cancer. More than 90% of cases arise from the exocrine portion of the pancreas and are pancreatic ductal adenocarcinomas. Due to lack of early cancer-related symptoms, patients with pancreatic cancer are often diagnosed at an advanced stage. So far, Gemcitabine, a deoxycytidine analogue, is the standard chemotherapy treatment for advanced pancreatic cancer. Gemcitabine with erlotinib, an epidermal growth factor receptor tyrosine kinase inhibitor, is the only FDA-approved combination treatment. Gemcitabine can directly incorporate into DNA, inhibiting ribonucleotide reductase to prevent DNA replication and, thus, tumor cell growth. However, almost all patients either have primary or eventually gain secondary resistance to gemcitabine treatment. Gemcitabine plus erlotinib has a modest effect, which can only prolong median overall survival for less than 2 weeks. The reasons for chemoresistance to gemcitabine are still under investigation. This gap raises a critical need for developing new pancreatic cancer treatment strategies.

Apparatuses of the invention offer the capability of quantifying both the amount and the composition of lipids inside single cells. By combination of label-free imaging and standard biochemistry methods, it is expected that pancreatic cancer progression is partly driven by elevated and activated lipid pathway molecules such as SREBPs, fatty acid synthase, HMGCoA reductase and LDL receptors. This knowledge will be significant because it open new opportunities for treating advanced pancreatic cancer by targeting the altered lipid metabolism.

The data herein show the accumulation of lipid droplets in pancreatic cancer tissues but not in normal pancreatic tissues. Spectral analysis showed that these lipid droplets contain over 80% cholesteryl ester. The data further show that avasimibe, a potent ACAT inhibitor, reduced the lipid droplet amount in BxPC3 cells and eliminated cholesteryl ester in PANC-1 cells. More importantly, avasimibe significantly reduced the viability of both cell lines.

Coherent Raman scattering (CRS) microscopy is a label-free imaging technique that is highly sensitive to C—H bond abundant structures such as membranes and lipid droplets. By matching the C—H bond stretching vibration mode at 2850 $cm^{-1}$, lipid distribution was imaged in human pancreatic cancer (n=10) and normal tissues (n=10) provided by IU School of Medicine. A remarkable amount of lipid droplets in all pancreatic cancer tissues was observed (FIG. 47, Panel B). In contrast, the lipid bodies in normal pancreatic tissues (FIG. 47, Panel A) were found to be autofluorescent and assigned as lipofuscin. Furthermore, by coupling a spectrometer to the CRS microscope, the devices was able to dissect the composition of individual lipid droplets through confocal Raman spectral analysis. The Raman spectra taken from the lipid droplets (FIG. 47, Panel C) showed that the lipid droplets in pancreatic cancer contain high level of cholesteryl ester, indicated by the characteristic cholesterol ring vibration mode (702 $cm^{-1}$). Using emulsified mixtures of cholesteryl oleate and glyceryl trioleate (Sigma), it was verified that height ratio of the Raman peak at 702 $cm^{-1}$ the Raman peak at 1442 $cm^{-1}$ ($CH^2$ bending vibration mode) is linearly proportional to molar percentage of cholesteryl ester (FIG. 47, Panel D) out of the total neutral lipids. Based on this calibration curve, it was concluded that over 80% of neutral lipids in human pancreatic cancer tissues are cholesteryl ester.

Figure 48A:
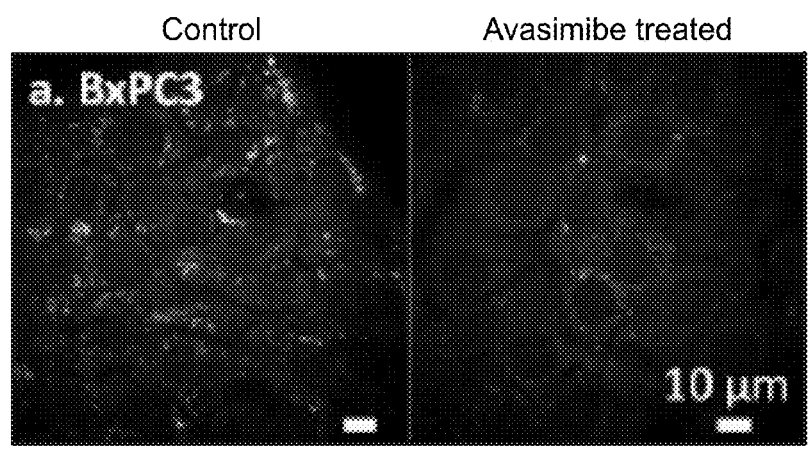
FIG. 48 Panels A-C show that Avasimibe treatment (7.5 μM for 24 h) reduced lipid droplet amount in BxPC3 cells and blocked cholesteryl ester accumulation in PANC-1 cells. Panels A and B show Coherent Raman scattering images of BxPC3 and PANC-1 cells, respectively. Panel C shows Raman spectra taken from lipid droplets in PANC-1 cells at marked positions. The peak at 702 $cm^{-1}$ disappeared after treatment.
Figure 48B:
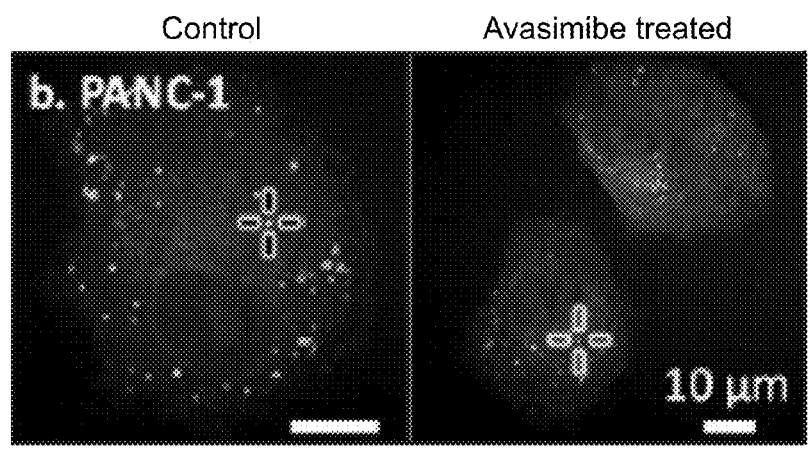
Figure 48C:
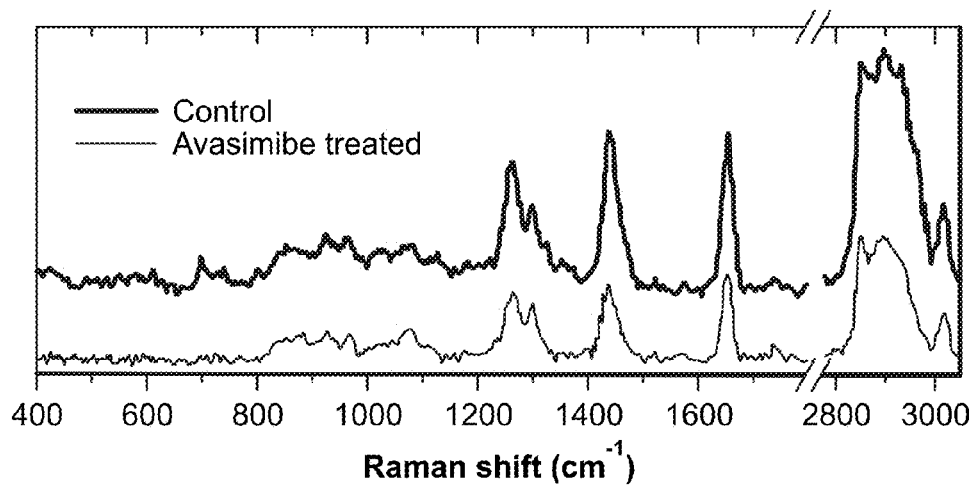
Figure 49:
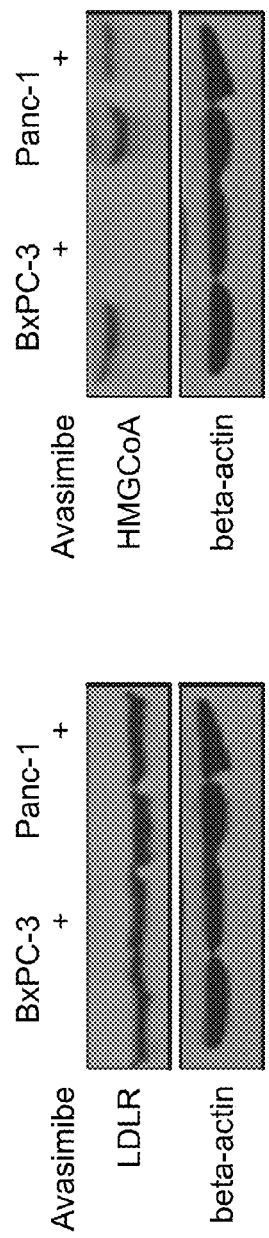
FIG. 49 is a set of immunoblots showing that Avasimibe treatment significantly reduced the level of HMGCoA reductase, but not the LDL receptor.

In order to understand how lipids accumulate in pancreatic cancer, several in vitro studies using two common pancreatic cancer cell lines, BxPC3 and PANC-1 were performed. Since ACAT is the enzyme responsible for the conversion from cholesterol to cholesteryl ester the effects of inhibiting ACAT-1, the universally expressed isoform, on lipid metabolism in pancreatic cancer cells were first examined. Using CRS microscopy and Raman spectroscopy, it was observed that an ACAT-1 inhibitor, avasimibe, significantly reduced the amount of lipid droplets in BxPC3 cells (FIG. 48, Panel A) and blocked cholesteryl ester accumulation in PANC-1 cells (FIG. 48, Panels B-C). These results show that ACAT-1 plays an important role not only in regulating cholesterol hemostasis, but also in modulating lipid accumulation in pancreatic cancers, which might be achieved via some crosstalk pathways. To explore the molecular mechanism, western blot of the cells before and after avasimibe treatment were performed. FIG. 49 shows that avasimibe reduced the expression of HMGCoA reductase, whereas the LDL receptor was not affected. These data show that cholesteryl ester results from de novo cholesterol synthesis.

Figure 50A:
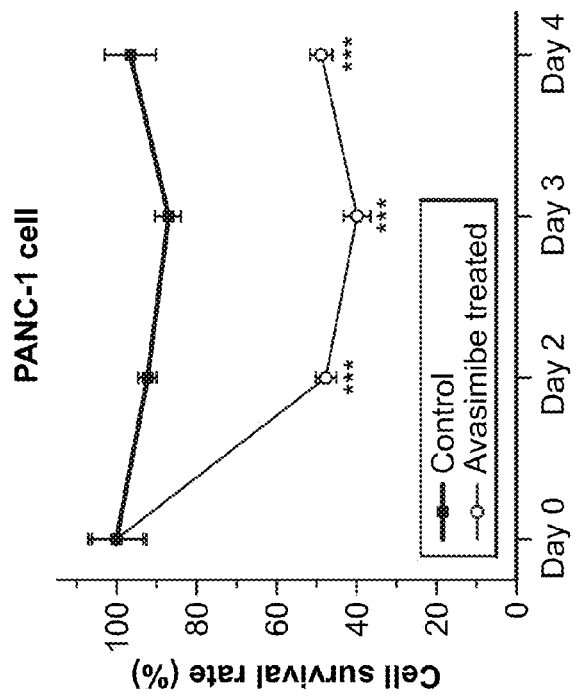
FIG. 50 Panels A-B is a set of graphs showing that Avasimibe treatment significantly reduced cell viability of pancreatic cancer cells. The graph in Panel A shows BxPC3 cells. The graph in Panel B shows PANC-1 cell. The cells were treated with vector (control) or 7.5 μM avasimibe for various periods. Then cells were lysed and ATP level were quantified to determine the number of viable cells.
Figure 50B:
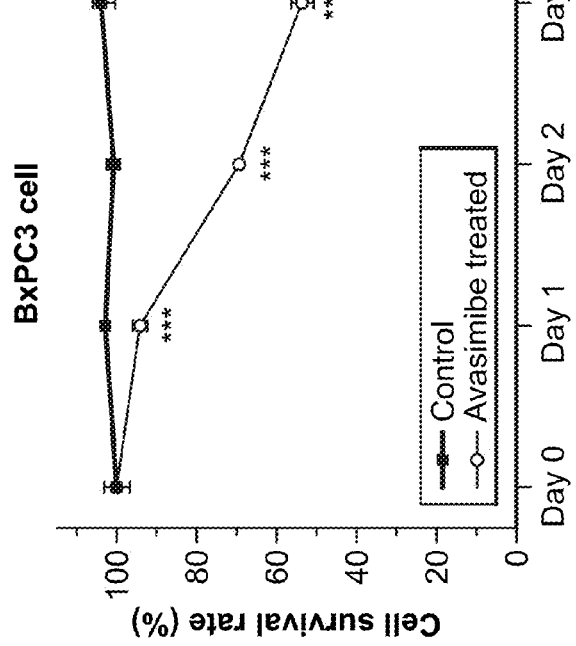

As the ACAT-1 inhibitor, avasimibe, effectively removed lipid droplet or cholesteryl ester accumulation in pancreatic cancer cells, the use of avasimibe as a chemotherapy agent for pancreatic cancer was explored. The effects of avasimibe on cell viability in BxPC3 and PANC-1 cells were examined. As expected, avasimibe treatments dramatically reduced the cell viability in both cell lines (FIG. 50).

The data herein show aberrant cholesteryl ester accumulation in pancreatic cancer, and show that avasimibe is a promising therapeutic agent for pancreatic cancer.

Example 22

VPAT Endoscope

Spectroscopic signals from inherent molecular vibration offer a contrast mechanism for label-free imaging of biomolecules in cells and tissues. Vibrational imaging of deep tissues holds great potential for in situ diagnosis based on the disrupted molecular mechanism in human diseases. However, vibrational imaging of deep tissues has been a formidable challenge due to tissue absorption and scattering of both incident photons and generated signals. Consequently, though coherent Raman scattering microscopy has allowed fast vibrational imaging, its penetration depth is limited to c.a. 100 μm because the signal is generated by ballistic photons under the tight focusing condition. This Example shows a platform that enables vibrational imaging of biological tissues beyond the ballistic regime. This platform, termed as vibration-based photoacoustic tomography (VPAT), is based on diffused photon excitation of harmonic vibration of chemical bond (i.e., overtone transitions from n=0 to 2, 3 . . . ) in the near infrared region, inherent relaxation of vibrational energy into heat, and acoustic detection of the generated ultrasound waves from the object.

The apparatus herein is based on vibrational photoacoustic microscopy, where a weakly focused near infrared nanosecond laser is used to induce an overtone transition in a specimen, and a focused transducer is employed to detect the acoustic signal in the forward direction. Under the microscopic condition, the photoacoustic signal is produced by the focused photons. Thus, the imaging speed is limited by slow lateral scanning. In contrast, signals in the proposed VPAT technology are produced by diffused photons, where the imaging speed is significantly increased by ultrasonic array detection and the imaging depth is determined by tissue absorption which has a mean absorption length of 1.0 to 10 cm in the near infrared region. The VPAT device uses a laser that is briefly described here and further described in the following Examples. Briefly, the laser in the VPAT device is a Raman laser that converts the 1064 nm pulses of a Nd:YAG laser to pulses at 1197 nm with a 36% conversion efficiency. The VPAT device is able to reach an imaging depth of ~5 cm and 3-D spatial resolution on the order of ~100 μm.

Figure 51:
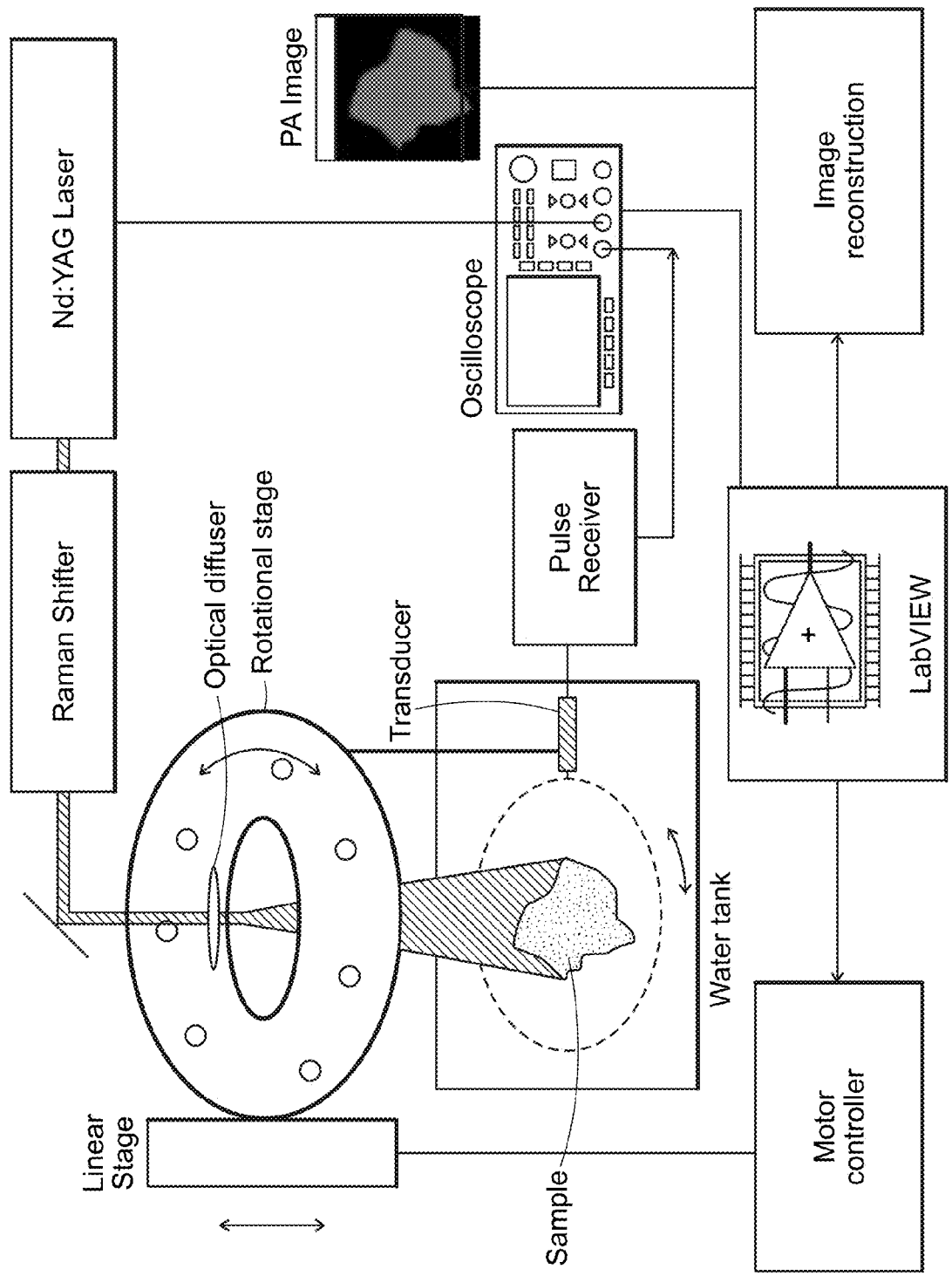
FIG. 51 is a schematic of a single-transducer VPAT imaging system.

A schematic of the VPAT imaging system with a single element transducer is given in FIG. 51. The Raman laser provides the excitation source for the 1st C—H overtone transition. The light illuminates the sample after passing through the central hole of a rotational stage in which a single element transducer facing the sample is attached. The sample is placed inside a water proof gelatin gel. To provide acoustic coupling, both the transducer and the sample are placed in a water bath. The transducer is rotated in a circular path on a plane passing through the sample. The transducer records the photoacoustic signal and its output is amplified by a pulser/receiver (Panametrics). The amplified signal is then fed into a channel of a digital oscilloscope (Tektronix) triggered by the Nd:YAG laser. For each laser firing, the photoacoustic signal will be acquired and stored on the computer with a program written in LabView. After the acquisition of the first data, the transducer will be rotated by 2° and the next data will be acquired. This will be repeated until the 360° angle is covered.

The data acquired in one complete revolution will be used to construct the 2-D images with a standard algorithm. In order to obtain 3-D images, the rotational stage is attached with a linear stage. For each position of the transducer along the Z-axis above and below the plane passing through the center of the sample, the circular scan will be performed. Then the 3-D images are constructed through layer by layer stacking of the 2-D images.

Example 23

Laser

This Example describes an approach to efficiently shift the wavelength of a Nd:YAG laser with a homebuilt solid-state Raman laser. The Raman laser, also called Raman shifter, is based on the process of stimulated Raman scattering in a gain medium. The output wavelength of a Raman laser is determined by the pump wavelength and Raman shifts of the medium. By virtue of excellent properties, $Ba(NO_3)_2$ crystal-based Raman lasers have been reported in a lot of literature. The $Ba(NO_3)_2$ crystal is an isotropic material with cubic symmetry. Its Raman spectrum is dominated by a strong peak at 1047 $cm^{-1}$, which corresponds to the "breathing" mode of the $NO_3$ molecular group. At room temperature, the Raman gain coefficient of $Ba(NO_3)_2$ crystal is 11 cm/GW, pumped by 1064 nm Nd:YAG laser. The optical damage threshold is ca. 400 $MW/cm^2$. The Example shows the construction and use of a $Ba(NO_3)_2$ crystal-based Raman laser for vibration-based photoacoustic imaging. Using a 10-Hz Nd:YAG laser as the pumping source, up to 21.4 mJ pulse energy at 1197 nm was obtained, corresponding to the conversion efficiency of 34.8%. Photoacoustic imaging of intramuscular fat sample was performed to prove the concept of using a Raman laser to map lipid distribution in biological tissues.

Figure 52:
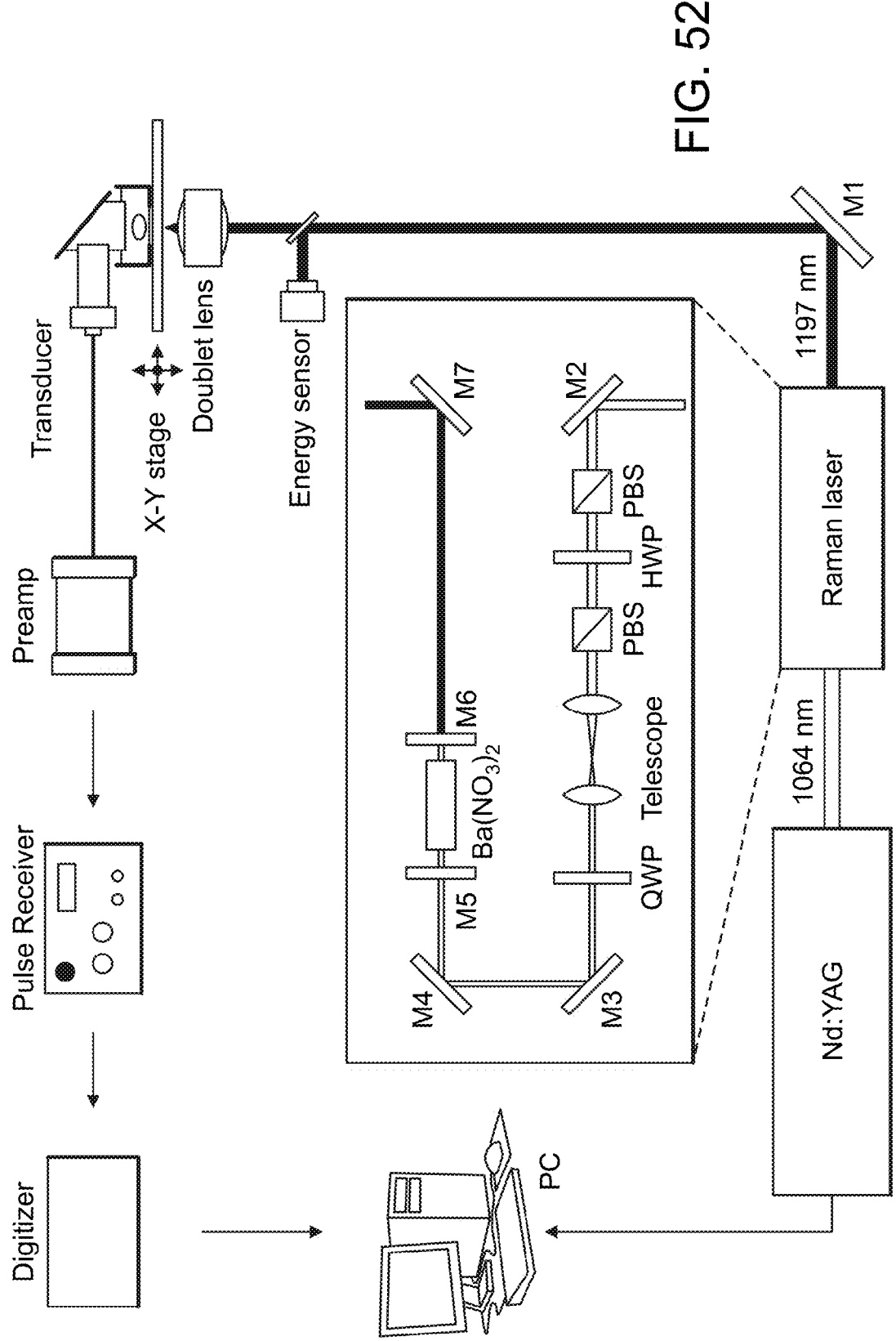
FIG. 52 is a schematic of a photoacoustic microscope equipped with a $Ba(NO_3)_2$ crystal-based Raman laser. $M_L$, $M_2$, $M_3$, and $M_4$: 45° 1064 nm reflective mirror. PBS: polarizing beam splitter. HWP: half wave plate. QWP: quarter wave plate. $M_5$: resonator end mirror. $M_6$: output coupler. $M_7$: silver mirror. PC: computer.
Figure 53A:
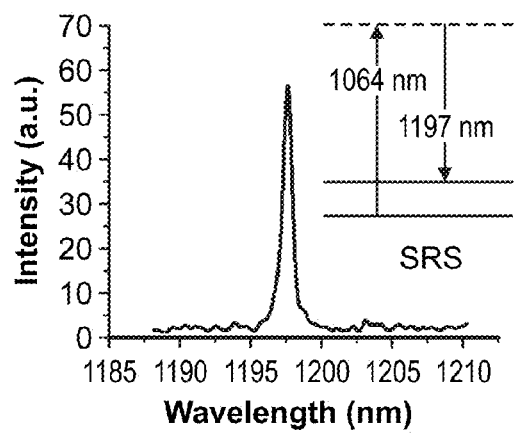
FIG. 53, Panels A-D show characteristics of the $Ba(NO_3)_2$ crystal-based Raman laser. Panel A shows the spectral profile of the Raman laser output. Panel B shows the 1st Stokes energy as a function of the pump energy incident on the Raman crystal. Red solid line is a linear fit. Panel C shows conversion efficiency with respect to the pump intensity incident on the Raman crystal. Panel D shows pulse energy of Raman laser as a function of time.
Figure 53B:
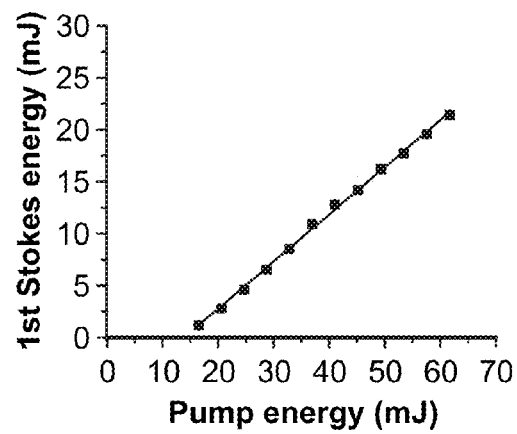
Figure 53C:
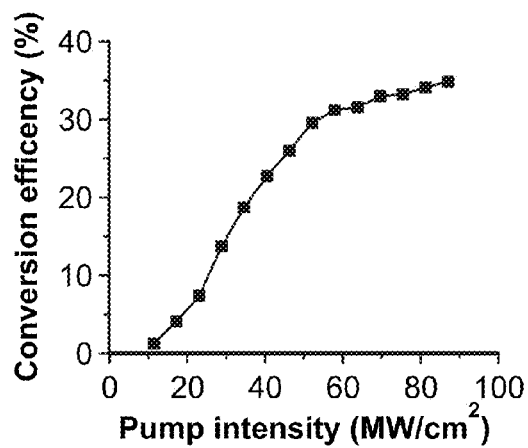
Figure 53D:
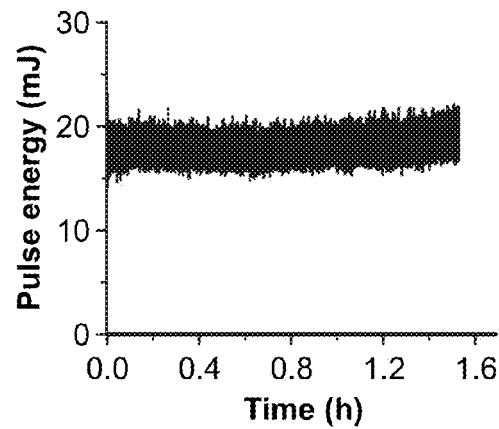

A schematic of our setup is shown in FIG. 52. The $Ba(NO_3)_2$ crystal was pumped by a Q-switched Nd:YAG laser (Continuum Surelite SL III-10) operated with a 10 Hz repetition rate and 5 ns pulse duration (FWHM). A polarizing beam splitter (PBS) was used to purify the polarization of the fundamental 1064 nm laser light. A half-wave plate (HWP) and a second PBS were combined and used as a variable attenuator to adjust the pump pulse energy. A telescope composed of two positive lenses was employed to reduce the pump beam size to match the dimensions of the $Ba(NO_3)_2$ crystal. For the Raman laser, a flat-flat resonator with a cavity length of about 10 cm was used. The resonator end mirror ($M_5$) was coated with high reflectivity at 1197 nm (R>99%). The output coupler ($M_6$) was coated with high reflectivity at 1064 nm (R>99%) and 40% transmission at 1197 nm. The $Ba(NO_3)_2$ crystal, with dimensions of 4×4×38 $mm^3$, was coated with high transmission at 1064 nm and 1197 nm on both faces. The generated 1197 nm Raman laser was directed into an inverted microscope (IX71, Olympus) for PA imaging. An achromatic doublet lens (30 mm focal length, Thorlabs) was applied to focus the Raman laser on the samples. The photoacoustic signals were detected by a focused ultrasonic transducer (V317, Olympus NDT), followed by a preamplifier (5682, Olympus NDT) and a pulse receiver (5073 PR-15-U, Olympus NDT). The collected photoacoustic signals were then sent to a digitizer (USB-5133, National Instrument), and retrieved via a customized LabVIEW program. To perform 3D vibrational photoacoustic imaging, an XY translational stage (ProScan H117, Prior) was employed for raster scanning of samples.

Performances of the Raman laser are shown in FIG. 53. The spectral profile of the Raman laser output, measured by the USB 2000 spectrometer (Ocean Optics), indicates the central wavelength of ca. 1197.6 nm (FIG. 53, Panel A). The maximum pump energy was limited to 60 mJ by crystal damage threshold, with maximum output pulse energy measured to be 21.4 mJ, corresponding to a slope efficiency of 45.4% (FIG. 53, Panel B). The key parameter, conversion efficiency, was defined as the pulse energy of the Raman laser divided by the pulse energy of the pump laser incident on the $Ba(NO_3)_2$ crystal. As shown in FIG. 53, Panel C, the maximum conversion efficiency is about 34.8%, which is much larger than 0.5%, the efficiency for the OPO system we used before (Panther EX Plus, Continuum). The threshold for the 1st Stokes Raman laser was measured to be 11.6 $MW/cm^2$. The discrepancy between the experimental value and the theoretical value (6.1 $MW/cm^2$) may arise from the optical losses resulted from deflection and diffraction. Variation of the 1st Stokes output energy obtained with 60 mJ pump energy (incident on the crystal) were plotted up to 1.5 hours, as shown in FIG. 53, Panel D. The maximum pulse energy drop was 12%, which may be caused by the fluctuation of the pump Nd:YAG laser (6%) and instability of the cavity.

Intramuscular fat was employed to demonstrate the capability of the Raman Laser for photoacoustic imaging. The muscle samples, which were cut into ~10×10×4 $mm^3$ pieces, were harvested from a goat and then preserved in fixative 10% buffered formalin. The small muscle piece was then placed in a glass bottom dish and embedded with $H_2O$-agarose gel for the subsequent photoacoustic imaging. With the pulse energy of 60 μJ on the sample, photoacoustic imaging of intramuscular fat was conducted, as shown in FIG. 54. On-resonant and off-resonant photoacoustic images are shown in FIG. 54, Panels A-B. A strong signal was found at 1197 nm and the contrast nearly disappeared at 1064 nm. These data demonstrate that photoacoustic signal is generated from the C—H bond overtone vibration of lipid. This lipid imaging capability was further confirmed by histological examination of the same tissue (FIG. 54, Panel C), where the same morphology of fat (white color) was observed. On the same setup, 3D photoacoustic imaging of intramuscular fat (FIG. 54, Panel D), was further demonstrated with an axial resolution of 110 μm, a lateral resolution of 60 μm and an imaging depth of ~3 mm.

In conclusion, the data show photoacoustic imaging of lipids with a compact $Ba(NO_3)_2$ crystal-based Raman laser. Up to 21.4 mJ pulse energy at 1197 nm was produced, corresponding to the conversion efficiency of 34.8%. The high conversion efficiency of the Raman laser allows for vibrational photoacoustic tomography by using a larger $Ba(NO_3)_2$ crystal to endure larger incident pulse energy and generate 100 mJ pulse energy at 1197 nm. Notably such energy is considered to be safe for human studies according to the American National Standard (Z136.1-2000). Photoacoustic tomography with overtone vibration as contrast is expected to open new opportunities for bond-selective imaging of biological tissues with an imaging depth and field of view both on the centimeter scale.

Example 24

Data Processing Algorithm

In photoacoustic tomography, the transducer(s) collect the photoacoustic signal from all regions on a spherical plane with radius determined by the time of flight and the speed of sound in the imaging medium. It is an inverse problem to obtain the chromophore information from the time resolved data. This computational task of reconstructing the image from the raw data is usually time consuming. The modified back-projection method is the simplest and most commonly used image reconstruction method in photoacoustic tomography. This Example provides a new algorithm based on the modified back projection to speed up the image reconstruction process. With this new technique the image reconstruction will be three times faster for a 128-element transducer imaging system. A brief description of the proposed algorithm is as follows.

Figure 55:
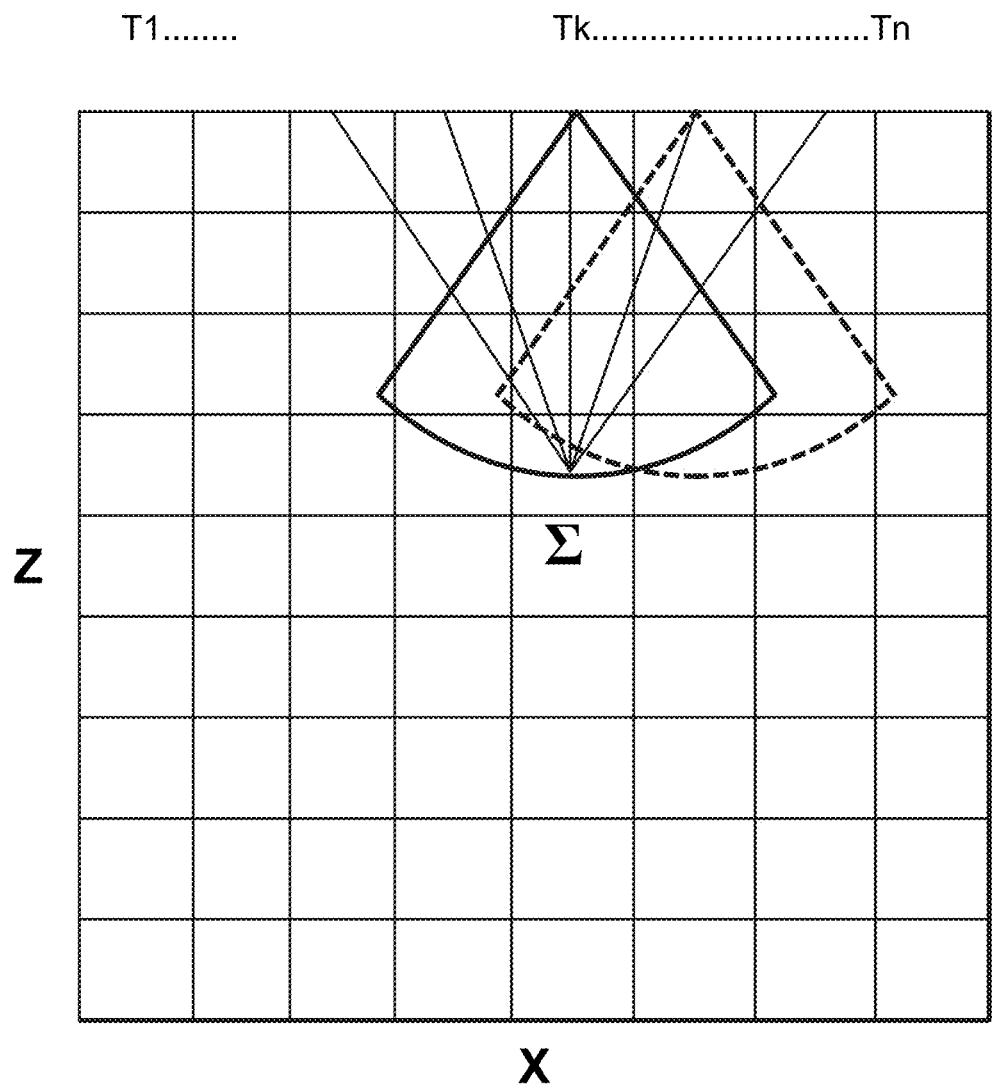
FIG. 55 shows an algorithm for fast image reconstruction.

In reconstruction, a matrix is created with each element corresponding to a pixel (FIG. 55). In the conventional method, first an angle is chosen such that each transducer ($T_1, \ldots T_n$) element has enough sensitivity within that angle. Alternatively, a pixel can only contribute to a set of transducers within that angle (gray lines). For each pixel ($\Sigma$), first the transducer group within the angle is identified, then the time of flight for each transducer is obtained by dividing the distance between the pixel and transducer by $v_s$, the speed of sound. Then all the signals from the transducers are added coherently to obtain the final value for that pixel. This procedure is extremely time consuming as it needs to find the transducer set for each element individually and also it needs to find the distance between each transducer and pixel separately.

In order to speed up the reconstruction procedure, this Example provides a new way which does the reconstruction opposite the above described method. Instead of going from pixel to transducer, the algorithm herein starts with transducer and goes to each pixel. In this procedure, first a center element (say, $T_k$) is considered and starts with a given z (depth). Then, for a given angle, this transducer can contribute to pixels within the arc specified by the angle with radius of curvature equal to z. Next the pixel falls within the arc is determined and assigned the same transducer value ($T_k[t_i]$; $t_i=z/v_s$) to all those pixels. Once it is done for one transducer ($T_k$) for a given z, then for other transducers one only needs to replace the index: replace k by k+1 for the next transducer (shown as dotted line in FIG. 55) or k−1 for the previous transducer. The same procedure is repeated for all z. Because, for each z, only one calculation is needed, this procedure will speed up the reconstruction procedure significantly.

What is claimed is:

1. A method for determining aggressiveness of a cancer, the method comprising:
   conducting an assay on a lipid droplet in order to detect an amount of a biomarker within the lipid droplet; and
   determining aggressiveness of a cancer based upon the amount of the biomarker within the lipid droplet.

2. The method according to claim 1, wherein the biomarker is cholesteryl ester.

3. The method according to claim 1, wherein the assay is carried out using a vibration-based spectroscopic imaging apparatus.

4. The method according to claim 3, wherein the assay detects characteristic bands for a cholesterol ring at 428 $cm^{-1}$, 538 $cm^{-1}$, 614 $cm^{-1}$, and 702 $cm^{-1}$, an ester bond at 1742 $cm^{-1}$, an overtone vibration $CH_2$ deformation at 1448 $cm^{-1}$, and a cholesterol-specific C—H stretch vibration at 2860 $cm^{-1}$.

5. The method according to claim 1, wherein the assay is an in vitro assay that is conducted on one or more intact cells.

6. The method according to claim 3, wherein the apparatus comprises:
   a light source;
   a hollow body coupled to the light source such that light is transmitted through the hollow body; and
   a detector;
   wherein the apparatus is configured such that light from the light source is directed onto a tissue and the detector is coupled to the apparatus such that it can detect a spectroscopic signal generated from tissue that has been excited by the light source.

7. The method according to claim 6, wherein the apparatus further comprises an optical diffuser coupled to the body and positioned to diffuse the light from the light source prior to the light impinging on the tissue.

8. The method according to claim 7, wherein the light source is configured to output a signal that can non-invasively and selectively cause overtone excitation of molecules based on a predetermined chemical bond.

9. The method according to claim 8, wherein the light source is a laser comprising a barium nitrate amplifier and is configured to output a signal at 1197 nm.

10. The method according to claim 6, wherein the detector is an ultrasound transducer.

11. The method according to claim 1, wherein the assay is carried out using a multimodal nonlinear optical microscopy device.

12. The method according to claim 1, wherein prior to the conducting step, the method further comprises obtaining a sample from a patient suspected to have a cancer.

13. The method according to claim 12, wherein prior to the conducting step, the method further comprises enriching for lipid droplets from the sample.

14. The method according to claim 1, further comprising providing a course of treatment to the patient based on results of the determining step.

15. The method according to claim 14, wherein the course of treatment comprises administering an agent that blocks storage of the biomarker within the lipid droplet.

16. The method according to claim 15, wherein the agent is selected from the group consisting of: fatty acid synthase inhibitors, cholesterol acyltransferase (ACAT) inhibitors, low-density lipoprotein (LDL) reducing compounds, and HMG-CoA reductase inhibitors.

17. A method of treating a cancer, the method comprising: administering an agent that blocks storage of cholesteryl ester in a lipid droplet.

18. The method according to claim 17, wherein the agent is selected from the group consisting of: fatty acid synthase inhibitors, cholesterol acyltransferase (ACAT) inhibitors, low-density lipoprotein (LDL) reducing compounds, and HMG-CoA reductase inhibitors.

19. The method according to claim 17, wherein the agent is formulated with a pharmaceutically acceptable carrier.

20. The method according to claim 17, wherein the agent is provided as a unitary dose.

* * * * *